US008445644B2

(12) United States Patent
Greene et al.

(10) Patent No.: US 8,445,644 B2
(45) Date of Patent: May 21, 2013

(54) ERBB INTERFACE PEPTIDOMIMETICS AND METHODS OF USE THEREOF

(75) Inventors: Mark I. Greene, Penn Valley, PA (US); Ramachandran Murali, Drexel Hill, PA (US); Hongtao Zhang, Paoli, PA (US); Mark Richter, Philadelphia, PA (US); Alan Berezov, Glenolden, PA (US); Qingdu Liu, Bala Cynwyd, PA (US); Jinqiu Chen, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 102 days.

(21) Appl. No.: 12/787,594

(22) Filed: May 26, 2010

(65) Prior Publication Data
US 2010/0239587 A1    Sep. 23, 2010

Related U.S. Application Data

(62) Division of application No. 12/625,706, filed on Nov. 25, 2009, now Pat. No. 8,057,799, which is a division of application No. 10/119,288, filed on Apr. 8, 2002, now Pat. No. 7,638,598.

(60) Provisional application No. 60/309,864, filed on Aug. 3, 2001, provisional application No. 60/282,037, filed on Apr. 6, 2001.

(51) Int. Cl.
C07K 16/00 (2006.01)

(52) U.S. Cl.
USPC ........................................................ 530/387.1

(58) Field of Classification Search
None
See application file for complete search history.

(56) References Cited

U.S. PATENT DOCUMENTS

| | | | |
|---|---|---|---|
| 4,522,918 A | 6/1985 | Schlom et al. | |
| 5,338,532 A | 8/1994 | Tomalia et al. | |
| 5,470,571 A | 11/1995 | Herlyn et al. | |
| 5,480,968 A | 1/1996 | Kraus et al. | |
| 5,637,677 A | 6/1997 | Greene et al. | |
| 5,677,171 A | 10/1997 | Hudziak et al. | |
| 5,693,762 A * | 12/1997 | Queen et al. ............... 530/387.3 |
| 5,705,157 A | 1/1998 | Greene | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,811,098 A | 9/1998 | Plowman et al. | |
| 5,821,337 A | 10/1998 | Carter et al. | |
| 5,869,445 A | 2/1999 | Cheever et al. | |
| 5,874,400 A | 2/1999 | Sundelin et al. | |
| 5,874,542 A | 2/1999 | Rockwell et al. | |
| 5,955,311 A | 9/1999 | Rockwell et al. | |
| 5,968,511 A | 10/1999 | Akita et al. | |
| 6,015,567 A | 1/2000 | Hudziak et al. | |
| 6,054,297 A | 4/2000 | Carter et al. | |
| 6,100,377 A | 8/2000 | Greene | |
| 6,165,464 A | 12/2000 | Hudziak et al. | |
| 6,252,050 B1 | 6/2001 | Ashkenazi et al. | |
| 6,342,219 B1 | 1/2002 | Thorpe et al. | |
| 6,417,168 B1 | 7/2002 | Greene et al. | |
| 6,627,196 B1 | 9/2003 | Baughman et al. | |
| 6,790,614 B1 | 9/2004 | Pippig et al. | |
| 6,949,245 B1 | 9/2005 | Sliwkowski | |
| 7,020,563 B1 | 3/2006 | Bentley et al. | |
| 7,638,598 B2 | 12/2009 | Greene et al. | |
| 7,662,374 B2 | 2/2010 | Greene et al. | |
| 7,781,566 B2 | 8/2010 | Greene et al. | |
| 2002/0115209 A1* | 8/2002 | Liu et al. ........................ 435/354 |
| 2010/0076174 A1 | 3/2010 | Greene et al. | |
| 2010/0120688 A1 | 5/2010 | Greene et al. | |
| 2010/0189649 A1 | 7/2010 | Greene et al. | |

FOREIGN PATENT DOCUMENTS

| | | |
|---|---|---|
| WO | WO 98/17797 | 4/1998 |
| WO | WO 01/00244 A2 | 1/2001 |
| WO | WO 02/081649 | 10/2002 |
| WO | WO 03/012072 | 2/2003 |

OTHER PUBLICATIONS

Virji et al (J Gen Microbiol, 1989, 135(12): 3239-3251).*
Roitt et al (Immunology, 4th Edition, 1998, Mosby, London, 7.7-7.8).*
Agus et al., "Targeting Ligand-Activated Erbb2 Signaling Inhibits Breast and Prostate Tumor Growth", Cancer Cell, Aug. 2002, 2(2), 127-137.
Alroy et al., "The ErbB signaling network in embryogenesis and oncogenesis: signal diversification through combinatorial ligand-receptor interactions", FEBS Letters, Jun. 23, 1997, 410(1), 83-86.
Bach et al., "Structural Studies of a Family of High Affinity Ligands for GPIIb/IIIa", J. of American Chemical Society, Apr. 1994, 116(8), 3207-3219.
Banner et al., "Crystal Structure of the Soluble Human 55 kd TNF Receptor-Human TNF β Complex: Implications for TNF Receptor Activation", Cell, May 7, 1993, 73(3), 431-445.
Barrios et al., "Length of the Antibody Heavy Chain Complementarity Determining Region 3 as a Specificity-Determining Factor", J. Molecular Recognition, May 14, 2004, 17(4), 332-338.
Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts", Cancer Res., Jul. 1, 1998, 58(13), 2825-2831.
Berezov et al., "Disabling erbBReceptors with Rationally Designed Exocyclic Mimetics of Antibodies: Structure-Function Analysis", J. of Medicinal Chemistry, Aug. 2, 2001, 44(16), 2565-2574.
Berezov et al., "Disabling Receptor Ensembles with Rationally Designed Interface Peptidomimetics", J. of Biological Chemistry, Aug. 2, 2002, 277(31), 28330-28339.
Bishayee et al., "Phosphorylation of Tyrosine 992, 1068, and 1086 is Required for Conformational Change of the Human Epidermal Growth Factor Receptor c-Terminal Tail", Molecular Biology of the Cell, Mar. 1999, 10(3), 525-536.
Bishayee et al., "Role of Conformational Alteration in the Epidermal Growth Factor Receptor (EGFR) Function", Biochemical Pharmacology, Oct. 15, 2000, 60(8), 1217-1223.

(Continued)

Primary Examiner — Sean Aeder
(74) Attorney, Agent, or Firm — Woodcock Washburn, LLP

(57) ABSTRACT

Peptides, mimetics and antibodies of erbB, TNF, and IgSF receptors and pharmaceutical compositions comprising the same are described. Methods of using such antibodies, peptides, and mimetics in therapeutic, prophylactic, imaging and diagnostic applications are disclosed.

22 Claims, 10 Drawing Sheets

OTHER PUBLICATIONS

Blain et al., "Differential interaction of the cyclin-dependent kinase (Cdk) inhibitor p27Kip1 with cyclin A-Cdk2 and cyclin D2-Cdk4", J. Bio. Chem., Oct. 10, 1997, 272(41), 25863-25872.

Borgelt et al., "Ultra-Rapid High Dose Irradiation Schedules for the Palliation Brain Metastases: Final Results of the First Two Studies by the Radiation Therapy Oncology Group", Int. J. Radiat Oncol. Biol. Phys., Dec. 1981, 7(12), 1633-1638.

Borgelt et al., "The Palliation of Brain Metastases: Final Results of the First Two Studies by the Radiation Therapy Oncology Group", Int. J. Radiat Oncol. Biol. Phys., Jan. 1980, 6(1), 1-9.

Brennan et al., "HER2/Neu: mechanisms of dimerization/oligomerization", Oncogene, Dec. 11, 2000, 19(53), 6093-6101.

Britsch et al., "The ErbB2 and ErbB3 receptors and their ligand, neuregulin-1, are essential for development of the sympathetic nervous system", Genes Dev., Jun. 15, 1998, 12(12), 1825-1836.

Brown et al., "Demonstration by Two-Color Flow Cytometry That Tyrosine Kinase Activity is Required for Down-Modulation of the Oncogenic neu Receptor", DNA Cell Biol., Feb. 1994, 13(2), 193-209.

Burgess et al., "In Solid Phase Syntheses of Oligoureas", American Chemical Society, Orgn., Feb. 19, 1997, 119(7), 1556-1564.

Burgess et al., "Possible Dissociation of the Heparin-Binding and Mitogenic Activities of Heparin-Binding (Acidic Fibroblast) Growth Factor-1 From its Receptor-Binding Activities by Site-Directed Mutagenesis of a Single Lysine Residue", J. of Cell Biology, Nov. 1, 1990, 111(5), 2129-2138.

Cambier, "Inhibitory Receptors Abound", Proc. Natl. Acad. Sci. USA, Jun. 10, 1997, 94(12), 5993-5995.

Capone et al., "Relationship Between Antigen Density and Immunotherapeutic Response Elicited by Monoclonal Antibodies Against Solid Tumors", JNCI, Mar. 1984, 72(3), 673-677.

Carraway et al., "A neu acquaintance for erbB3 and erbB4: a role for receptor heterodimerization in growth signaling", Cell, Jul. 15, 1994, 78(1), 5-8.

Carraway et al., "Location of the Epidermal Growth Factor Binding Site on the EGF Receptor: A Resonance Energy Transfer Study", Biochemistry, Sep. 1990, 29(37), 8741-8747.

Carter et al., "Humanization of an Anti-p185$^{HER2}$ Antibody for Human Cancer Therapy", Proc. Natl. Acad. Sci. USA, May 15, 1992, 89(10), 4285-4289.

Chang et al., "Ligands for ErbB-family receptors encoded by a neuregulin-like gene", Nature, May 29, 1997, 387(6632), 509-512.

Chiri et al., "Evidence for MAP kinase activation during mitotic division", J. Cell Sci., Sep. 1998, 111(pt. 17), 2519-2527.

Chothia et al., "Canonical structures for the hypervariable regions of immunoglobulins", J. Mol. Biol., Aug. 20, 1987, 196(4), 901-917.

Christodoulides et al., "Immunization with synthetic peptides containing epitopes of the class 1 outer-membrane protein of *Neisseria meningitidis*: production of bactericidal antibodies on immunization with a cyclic peptide", J. Genetic Microbiology, Aug. 1993, 139(8), 1729-1738.

Cohen, "A Native 170,000 Epidermal Growth Factor Receptor-Kinase Complex from Shed Plasma Membrane Vesicles", J. Biol. Chem., Feb. 10, 1982, 257(3), 1523-1531.

Daeron et al., "The same tyrosine-based inhibition motif, in the intracytoplasmic domain of Fc gamma RIIB, regulates negatively BCR-, TCR-, and FcR-dependent cell activation", Immunity, Nov. 1995, 3(5), 635-646.

Dahia et al., "Mutation and expression analysis of the p27/kip1 gene in corticotrophin-secreting tumours", Oncogene, Jan. 8, 1998, 16(1), 69-76.

D'Ambrosio et al., "The SHIP phosphatase becomes associated with Fc gammaRIIB1 and is tyrosine phosphorylated during 'negative' signaling", Immunology Letters, Dec. 1996, 54(2-3), 77-82.

Davies et al., "Antibody VH Domains As Small Recognition Units", Nature Biotechnology, May 1995, 13(5), 475-479.

Davies et al., "Single Antibody Domains as Small Recognition Units: Design and in vitro Antigen Selection of Camelized, Human VH Domains With Improved Protein Stability", Protein Engineering Design and Selection, Jun. 1996, 9(16), 531-537.

Deb et al., "A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation", J. Biol. Chem., Jul. 3, 1998, 273(27), 16643-16646.

Decanniere et al., "A Single-Domain Antibody Fragment in Complex With RNase A: Non-Canonical Loop Structures and Nanomolar Affinity Using Two CDR Loops", Structure, Apr. 15, 1999, 7(4), 361-370.

Dermer et al., "Another Anniversary for the War on Cancer", Bio/Technology, Mar. 1994, 12, 320.

Deveraux et al., "X-linked IAP is a direct inhibitor of cell-death proteases", Nature, Jul. 17, 1997, 388(6639), 300-304.

Di Blasio et al., "Noncoded Residues as Building Blocks in the Design of Specific Secondary Structures: Symmetrically Disubstituted Glycines and β-Alanine", Biopolymers, Jul. 1993, 33(7), 1037-1049.

Di Cristofano et al., "Impaired Fas response and autoimmunity in Pten+/− mice", Science, Sep. 24, 1999, 285(5436), 2122-2125.

Di Cristofano et al., "The multiple roles of PTEN in tumor suppression", Cell, Feb. 18, 2000, 100(4), 387-390.

Di Fiore et al., "erbB-2 Is a Potent Oncogene When Overexpressed in NIH/3T3 Cells", Science, Jul. 10, 1987, 237(4811), 178-182.

Doherty et al., "The HER-2/neu Receptor Tyrosine Kinase Gene Encodes a Secreted Autoinhibitor", PNAS, Sep. 14, 1999, 96(19), 10869-10874.

Dougall et al., "The neu-oncogene: signal transduction pathways, transformation mechanisms and evolving therapies", Oncogene, Aug. 1994, 9(8), 2109-2123.

Drebin et al., "Development of Monoclonal Antibodies Reactive with the Product of the neu Oncogene", Symp Fundam Cancer Res., Dec. 1986, 38, 277-289.

Drebin et al., "Monoclonal antibodies reactive with distinct domains of the neu oncogene-encoded p185 molecule exert synergistic anti-tumor effects in vivo", Oncogene, Mar. 1988, 2(3), 273-277.

Drebin et al., "Down-modulation of an oncogene protein product and reversion of the transformed phenotype by monoclonal antibodies", Cell, Jul. 1985, 41(13), 695-706.

Drebin et al., "Inhibition of Tumor Growth by a Monoclonal Antibody Reactive With an Oncogene-Encoded Tumor Antigen", Proc. Natl. Acad. Sci. USA, Dec. 1, 1986, 83(23), 9129-9133.

Drebin et al., "Monoclonal antibodies identify a cell-surface antigen associated with an activated cellular oncogene", Nature, Dec. 6-12, 1984, 312(5994), 545-548.

Drebin et al., "Monoclonal antibodies Specific for the neu oncogene product directly mediate anti-tumor effects in vivo", Oncogene, Mar. 1988, 2(3), 387-394.

Dudek et al., "Regulation of neuronal survival by the serine-threonine protein kinase Akt", Science, Jan. 31, 1997, 275(5300), 661-665.

Dumoulin et al., "Single-Domain Antibody Fragments With High Conformational Stability", Protein Science, Mar. 2002, 11(3), 500-515.

Eck et al., "The Structure of Human Lymphotoxin (Tumor Necrosis Factor-β) at 1.9-Å Resolution", J. of Biological Chemistry, Feb. 5, 1992, 267(4), 2119-2122.

Eck et al., "The Structure of Tumor Necrosis Factor-α at 2.6 Å Resolution: Implications or Receptor Binding", J. of Biological Chemistry, Oct. 10, 1989, 264(29), 17595-17605.

Eigenbrot et al., "X-ray structures of fragments from binding and nonbinding versions of a humanized anti-CD18 antibody: structural indications of the key role of VH residues 59 to 65", Proteins, Jan. 1994, 18(1), 49-62.

Eigenbrot et al., "X-ray structures of the antigen-binding domains from three variants of humanized anti-p185HER2 antibody 4D5 and comparison with molecular modeling", J. Mol. Biology, Feb. 20, 1993, 229(4), 969-995.

Erickson et al., "ErbB3 is required for normal cerebellar and cardiac development: a comparison with ErbB2-and heregulin-deficient mice", Development, Dec. 1997, 124(24), 4999-5011.

Fendly et al., "Characterization of Murine Monoclonal Antibodies Reactive to Either the Human Epidermal Growth Factor Receptor or HER2/neu Gene Product", Cancer Research, Mar. 1, 1990, 50(5), 1550-1558.

Feng, "Shp-2 tyrosine phosphatase: signaling one cell or many", Exp. Cell Res., Nov. 25, 1999, 253(1), 47-54.

Ferguson et al., "Extracellular Domains Drive Homo—But Not Hetero-Dimerization of erbB Receptors", Embo J., Sep. 1, 2000, 19(17), 4632-4643.

Fernandez-Pol, "Epidermal Growth Factor Receptor of A431 Cells", Biological Chemistry, Apr. 25, 1985, 260(8), 5003-5011.

Fujioka et al., "A novel membrane glycoprotein, SHPS-1, that binds the SH2-domaincontaining protein tyrosine phosphatase SHP-2 in response to mitogens and cell adhesion", Molecular and Cellular Biology, Dec. 1996, 16(12), 6887-6899.

Furnari et al., "Growth suppression of glioma cells by PTEN requires a functional phosphatase catalytic domain", Proc. Natl. Acad. Sci. USA, Nov. 11, 1997, 94(23), 12479-12484.

Furnari et al., "The phosphoinositol phosphatase activity of PTEN mediates a serum-sensitive G1 growth arrest in glioma cells", Cancer Research, Nov. 15, 1998, 58(22), 5002-5008.

Gainer et al., "Gene Gun Transfection of Human Glioma and Melanoma Cell Lines With Genes Encoding Human IL-12 and GM-CSF", J. Neuro-Oncology, Mar. 2000, 47(1), 23-30.

Garrett et al., "Crystal Structure of the First Three Domains of the Type-1 Insulin-Like Growth Factor Receptor", Nature, Jul. 23, 1998, 394(6691), 395-399.

Gasparini et al., "Human Breast Cancer—Prognostic Significance of the c-erbB-2 Oncoprotein Compared with Epidermal Growth Factor Receptor, DNA Ploidy, and Conventional Pathologic Features", J. of Clinical Oncology, May 1992, 10(5), 686-695.

Gill et al., "Calculation of Protein Extinction Coefficients From Amino Acid Sequence Data", Analytical Biochemistry, Nov. 1, 1989, 182(2), 319-326.

Goodman et al., "Peptidomimetic Building Blocks for Drug Discovery: an Overview", Pure & Applied Chemistry, Jun. 1996, 68(6), 1303-1308.

Gura, "Systems for Identifying New Drugs are Often Faulty", Science, Nov. 7, 1997, 278(5340), 1041-1042.

Hanessian et al., "Design and Synthesis of Conformationally Constrained Amino Acids as Versatile Scaffolds and Peptide Mimetics", Tetrahedron, Sep. 22, 1997, 53(38), 12789-12854.

Hansen et al., "Re-Examination and Further Development of a Precise and Rapid Dye Method for Measuring Cell Growth/Cell Kill", J. of Immunological Methods, May 12, 1989, 119(2), 203-210.

Heldin, "Dimerization of Cell Surface Receptors in Signal Transduction", Cell, Jan. 27, 1995, 80(2), 213-223.

Hemmings, "Akt signaling: linking membrane events to life and death decisions", Science, Jan. 31, 1997, 275(5300), 628-630.

Hruby, "Conformational and Topographical Considerations in the Design of Biologically Active Peptides", Biopolymers, Jul. 1993, 33(7), 1073-1082.

Huang et al., "Proxy activation of protein ErbB2 by heterologous ligands implies a heterotetrameric mode of receptor tyrosine kinase interaction", Biochem. J., Apr. 1, 1998, 331(Pt. 1), 113-119.

Huang et al., "The enhanced tumorigenic activity of a mutant epidermal growth factor receptor common in human cancers is mediated by threshold levels of constitutive tyrosine phosphorylation and unattenuated signaling", J. Biol. Chem., Jan. 31, 1997, 272(5), 2927-2935.

Irmler et al., "Inhibition of death receptor signals by cellular FLIP [see comments]", Nature, Jul. 10, 1997, 388(6638), 190-195.

Jackson et al., "The Biological Action of Choriogonadotropin is Not Dependent on the Complete Native Quaternary Interactions Between the Subunits", Molecular Endocrinology, Dec. 1999, 13(12), 2175-2188.

Jackson et al., "Template-constrained cyclic peptides: design of high-affinity ligands for GPIIb/IIIa", J. of American Chemical Society, Apr. 1994, 116(18), 3220-3230.

Jacob et al., "Priming Immunization Against Cholera Toxin and *E. coli* Heat-Labile Toxin by a Cholera Toxin Short Peptide-Beta-Galactosidase Hybrid Synthesized in *E. coli*.", EMBO J., Dec. 1, 1985, 4(12), 3339-3343.

Jardines et al., "Neu(c-erbB-2/HER2) and the epidermal growth factor receptor (EGFR) in breast cancer", Pathobiology, Jul. 1993, 61(5-6), 268-282.

Jorissen et al., "Characterization of a Comparative Model of the Extracellular Domain of the Epidermal Growth Factor Receptor", Protein Science, Feb. 2000, 9(2), 310-324.

Kauffmann-Zeh et al., "Suppression of c-Myc-induced apoptosis by Ras signalling through PI(3)K and PKB", Nature, Feb. 6, 1997, 385(6616), 544-548.

Kharitonenkov et al., "A family of proteins that inhibit signalling through tyrosine kinase receptors", Nature, Mar. 13, 1997, 386(6621), 181-186.

Kieber-Emmons et al., "Therapeutic peptides and peptidomimetics", Curr. Opin. Biotechnol., Aug. 1997, 8(4), 435-441.

Kobrin et al., "A V Region Mutation in a Phosphochoine-Binding Monoclonal Antibody Results in Loss of Antigen Binding", J. Immunology, Mar. 15, 1991, 146(6), 2017-2020.

Koide et al., "DNA Vaccines", Japanese J. Pharmacol., Mar. 2000, 83(3), 167-174.

Kokai et al., "Stage-and tissue-specific expression of the neu oncogene in rat development", Proc. Natl. Acad. Sci. USA, Dec. 1987, 84(23), 8498-8501.

Kokai et al., "Synergistic Interaction of p185c-neu and the EGF Receptor Leads to Transformation of Rodent Fibroblasts", Cell, Jul. 28, 1989, 58(2), 287-292.

Koprowski et al., "Expression of the Receptor for Epidermal Growth Factor Correlates With Increased Dosage of Chromosome 7 in Malignant Melanoma", Somatic Cell and Molecular Genetics, May 1985, 11(3), 297-302.

Koskinen et al., "Asymmetric Intramolecular Cyclopropanation: Synthesis of Conformationally Constrained Aminocyclopropane Carboxylic Acids", ACTA Chem. Scand., Aug. 1996, 50(4), 323-327.

Kramer et al., "Neuregulins with an Ig-like domain are essential for mouse myocardial and neuronal development", Proc. Natl. Acad. Sci. USA, May 14, 1996, 93(10), 4833-4838.

Kuby et al., "Antigens", Immunology, Second edition, 1994, Chapter 4, 86-96.

Kühn et al., "Fmoc Protected Peptide Mimetic Based on a Cyclohexane Framework and Incorporation Into Angiotensin II", Tetrahedron, Sep. 15, 1997, 53(37), 12497-12504.

Kumagai et al., "The Role of District p185$^{neu}$ Extracellular Subdomains for Dimerization With the Epidermal Growth Factor Receptor and EGF Mediated Signaling", Proc. Nat. Acad. Sci. USA, May 8, 2001, 98(10), 5526-5531.

Kuriyama et al., "Particle-Mediated Gene Transfer Into Murine Livers Using a Newly Developed Gene Gun", Gene Therapy, Jul. 2000, 7(13), 1132-1136.

Landgraf et al., "Heregulin Reverses the Oligomerization of HER3", Biochemistry, Jul. 25, 2000, 39(29), 8503-8511.

Lazar et al., "Transforming Growth Factor α: Mutation of Aspartic Acid 47 and Leucine 48 Results in Different Biological Activities", Molecular and Cellular Biology, Mar. 1988, 8(3), 1247-1252.

LeBien et al., "Use of Monoclonal Antibodies, Morphology, and Cytochemistry to Probe the Cellular Heterogeneity of Acute Leukemia and Lymphoma", Cancer Res., Nov. 1981, 41(11 Pt 2), 4776-4780.

Lee et al., "Reduced expression of the CDK inhibitor p27(KIP1) in rat two-stage bladder carcinogenesis and its association with expression profiles of p21(WAF1/Cip1) and p53", Carcinogenesis, Sep. 1999, 20(9), 1697-1708.

Lee et al., "Requirement for neuregulin receptor erbB2 in neural and cardiac development", Nature, Nov. 23, 1995, 378(6555), 394-398.

Lees, "Cyclin dependent kinase regulation", Curr. Opin., Cell Biology, Dec. 1995, 7(16), 773-780.

Lemmon et al., "Two EGF Molecules Contribute Additively to Stabilization of the EGFR Dimer", EMBO J., Jan. 15, 1997, 16(2), 281-294.

Li et al., "Control of apoptosis and mitotic spindle checkpoint by surviving", Nature, Dec. 10, 1998, 396(6711), 580-584.

Li et al., "Homology Modeling Using Simulated Annealing of Restrained Molecular Dynamics and Conformational Search Calculations With CONGEN: Application in Predicting the Three-Dimensional Structure of Murine Homeodomain Msx-1", Protein Science, May 1997, 6(5), 956-970.

Li et al., "PTEN, a putative protein tyrosine phosphatase gene mutated in human brain, breast, and prostate cancer", Science, Mar. 28, 1997, 275(5308), 1943-1947.

Liu et al., "Domain-specific gene disruption reveals critical regulation of neuregulin signaling by its cytoplasmic tail", Proc. Natl. Acad. Sci. USA, Oct. 27, 1998, 95(22), 13024-13029.

Lu et al., "The PTEN/MMAC1/TEP tumor suppressor gene decreases cell growth and induces apoptosis and anoikis in breast cancer cells", Oncogene, Nov. 25, 1999, 18(50), 7034-7045.

MacCallum et al., "Antibody-antigen interactions: contact analysis and binding site topography", J. Mol. Biol., Oct. 11, 1996, 262(5), 732-745.

Magerstadt, "Antibody Conjugates and Malignant Disease", CRC Press, Boca Raton, USA, 1991, 6 pages.

Magliani et al., "Therapeutic Potential of Antiidiotypic Single Chain Antibodies With Yeast Killer Toxin Activity", Nature Biotechnology, Feb. 1997, 15(2), 155-158.

Manning et al., "Design of cyclic and linear peptide antagonists of vasopressin and oxytocin: current status and future directions", Reg. Peptides, Apr. 29, 1993, 45(1-2), 279-283.

Matsuyama et al., "A Novel Extracellular Cyclic Lipopeptide Which Promotes Flagellum-Dependent and-Independent Spreading Growth of *Serratia marcescens*", J. Bacteriol., Mar. 1992, 174(6), 1769-1776.

McBride et al., "Identification of chymotrypsin inhibitors from a second-generation template assisted combinatorial peptide library", J. Pept. Sci., Sep. 2000, 6(9), 446-452.

McInnes et al., "Growth Factor Receptors: Structure, Mechanism and Drug Discovery", Biopolymers, Dec. 1998, 43(5), 339-366.

McIntyre et al., "Differential expression of the cyclin-dependent kinase inhibitor P27 in primary hepatocytes in early-mid G1 and G1/S transitions", Oncogene, Aug. 12, 1999, 18(32), 4577-4585.

Meyer et al., "Multiple essential functions of neuregulin in development", Nature, Nov. 23, 1995, 378(6555), 386-390.

Moore, "Designing peptide mimetics", Trends Pharmacol. Sci., Apr. 1994, 15(4), 124-129.

Moscatello et al., "Constitutive activation of phosphatidylinositol 3-kinase by a naturally occurring mutant epidermal growth factor receptor", J. Biol. Chem., Jan. 2, 1998, 273(1), 200-206.

Murali et al., "Structural analysis of p185(c-neu) and epidermal growth factor receptor tyrosine kinases: Oligomerization of kinase domains", Proc. Natl. Acad. Sci. USA, Jun. 25, 1996, 93(13), 6252-6257.

Murali et al., "Structure-based design of immunologically active therapeutic peptides", Immunol. Res., Jan. 1998, 17(1-2), 163-169.

Murzin et al., "SCOP: A Structural Classification of Proteins Database for the Investigation of Sequences and Structures", J. Mol. Biol., Apr. 7, 1995, 247(4), 536-540.

Muyldermans et al., "Unique Single-Domain Antigen Binding Fragments Derived From Naturally Occurring Camel Heavy-Chain Antibodies", J. of Molecular Recognition, Mar. 1999, 12(2), 131-140.

Myers et al., "PTEN: sometimes taking it off can be better than putting it on", Am. J. Hum. Genet., Dec. 1997, 61(6), 1234-1238.

Myers et al., "The lipid phosphatase activity of PTEN is critical for its tumor supressor function", Proc. Natl. Acad. Sci. USA, Nov. 10, 1998, 95(23), 13513-13518.

Nagane et al., "A common mutant epidermal growth factor receptor confers enhanced tumorigenicity on human glioblastoma cells by increasing proliferation and reducing apoptosis", Cancer Research, Nov. 1, 1996, 56(21), 5079-5086.

Nagane et al., "Drug resistance of human glioblastoma cells conferred by a tumor-specific mutant epidermal growth factor receptor through modulation of Bcl-XL and caspase-3-like proteases", Proc. Natl. Acad. Sci. USA, May 12, 1998, 95(10), 5724-5729.

Naismith et al., "Crystallographic Evidence for Dimerization of Unliganded Tumor Necrosis Factor Receptor", J. of Biological Chemistry, Jan. 2, 1995, 270(22), 13303-13307.

Naismith et al., "Modularity in the TNF-Receptor Family", Trends in Biochemical Sciences, Feb. 1998, 23(2), 74-79.

Nayak et al., "B Cell Responses to a Peptide Epitope. V. Kinetic Regulation of Repertoire Discrimination and Antibody Optimization for Epitope", J. of Immunology, Oct. 1998, 161(7), 3510-3519.

Nishikawa et al., "A mutant epidermal growth factor receptor common in human glioma confers enhanced tumorigenicity", Proc. Natl. Acad. Sci. USA, Aug. 2, 1994, 91(16), 7727-7731.

O'Rourke et al., "Inhibition of a Naturally Occurring EGFR Oncoprotein by the p185neu Ectodomain: Implications for Subdomain Contributions to Receptor Assembly," Oncogene, Mar. 5, 1998, 16(9), 1197-1207.

O'Rourke et al., "Conversion of a radioresistant phenotype to a more sensitive one by disabling erbB receptor signaling in human cancer cells", Proc. Natl. Acad. Sci. USA, Sep. 1, 1998, 95(18), 10842-10847.

O'Rourke et al., "Trans Receptor Inhibition of Human Glioblastoma Cells by erbB Family Ectodomains", Proc. Natl. Acad. Sci. USA, Apr. 1, 1997, 94(7), 3250-3255.

Pages et al., "sst2 somatostatin receptor mediates cell cycle arrest and induction of p27(Kip1). Evidence for the role of SHP-1", J. Biol. Chem., May 21, 1999, 274(21), 15186-15193.

Park et al., "Rationally Designed Anti-HER2/neu Peptide Mimetic Disables P185$^{HER2/neu}$ Tyrosine Kinases in vitro and in vivo", Nature Biotechnology, Feb. 2000, 18(2), 194-198.

Park et al., Induction of the Tat-binding protein 1 gene accompanies the disabling of oncogenic erbB receptor tyrosine kinases. Proc. Nat. Acad. Sci. USA, May 25, 1999, 96(11), 6434-6438.

Patel et al., "A Cyclic Peptide Analogue of the Loop III Region of Platelet-derived Growth Factor-BB is a Synthetic Antigen for the Native Protein", J. of Peptide Research, Jan. 1999, 53(1), 68-74.

Peczuh et al., "Peptide and Protein Recognition by Designed Molecules", Chem. Rev., Jun. 20, 2000, 100(17), 2479-2494.

Pegram et al., "Phase II Study of Receptor-Enhanced Chemosensitivity Using Recombinant Humanized Anti-p185$^{HER2/neu}$ Monoclonal Antibody Plus Cisplatin in Patients With HER2/neu-overexpressing Metastatic Breast Cancer Refractory to Chemotherapy Treatment", J. of Clinical Oncology, Aug. 1998, 16(8), 2659-2671.

Peterson et al., "Bacterial Expression and Characterization of Recombinant Biologically-Active Anti-Tyrosine Kinase Receptor Antibody-Forms", DNA Cell Biology, Dec. 1998, 17(12), 1031-1040.

Pianetti et al., "Her-2/neu overexpression induces NF-kappaB via a PI3-kinase/Akt pathway involving calpain-mediated degradation of IkappaB-alpha that can be inhibited by the tumor suppressor PTEN", Oncogene, Mar. 15, 2001, 20(11), 1287-1299.

Pinkas-Kramarski et al., "Differential Expression of NDF/Neuregulin Receptors ErbB-3 andErbB-4 and Involvement in Inhibition of Neuronal Differentiation", Oncogene, Dec. 4, 1997, 15(23), 2803-2815.

Pinkas-Kramarski et al., "Diversification of Neu differentiation factor and epidermal growth factor signaling by combinatorial receptor interactions", EMBO J., May 15, 1996, 15(10), 2452-2467.

Posthumus et al., "Immunogenicity of Peptides Simulating a Neutralization Epitope of Transmissible Gastroenteritis Virus", Virology, May 1991, 182(1), 371-375.

Qian et al., "Domain-specific interactions between the p185 neu and EGF receptor kinases determine differential signalling outcomes", J. of Biological Chemistry, Jan. 8, 1999, 274(12), 574-583.

Qian et al., "Heterodimerization of Epidermal Growth Factor Receptor and Wild-Type of Kinase-Deficient Neu: A Mechanism of Interreceptor Kinase activation and Transphosphorylation", Proc. Natl. Acad. Sci. USA, Feb. 15, 1994, 91(4), 1500-1504.

Qian et al., "Identification of p185 sequences required for monoclonal antibody-or ligand-mediated receptor signal attenuation", DNA Cell Biology, Dec. 1997, 16(12), 1395-1405.

Qian et al., "Inhibition of p185$^{neu}$ kinase activity and cellular transformation by co-expression of a truncated neu protein", Oncogene, Nov. 21, 1996, 13(10), 2149-2157.

Qian et al., "Intermolecular association and trans-phosphorylation of different neu-kinase forms permit SH2-dependent signaling and oncogenic transformation", Oncogene, Jan. 5, 1995, 10(1), 211-219.

Qian et al., "Kinase-deficient neu proteins suppress epidermal growth factor receptor function and abolish cell transformation", Oncogene, May 1994, 9(5), 1507-1514.

Reichmann, "Rearrangement of the Former VL Interface in the Solution Structure of a Camelised, Single Antibody VH Domain", J. of Molecular Biology, Jun. 28, 1996, 259(5), 957-969.

Riese et al., "Activation of ErbB4 by the bifunctional epidermal growth factor family hormone epiregulin is regulated by ErbB2", J. Biol. Chem., May 1, 1998, 273(18), 11288-11294.

Riethmacher et al., "Severe neuropathies in mice with targeted mutations in the ErbB3 receptor", Nature, Oct. 16, 1997, 389(6652), 725-730.

Rudikoff et al., "Single Amino Acid Substitution Altering Antigen-Binding Specificity", Proc Natl Acad Sci USA, Mar. 1982, 79(6), 1979-1983.

Samata et al., "Ligand and p185$^{c-neu}$ Density Govern Receptor Interacations and Tyrosine Kinase Activation", Proc. Natl. Acad. Sci. USA, Mar. 1994, 91, 1711-1715.

Saragovi et al., "Design and Synthesis of a Mimetic from an Antibody Complementarity-Determining Region", Science, Aug. 16, 1991, 253(5021), 792-795.

Saragovi et al., "Constrained peptides and mimetics as probes of protein secondary structures", Immunomethods, Aug. 1992, 1(1), 5-9.

Saxon et al., "Mutagenesis Reveals a Role for Epidermal Growth Factor Receptor Extracellular Subdomain IV in Ligand Binding", J. of Biological Chemistry, Oct. 1, 1999, 274(40), 28356-28362.

Saxton et al., "Abnormal mesoderm patterning in mouse embryos mutant for the SH2 tyrosine phosphatase Shp-2", EMBO J., May 1, 1997, 16(9), 2352-2364.

Schechter et al., "The neu oncogene: an erb-B-related gene encoding a 185,000-Mr tumour antigen", Nature, Dec. 6-12, 1984, 312(5994), 513-516.

Schmidt et al., "Targeted inhibition of tumour cell growth by a bispecific single-chain toxin containing an antibody domain and TGF alpha", Brit. J. Cancer, Sep. 1996, 74(6), 853-862.

Scott et al., "p185$^{HER2}$ Signal Transduction in Breast Cancer Cells", J. Biochemistry, Aug. 5, 1991, 266(22), 14300-14305.

Shayesteh et al., "PIK3CA is implicated as an oncogene in ovarian cancer", Nat. Genet., Jan. 1999, 21(1), 99-102.

Shi et al., "Molecular mechanism for the Shp-2 tyrosine phosphatase function in promoting growth factor stimulation of Erk activity", Molecular and Cellular Biology, Mar. 2000, 20(5), 1526-1536.

Shi et al., "The Shp-2 tyrosine phosphatase has opposite effects in mediating the activation of extracellular signal-regulated and c-Jun NH2-terminal mitogen-activated protein kinases", J. Biol. Chem., Feb. 27, 1998, 273(9), 4904-4908.

Simpson et al., "Influence of Location and Extent of Surgical Resection on Survival of Patients with Glioblastoma Multiforme: Results of Three Consecutive Radiation Therapy Oncology Group (RTOG) Clinical Trials", Int. J. Radiat. Oncol. Biol. Phys., May 20, 1993, 26(2), 239-244.

Stambolic et al., "Negative regulation of PKB/Akt-dependent cell survival by the tumor suppressor PTEN", Cell, Oct. 2, 1998, 95(1), 29-39.

Steck et al., "Identification of a candidate tumour suppressor gene, MMAC1, at chromosome 10q23.3 that is mutated in multiple advanced cancers", Nat. Genet., Apr. 1997, 15(4), 356-362.

Stryer et al., "Protein Structure and Function", Biochemistry, Third edition, W.H. Freeman Company, NY, Chapter 2, 1998, 31-33.

Summerfield et al., "Identification of Residues of the Epidermal Growth Factor Receptor Proximal to Residue 45 of Bound Epidermal Growth Factor", J. of Biological Chemistry, Aug. 16, 1996, 271(33), 19656-19659.

Sun et al., "Cell death mediated by Fas-FasL interaction between glial cells and MBP-reactive T cells", J. Neurosci. Res., May 15, 1998, 52(4), 458-467.

Tahna et al., "Optimal Design Features of Camelized Human Single-Domain Antibody Libraries", J. of Biological Chemistry, Jul. 6, 2001, 276(27), 24774-24780.

Takada et al., "Roles of the complex formation of SHPS-1 with SHP-2 in insulin-stimulat.ed mitogen-activated protein kinase activation", J. Biol. Chem., Apr. 10, 1998, 273(15), 9234-9242.

Takasaki et al., "Structure-Based Design and Characterization of Exocyclic Peptidomimetics That Inhibit TNF Alpha Binding to its Receptor", Nature Biotechnology, Nov. 1997, 15(12), 1266-1270.

Tamura et al., "Inhibition of cell migration, spreading, and focal adhesions by tumor suppressor PTEN", Science, Jun. 5, 1998, 280(5369), 1614-1617.

Tejero et al., "Simulated Annealing With Restrained Molecular Dynamics Using CONGEN: Energy Refinement of the NMR Solution Structures of Epidermal and Type-α Transforming Growth Factors", Protein Science, Apr. 1996, 5(4), 578-592.

Tonks et al., "Structural assets of a tumor suppressor", Science, Dec. 10, 1999, 286(5447), 2096-2097.

Tzahar et al., Bivalence of EGF-Like Ligands Drives the ErbB Signaling Network, EMBO J., Aug. 15, 1997, 16(16), 4938-4950.

Tzahar et al., "The ErbB-2/HER2 oncogenic receptor of adenocarcinomas: from orphanhood to multiple stromal ligands", Biochim. Biophys. Acta., Feb. 20, 1998, 1377(1), M25-M37.

Ullrich et al., "Human Epidermal Growth Factor Receptor cDNA Sequence and Aberrant Expression of the Amplified Gene in A431 Epidermoid. Carcinoma Cells", Nature, May 31-Jun. 6, 1984, 309(5967), 418-425.

Valero et al., "Cyclic peptides as conformationally restricted models of viral antigens: application to foot-and-mouth disease virus", Biomed. Pept. Proteins Nucleic Acids, Apr. 1995, 1(3), 133-140.

Van Der Werf et al., "Ability of Linear and Cyclic Peptides of Neutralization Antigenic Site 1 of Poliovirus Type 1 to Induce Virus Cross-Reactive and Neutralizing Antibodies", Research in Virology, Nov.-Dec. 1994(6), 145, 349-359.

Van Regenmortel, "Mapping Epitope Structure and Activity: From One-Dimensional Prediction to Four-Dimensional Description of Antigenic Specificity", Methods, Jun. 1996, 9(3), 465-472.

Van Regenmortel, "Structural and Functional Approaches to the Study of Protein Antigenicity", Immunology Today, Aug. 1989, 10(18), 266-272.

Veillette et al., "High expression of inhibitory receptor SHPS-1 and its association with protein-tyrosine phosphatase SHP-1 in macrophages", J. Biol. Chem., Aug. 28, 1998, 273(35), 22719-22728.

Vita et al., "Novel Miniproteins Engineered by the Transfer of Active Sites to Small Natural Scaffolds", Biopolymers, Dec. 6, 1998, 47(1), 93-100.

Vogelstein et al., "Surfing the p53 network", Nature, Nov. 16, 2000, 408(6810), 307-310.

Voice et al., "Four human ras homologs differ in their abilities to activate Raf-1, induce transformation, and stimulate cell motility", J. Biol. Chem., Jun. 11, 1999, 274(24), 17164-17170.

Wada et al., "Anti-receptor antibodies reverse the phenotype of the cells transformed by two interacting proto-oncogene encoded receptor proteins", Oncogene, Apr. 1990, 5(4), 489-495.

Wada et al., "Intermolecular Association of the P185$^{Neu}$ Protein and EGF Receptor Modulates EGF Receptor Function", Cell, Jun. 29, 1990, 61(7), 1339-1347.

Waid et al., "Constrained Amino Acids: An Approach to the Synthesis of 3-Substituted Prolines", Tetrahedron Letters, Jun. 10, 1996, 37(24), 4091-4094.

Wang et al., ErbB2 Expression Increases the Spectrum and Potency of Ligand-Mediated Signal Transduction Through ErbB4, Proc. Natl. Acad. Sci. USA, Jun. 9, 1998, 95(12), 6809-6814.

Ward et al., "Insulin and Epidermal Growth Factor Receptors Contain the Cysteine Repeat Motif Found in the Tumor Necrosis Factor Receptor", Proteins, Jun. 1995, 22(2), 141-153.

Williams et al., "Immune Response to a Molecularly Defined Internal Image Idiotope", J. of Immunology, Jun. 15, 1989, 142(12), 4392-4400.

Witte et al., "Monoclonal Antibodies Targeting the VEGF Receptor-2 (Flk1/KRD) as an Anti-Angiogenic Therapeutic Strategy", Cancer and Metastasis Reviews, Jun. 1998, 17(2), 155-161.

Woltjer et al., "Direct Identification of Residues of the Epidermal Growth Factor Receptor in Close Proximity to the Amino Terminus of Bound Epidermal Growth Factor", Proc. Natl. Acad. Sci. USA, Sep. 1, 1992, 89(17), 7801-7805.

Wong et al., "Structural alterations of the epidermal growth factor receptor gene in human gliomas", Proc. Natl. Acad. Sci. USA, Apr. 1992, 89(7), 2965-2969.

Wood et al., "Novel cyclization chemistry especially suited for biologically derived, unprotected peptides", J. Pep. Prot. Res., Jun. 1992, 39(6), 533-539.

Worthylake et al., "ErbB-2 amplification inhibits down-regulation and induces constitutive activation of both ErbB-2 and epidermal growth factor receptors", J. Biol. Chem., Mar. 26, 1999, 274(13), 8865-8874.

Wu et al., "Inhibition of EGFR-mediated phosphoinositide-3-OH kinase (PI3-K) signaling and glioblastoma phenotype by Signal-Regulatory Proteins (SIRPs)", Oncogene, Aug. 17, 2000, 19(35), 3999-4010.

Wu et al., "The PTEN/MMAC1 tumor suppressor phosphatase functions as a negative regulator of the phosphoinositide 3-kinase/Akt pathway", Proc. Natl. Acad. Sci. USA, Dec. 22, 1998, 95(26), 15587-15591.

Yamauchi et al., "Epidermal growth factor-induced association of the SHPTP2 protein tyrosine phosphatase with a 115-kDa phosphotyrosine protein", J. Biol. Chem., Jun. 23, 1995, 270(25), 14871-14874.

Yamauchi et al., "Introduction of a Foreign Gene Into Medakafish Using the Particle Gun Method", J. of Experimental Zoology, Jun. 23, 2000, 287(25), 285-293.

Ye et al., "Augmentation of a humanized anti-HER2 mAb 4D5 induced growth inhibition by a human-mouse chimeric anti-EGF receptor mAb C225", Oncogene, Jan. 21, 1999, 18(3), 731-738.

Yip et al., "Identification of Epitope Regions Recognized by Tumor Inhibitory and Stimulatory Anti-ErbB-2 Monoclonal Antibodies: Implications for Vaccine Design", J. Immunology, Apr. 15, 2001, 166(8), 5271-5278.

Zajchowski et al., "Identification of Gene Expression Profiles That Predict the Aggressive behavior of Breast Cancer Cells", Cancer Res., Jul. 1, 2001, 61(13), 5168-5178.

Zhang et al., "Absence of autophosphorylation site Y882 in the p185neu oncogene product correlates with a reduction of transforming potential", Oncogene, Jun. 4, 1998, 16(22), 2835-2842.

Zhang et al., "New Perspectives on Anti-HER2/Neu Therapeutics", Drug News Perspect, Aug. 2000, 13(6), 325-329.

Zhang et al., "Protein Quantification from Complex Protein Mixtures Using a Novel Proteomics Methodology with Single Cell Resolution", Proc. Natl. Acad. Sci. USA, May 8, 2001, 98(10), 5497-5502.

Zhang et al., "Shared antigenic epitopes and pathobiological functions of anti-p185$^{her2/neu}$ monoclonal antibodies", Experimental and Molecular Pathology, Sep. 1999, 67(1), 15-25.

Zhang et al., "Synthetic CD4 Exocyclic Peptides Antagonize CD4 Holoreceptor Binding and T-Cell Activation", Nature Biotechnology, Apr. 1996, 14(4), 472-475.

Zhang et al., "Synthetic CD4 Exocyclics Inhibit Binding of Human Immunodeficiency Virus Type 1 Envelope to CD4 and Virus Replication in T Lymphocytes", Nature Biotechnology, Feb. 1997, 15(2), 150-154.

Zhang et al., "VCP, a Weak ATPase Involved in Multiple Cellular Events, Interacts Physically With BRCA1 in the Nucleus of Living Cells", DNA and Cell Biology, May 2000, 19(5), 253-263.

Zuckermann, "The Chemical Synthesis of Peptidomimetic Libraries", Current Opinion in Structural Biology, Aug. 1993, 3(4), 580-584.

Zutshi et al., "Inhibiting the Assembly of Protein-Protein Interfaces", Current Opinion in Chemical Biology, Feb. 1998, 2(1), 62-66.

* cited by examiner

| 1c, 2c, 3c | Buffer + (ErbB3 + HRGβ1) |
| 1b, 2b, 3b | Peptide + (ErbB3 + HRGβ1) |
| 1a, 1b, 1c | Buffer + ErbB3 |

1 B2-S23-BPT
2 B2-S22-APE
3 B1-S22-ALG
4 B3-S22-APQ
5 B4-S22-AFD
6 B2-S22-AFA
7 CD4-G

A

| HRGβ1 | - | + | + | + | + |
| B2-S22-AFA | - | - | + | - | - |
| B3-S22-APQ | - | - | - | + | - |
| CD4-G | - | - | - | - | + |

B

B2-S22-AFA (μg/ml)   0.1   0.5   2.0

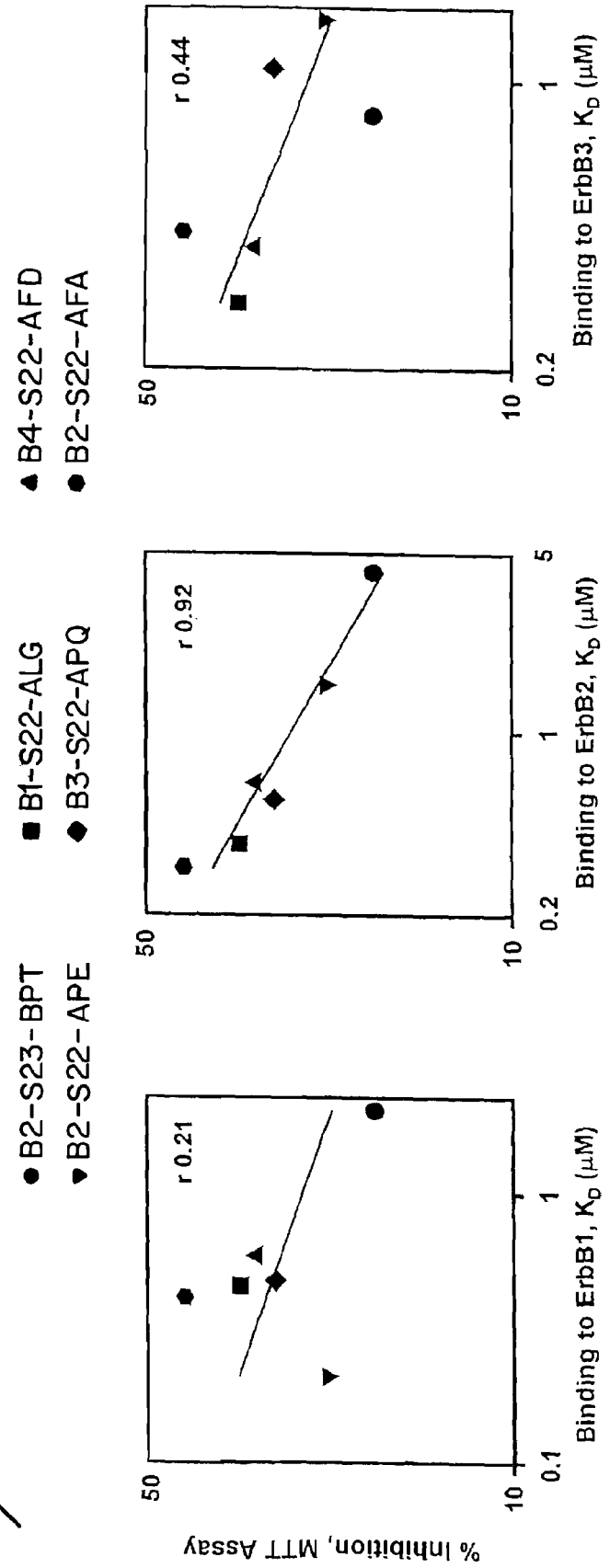

Monomer A    Monomer B    Dimer

Monomer A    Monomer B    Dimer

ERBB INTERFACE PEPTIDOMIMETICS AND METHODS OF USE THEREOF

CROSS-REFERENCE TO RELATED APPLICATIONS

The present application is a divisional of co-pending application Ser. No. 12/625,706, filed Nov. 25, 2009, which in turn is a divisional of application Ser. No. 10/119,288, filed Apr. 8, 2002, now U.S. Pat. No. 7,638,598, which in turn claims priority benefit of Provisional Application No. 60/282,037, filed Apr. 6, 2001, and Provisional Application No. 60/309,864, filed Aug. 3, 2001. Each of these prior applications is incorporated by reference herein in its entirety.

FIELD OF INVENTION

The present invention is directed to treatments and diagnoses for mammalian tumors. More particularly this invention is directed to methods of preventing, treating, and diagnosing mammalian cancer tumors using mimetics and antibodies.

BACKGROUND

Members of the c-erbB (erbB) family of receptor tyrosine kinase genes, including epidermal growth factor receptor c-erbB1 (EGFr, HER1), c-erbB2 (HER2, neu, p185), c-erbB-3 (HER3), and c-erbB-4 (HER4), are known to be oncogenes that encode cell surface receptor proteins. The receptors, under some circumstances, display abnormal kinase activities that contribute to cell proliferation and transformation.

ErbB family receptor tyrosine kinases (RTKs) form homodimeric, heterodimeric, or perhaps oligomeric complexes that are catalytically active and, thereby, couple extracellular signals with alterations of cellular growth and differentiation status. Their ligands and subsequent receptor-mediated signaling have been implicated in survival, proliferation and differentiation in a variety of cell types (reviewed in Dougall et al. 1994; O'Rourke, et al. 1997; Pinkas-Kramarski, et al. 1997; Tzahar and Yarden 1998).

All members of the erbB family share structural features, including an extracellular ligand-binding domain that contains four subdomains, including two cysteine-rich subdomains, a single amphipathic transmembrane domain, and an intracellular kinase domain. The kinase domain shows the highest degree of amino acid sequence similarity (about 80%) among members of this family.

Overexpression of erbB receptors has been found in many types of human cancer, raising the possibility that receptor-linked therapies may be useful as cancer management strategies. EGFr (erbB1) is the most extensively studied member in this family. The EGFr gene is amplified and rearranged in many human brain tumors of glial origin and in some cell lines. Ullrich et al, has found the gene for the EGFr cellular analogue of the avian vital oncogene v-erb-B. (Ullrich et al, Nature, Vol. 309, pp. 418-425, 1984). The EGFr receptor is a transmembrane glycoprotein of about 170 kDa (Cohen, J. Biol. Chem., Vol. 258, pp. 1523-1531, 1982). Overexpression of the EGFr has been found in a variety of tumors, including bladder, esophagus, lung, glioblastoma and breast. In breast cancers, over 40% of the tumors are EGFr positive, and EGFr levels negatively correlate with steroid receptor (estrogen receptor and progesterone receptor) levels. The EGF-receptor exists in two kinetic forms (low affinity and high-affinity receptors) that may be inter-convertible. (Fernandez-Pol, Biol. Chem., Vol. 260, pp 5003-5011, 1985.) Expression of EGF-receptors has been implicated in the progression of tumor growth. In addition, an association has been detected between late stages of melanoma development and extra copies of the chromosome carrying the EGFr gene. (Koprowski et al., Somatic Cell and Molecular Genetics, Vol. 11, pp. 297-302, 1985.)

A variety of strategies have also been developed for targeting the erbB1 receptor including monoclonal antibodies, ligand-linked immunotoxins, tyrosine kinase inhibitors, and antisense approaches. (Zhang et al., 2000.) Of all the members of the erbB family, erbB2 is the most correlated to breast cancer, ovarian cancer and pancreatic cancer. Initially identified in rat neuroglioblastomas induced by a carcinogen ethylnitrosourea, neu (also known as her2/erbB2) is a proto-oncogene encoding a 185 kDa receptor-tyrosine-kinase which is highly homologous with, but distinct from, EGFr. The translation product of the erbB-2 oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that p185 forms homodimers with other p185 molecules or heterodimers with epidermal growth factor receptor EGFR (erbB1) and that these dimers exhibit elevated tyrosine kinase activity, which brings about the transformed phenotype in cells having such dimers.

Amplification of the erbB2 gene, the human homologue of neu, and subsequent overexpression of the polypeptide product p185 has been identified in 25-30% of primary breast and ovarian cancers, although no oncogenic point mutation has been detected in erbB2 associated with human carcinomas. In murine fibroblasts NIH3T3 and NR6, overexpression of erbB2 results in transformation, indicating that oncogenic mutation is not necessary for erbB2. Previous work has shown that overexpression of erbB2/neu can lead to oligomers which have enhanced kinase activity.

Overexpression of the erbB2 gene in human breast cancer is also associated with a poor prognosis and resistance to hormonal treatment and chemotherapy. Advanced stages of malignancy, characterized by large tumor size and increased number of positive lymph nodes as well as reduced survival time and decreased time to relapse, was directly correlated with an increased level of amplification of the neu gene. The neu protooncogene is expressed at low levels in normal human tissues.

c-erbB3 is expressed in a variety of normal tissues of ephithelial origin and is overexpressed in a subset of human mammary tumors. c-erbB4 (erbB3) is most predominantly expressed in several breast carcinoma cell lines and also in normal skeletal muscle, heart, pituitary, and cerebellum. The erbB3 receptor has only limited kinase activity. Overexpression of the erbB3 or erbB4 alone cannot transform NIH3T3 cells, even in the presence of ligand. It is suggested that the contribution of erbB3 and erbB4 to tumorigenicity depends on heterodimerization with the EGFr or erbB2.

Monoclonal antibodies (mAbs) and fragments from them have been used clinically for the diagnosis and treatment of many different human diseases (Dougall et al 1994, Oncogene 2109-23). The anti-tumor efficacy of mAbs not only requires specificity towards tumor antigens which show enhanced expression in neoplastic tissue, but also must demonstrate the desired biological effect, namely, the inhibition of tumor growth. U.S. Pat. No. 4,522,918, e.g., discloses a cancer treatment using monoclonal antibodies directed at surface antigens of human mammary adenocarcinoma cells.

Capone et al., JNCI 72: 673-677, (1984), investigated the relationship between antigen density and immunotherapeutic response elicited by monoclonal antibodies against solid tumors. These investigators used monoclonal antibodies specific against human breast cancer. It was found that passively administered monoclonal antibody can be effective in producing a tumor regression response against solid tumors. Tumoricidal response with monoclonal antibody appeared to be exponentially related to the density of the antigen on the cells. U.S. Pat. No. 6,252,050 describes methods for generating cross-reactive antibodies. Antibodies against p185 and methods of using such antibodies are described in U.S. Pat. Nos. 6,165,464, 5,772,997, 5,770,195, 5,725,856, 5,720,954, and 5,677,171, which are incorporated herein by reference. U.S. Pat. No. 5,705,157 describes antibodies against EGFR. U.S. Pat. No. 5,470,571 discloses a cancer treatment using monoclonal antibodies directed at the EGFr generated from the A431 carcinoma cell line. Each of the aforementioned U.S. patents is hereby incorporated herein by reference in its entirety.

In the case of receptor-dimerization, a construct containing the extracellular domain plus the transmembrane domain of p185 was able to initiate the p185-EGFr dimerization (Qian et al, PNAS 91, 1500, 1994). Later, an alternative transcript product of p185 with only subdomain I and II was found to be able to dimerize with p185 (Doherty et al. PNAS 1999, 96, 10869).

An approach for disabling receptor activity is to target protein-protein interactions involved in receptor functioning. Since protein-protein interactions play a key role in various mechanisms of cellular growth and differentiation, and viral replication, inhibition of these interactions is a promising novel approach for rational drug design against a wide number of cellular and viral targets (Zutshi et al., *Curr Opin Chem Biol* 1998, 2, 62-66; Peczuh et al., *Chem. Rev.* 2000, 100, 2479-2494). Binding of polypeptide hormones, growth factors or cytokines to cell-surface receptors activates dimerization (oligomerization) of the receptors which leads to the signal transduction to the interior of the cell (Heldin, *Cell* 1995, 80, 213-223). While most of the receptor inhibitors developed to date have been focused on the blockade of receptor-ligand or enzyme-substrate interactions, repression of receptor-receptor interactions that accompany oligomerization also represents an important objective for disabling receptor functioning.

Although ligand-induced homo- and heterodimerization of the full-length native erbB receptors has been established and well documented, experimental data on self-associations of the extracellular domains of these receptors is somewhat contradictory. In analytical ultra centrifugation and MALLS studies, ligand-induced homodimerization has been demonstrated for erbB1 and erbB4 (Ferguson et al., EMBO J 2000, 19, 4632-4643). However, no homo-oligomerization could be observed for the erbB3 receptor and the only erbB receptor combinations that produced heterodimers in the presence of HRGβ1 were erbB2/erbB4 and to a smaller extent erbB2/erbB3. In contrast, both erbB3 homodimerization and erbB3/erbB2 heterodimerization have been reported for the ectodomains, but these effects could only be observed when ectodomains of the receptors were anchored to the membrane (Tzahar et al., EMBO J 1997, 16, 4938-4950). Landgraf and Eisenberg have reported ligand-independent self-association of erbB3 ectodomains that could be disrupted by HRGβ1 (Landgraf et al., Biochemistry 2000, 39, 8503-8511). Both monomeric and oligomeric forms of erbB3 were detected in the presence of HRGβ1 by size-exclusion chromatography. Addition of the ligand produced a shift toward a low-molecular mass species.

The present inventors have identified distinct extracellular subdomains of erbB2 that are involved in heterodimerization with erbB1 (Kumagai et al, Proc Natl Acad Sci USA 2001, 98, 5526-5531). Peptidomimetics against subdomain IV alter the heteromeric signaling and transforming activities induced by EGF after associating with EGFR. Peptidometics and antibodies that target subdomain IV are therefore useful as therapeutic agents against erbB-expressing tumors.

SUMMARY

Certain embodiments of the present invention relate to antibodies which bind to assembly epitopes of erbB1, erbB2, erbB3, erbB4 and assembly epitopes of TNF receptors.

Certain embodiments of the present invention relate to antibodies which block the oligomerization of receptors. In some preferred embodiments, the antibodies are induced by immunizing with a peptide or protein subdomain containing structural elements involved in the oligomerization. In some embodiments, the structural element is a cystine knot.

Certain embodiments of the present invention relate to antibodies which bind to subdomains of erbB1, erbB2, erbB3, erbB4, TNF receptors, or members of the IgSF, or assemblies thereof, that contain cystine knots.

Certain embodiments of the present invention relate to antibodies which bind to cystine knots of erbB1, erbB2, erbB3, and erbB4, or to cystine knots of TNF receptors.

Certain embodiments of the present invention relate to pharmaceutical compositions comprising which binds to erbB receptors or to TNF receptors. Some embodiments relate to injectable pharmaceuticals which are sterile and pyrogen free.

Certain embodiments of the present invention relate to antibodies which bind to interaction surfaces in the extracellular domains of erbB receptors or to interaction surfaces in the extracellular domains of TNF receptors.

Certain embodiments of the present invention relate to peptides which mimic erbB receptors or TNF receptors. In some preferred embodiments, the peptides mimic an extracellular domain of an erbB receptor or of an extracellular domain of a TNF receptor. In more preferred embodiments, the peptides mimic subdomain IV of the erbB receptor. In even more preferred embodiments, the peptides mimic the S22 or S23 loop of the erbB receptor.

Certain embodiments of the present invention relate to mimetics of erbB receptors or TNF receptors. In some preferred embodiments, the mimetic is a mimetic of an extracellular domain of an erbB receptor or of an extracellular domain of a TNF receptor. In more preferred embodiments, the mimetic is a mimetic of subdomain IV of the erbB receptor. In even more preferred embodiments, the mimetic is a mimetic of the S22 or S23 loop of the erbB receptor.

Certain embodiments of the present invention relate to pharmaceutical compositions comprising peptides or mimetics of erbB receptors or TNF receptors, in combination with anti-cancer drugs. Some such embodiments are injectable pharmaceuticals which are sterile and pyrogen free.

Certain embodiments of the present invention relate to methods of treating human patients having solid tumors by administering to the patient peptides or mimetics of or antibodies to erbB receptors. In some such embodiments the administration of peptides, mimetics or antibodies may optionally be followed by exposing the patient to a therapeutically effective amount of anti-cancer radiation. In some other embodiments, the administration of peptides, mimetics, or antibodies is performed in combination with administration of a therapeutically effective amount of a chemotherapeutic agent. In some embodiments the administration of peptides, mimetics or antibodies is performed in combination with administration of a therapeutically effective amount of a chemotherapeutic agent and followed by exposing the patient to a therapeutically effective amount of anti-cancer radiation.

Certain embodiments of the present invention relate to methods of treating human patients having solid tumors by administering to the patient peptides or mimetics of erbB receptors that are conjugated to radioactive, chemotherapeutic, or photodynamic therapeutic agents.

Certain embodiments of the present invention relate to pharmaceutical compositions comprising antibodies which bind to erbB or TNF receptors that are conjugated to radioactive or chemotherapeutic agents. Some embodiments relate to injectable pharmaceuticals which are sterile and pyrogen free.

Certain embodiments of the present invention relate to methods of preventing tumors in human patients by administering to the patient anti-erbB antibodies.

Certain embodiments of the present invention relate to methods of preventing tumors in human patients by administering to the patient peptide or mimetics of erbB receptors.

Certain embodiments of the present invention relate to methods of imaging erbB tumors in human patients having such tumors using detectable anti-erbB antibodies.

Certain embodiments of the present invention relate to pharmaceutical compositions comprising detectable antibodies which bind to erbB receptors, to TNF receptor, or to members of the IgSF. Some embodiments relate to injectable pharmaceuticals which are sterile and pyrogen free.

Certain embodiments of the present invention relate to diagnostic kits and to methods for imaging and/or detecting solid tumors using anti-erbB antibodies.

Certain embodiments of the present invention relate to a method of preventing tumors in a mammal which comprises administering to said mammal an agent selected from the group consisting of a peptide consisting essentially of an erbB subdomain IV, a peptide consisting essentially of an erbB subdomain IV peptide wherein between 1-10 amino amino acids of the subdomain have been substituted with a conservative amino acid, and a peptide consisting essentially of between 10-25 contiguous amino acids of a an erbB subdomain IV.

Certain embodiments of the present invention relate to a vaccine for preventing tumors in a mammal which comprises an active agent selected from the group consisting of a peptide consisting essentially of an erbB subdomain IV, a peptide consisting essentially of an erbB subdomain IV peptide wherein between 1-10 amino amino acids of the subdomain have been substituted with a conservative amino acid, and a peptide consisting essentially of between 10-25 contiguous amino acids of a an erbB subdomain IV and an adjuvant.

BRIEF DESCRIPTION OF THE DRAWINGS

FIG. 1A depicts the schematic representation of the expression vectors. FIG. 1B depicts heterodimer formation between EGFr and Neu mutants.

FIG. 7A-B. Correlation between receptor-binding properties of the erbB peptides and their biological activity against erbB2-overexpressing T6-17 cells. Plots show correlation between peptides' activities in MTT assays and (A) their receptor binding affinities, or (B) their inhibitory activity against erbB receptor oligomerization.

DETAILED DESCRIPTION OF ILLUSTRATIVE EMBODIMENTS

Figure 1A:
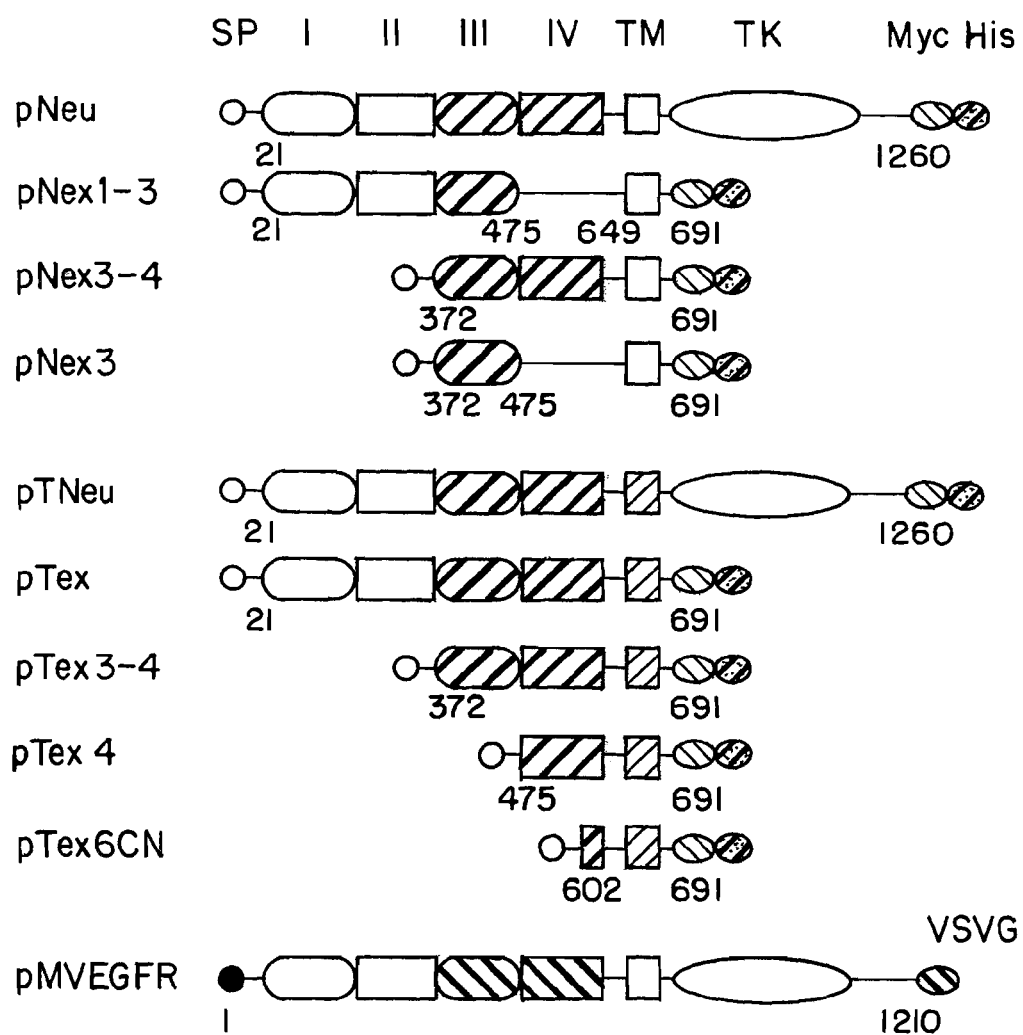
FIG. 1A-B represents the schematic representation of the expression vectors and heterodimer formation between EGFr and Neu mutants.

In some embodiments, of the present invention compositions comprising peptides and mimetics of and antibodies to regions of receptors which facilitate oligomerization are provided, preferably directed to regions of receptors comprising one or more cystine knots. The present invention further provides methods for treatment, diagnosis, and imaging of mammalian tumors using such peptides and antibodies.

Definitions

As used herein, the term "erbB" refers to receptors in the erbB family of receptor tyrosine kinases which assemble into hetero- or homodimers, including, but not limited to, erbB1 (EGFr—epidermal growth factor receptor, HER1), erbB2 (neu, p185, HER2), erbB3 (HER3), and erbB4 (HER4).

As used herein, the term "TNF" refers to receptors that bind tumor necrosis factor-like ligomers which assemble into oligomers. TNF receptors include, but are not limited to, TNF, FAS, RANK, TRAIL, and CD40.

As used herein, the terms "p185/EGFr cancer", "p185/EGFr tumors", "erbB2/EGFr cancer" and "erbB2/EGFr tumors" are meant to refer to tumor cells and neoplasms which express erbB2 and EGFr. erbB2/EGFr tumors have p185 and EGF receptors on their cell surfaces.

As used herein, the terms "erbB tumor", and "erbB cancer" are meant to refer to tumor cells and neoplasms which express one or more erbB receptors. Some erbB tumor cells or neoplasms may express p185 receptors on their cell surfaces.

As used herein, the terms "TNF", and "TNF-related pathologies" are meant to refer to pathologies that involve one or more TNF family receptors.

As used herein, the term "oligomerization" refers to the process by which assemblies of monomers are formed into multimers. Examples of assemblies formed through this process include but are not limited to dimers, trimers and tetramers, etc. Such assemblies may comprise two or more identical monomers yielding a homodimer, homotrimer, homotetramer, etc., or two or more different monomers yielding a heterodimer, heterodimer, heterotrimer, etc.

As used herein, the term "antibody" is meant to refer to antibodies, as well as antibody fragments such as FAb and F(Ab)$_2$ fragments, recombinant antibodies or recombinant antibody fragments. Antibodies may, in some preferred embodiments, be monoclonal, humanized, primatized, or chimeric antibodies.

As used herein, the term "cystine knot" refers to a polypeptide formed by at least two disulfide bonds and the protein chains linking them, penetrated by a third disulfide bond and is further described in Murzin et al., J. Mol. Biol. 247: 536-540, which is incorporated by reference in its entirety. For example, in the TNF receptor family a cystine knot consists of 42 amino acid residues with 6 cysteine residues forming 3 inter-chain disulfide bonds to create the structural motif.

As used herein, the phrase "cystine knot specific antibody" refers to an antibody which binds to a cysteine-rich domain, a cystine knot, or a portion of a cystine knot loop. In some embodiments, the antibody binds to cysteine bonded loops found within a cysteine rich domain.

As used herein, the phrase "cystine knot comprising region" refers to a portion of a receptor that comprises one or more cystine knots. In some embodiments, the cystine knot-comprising region is an extracellular portion of the receptor. In some preferred embodiments, the cystine knot comprising region is subdomain IV. In more preferred embodiments, the cystine knot comprising region is selected from the group consisting of the S22 loop and the S23 loop.

As used herein, the term "region" refers to a part of a receptor comprising at least one portion. Representative receptor regions include, but are not limited to, extracellular regions, transmembrane regions, and intracellular regions.

As used herein, the term "portion" refers to at least 3-5 amino acids, more preferably at least 8-10 amino acids, more preferably at least 11-15 amino acids, more preferably at least 17-24 amino acids, and even more preferably at least 25-30 amino acids, and most preferably at least 30-45 amino acids.

As used herein, the term "conformation site" refers to a site on a receptor which affects the conformation of the receptor. In some embodiments, binding of an antibody, peptide or mimetic to the conformation site changes the conformation of the receptor such that oligomerization of the receptor is prevented and, preferably, reduces or eliminates receptor signaling. In some preferred embodiments, the conformation site is a receptor-receptor contact point.

As used herein, the term "mimetic" is used to refer to compounds which mimic the activity of peptide. Mimetics are non-peptides but may comprise amino acids linked by non-peptide bonds. U.S. Pat. No. 5,637,677 and its parent applications contain detailed guidance on the production of mimetics. Briefly, the three dimensional structure of the peptides which specifically interacts with the three dimensional structure of erbB receptors is duplicated by a molecule that is not a peptide.

As used herein, the terms "conformationally restricted peptides", "constrained peptides" and "conformationally constrained peptides" are used interchangeably and are meant to refer to peptides which, for example through intramolecular bonds, are conformationally stable and remain in a sufficiently restricted conformation. The compounds have an affinity to erbB receptors and, when bound to erbB receptors on cells, have a biologically active effect on cells that have a erbB-mediated transformation phenotype.

As used herein, the terms "aromatic amino acids" and "aromatic amino acid residues" used interchangeably are meant to refer to phenylalanine and tyrosine.

As used herein, the term "exocyclic amino acid residue" is meant to refer to amino acid residues which are linked to cyclicized peptide but which are not within the portion of the peptide that makes up the circularized structure.

As used herein, the term "exocyclic portions" is meant to refer to an amino acid sequence having one or more amino acid residues which are linked to cyclicized peptide but which are not within the portion of the peptide that makes up the circularized structure.

As used herein, the term "linking moiety" is meant to refer to a molecular component or functional group which is capable of forming bonds with three amino acids.

As used herein, the term "linking amino acid residue" is meant to refer to an amino acid residue that is a linking moiety.

As used herein, the terms "active sequence" and "active region" are used interchangeably and are meant to refer to the amino acid sequence of the portion of a compound of the invention that is directly interacts with an erbB receptor, wherein the interaction is characterized by an affinity between the active portion and an erbB receptor.

In some embodiments, the peptides and mimetics are constrained mimics of the loops or repeats present in subdomain IV of erbB receptors. In some embodiments, the peptides and mimetics mimic a cystine knot comprising region, preferably a cystine knot or portion thereof. In some embodiments, binding of a peptide or mimetic to an erbB or TNF receptor prevents dimerization of the receptor, and, preferably, reduces or eliminates receptor signaling.

As used herein, the term "dimerization site" is used interchangeably with the terms "interaction site" and "interaction surface" and refers to a site on a receptor that forms a bond with another receptor when the two receptors dimerize. In some embodiments, the dimerization site is ligand-independent, i.e., the dimerization site is not dependent on the presence or absence of a particular bound ligand. In other embodiments, the dimerization site is ligand-dependent, i.e., the dimerization site is dependent on the presence or absence of a particular bound ligand. In some embodiments, binding of an antibody, peptide or mimetic to the dimerization site prevents dimerization of the receptors and, preferably, reduces or eliminates receptor signaling. In some preferred embodiments, the dimerization site is subdomain IV of the erbB receptor or a portion thereof.

As used herein, the term "assembly" is used interchangeably with "ensemble" or "dimer" and refers to homo- or heterooligomers of receptors. Such assemblies may comprise erbB1, erbB2, erbB3, erbB4, or combinations thereof, or receptors in the TNF family of receptors, including but not limited to FAS, RANK, TRAIL, and CD40, or combinations thereof, or members of the IgSF superfamily, including but not limited to ICOS and CD28.

As used herein, the term "high risk individual" is meant to refer to an individual who has had an erbB or TNF related pathology or pathologies associated with IgSF members either removed or in remission, and who is therefore susceptible to a relapse or recurrence. In the case of erbB, as part of a treatment regimen for a high risk individual, the individual can be prophylactically treated against tumors that they have been diagnosed as having had in order to combat a recurrence. Thus, once it is known that an individual has had an erbB-cancer, the individual can be treated according to the present invention to prevent normal cells from transforming into tumor cells.

As used herein, the term "in combination with" is meant to refer to administration of the antibody, peptide or mimetic compositions of the invention with radiation therapy and/or chemotherapy. Administration of the antibody, peptide or mimetic compositions may take place prior to, simultaneously with, or after radiation therapy and/or chemotherapy.

As used herein, the term "therapeutically effective amount" is meant to refer to an amount of an antibody, peptide or mimetic which produces a medicinal effect observed as reduction or reverse in tumorigenic phenotype of tumor cells in an individual when a therapeutically effective amount of a antibody is administered to the individual. Therapeutically effective amounts are typically determined by the effect they have compared to the effect observed when a composition which includes no active ingredient is administered to a similarly situated individual.

As used herein, the term "preventing the development of tumors" is meant to refer to preventing the transformation of normal cells into tumor cells including inhibiting the transformation of cells that have a normal or incomplete transformed phenotype into fully transformed phenotype. Thus, the development of tumors refers to the transformation event which results in the acquisition of a transformed phenotype. According to some aspects of the present invention, antibodies, peptides or mimetics may be administered to individuals who are at risk of developing tumors. The prophylactic administration of an antibody, peptide or mimetics to high-risk individuals results in the prevention of the transformation event occurring. Cells having the normal phenotype are not converted to the cells having transformed phenotype. The antibodies, peptides, or mimetics prevent tumors before they are formed by preventing a normal cell from becoming a cancer cell.

As used herein, the term "prophylactically effective amount" is meant to refer to an amount of an antibody, peptide, or mimetic which produces a medicinal effect observed as the prevention of non-transformed cells from becoming transformed in an individual when a prophylactically effective amount of an antibody, peptide or mimetic is administered to an individual. Prophylactically effective amounts are typically determined by the effect they have compared to the effect observed when a composition which includes no active ingredient is administered to a similarly situated individual.

As used herein, the phrase "injectable pharmaceutical composition", or variants thereof, refers to pharmaceutical compositions which satisfy the USP requirements for "injectables", i.e., sterile, pyrogen- and particulate free, and possessing specific pH and isotonicity values.

Antibodies

In addition to molecules designed from assembly epitopes of erbB1, erbB2, erbB3 erbB4, and assembly epitopes of TNF or IgSF receptors, the present invention comprises molecules, including but not limited to antibodies and peptide mimetics, based on interacting surfaces of receptors.

In some embodiments, antibodies are specific to dimerization sites of erbB, TNF, or IgSF receptors. In some embodiments, antibodies are specific to a dimerization site of erbB1 or erbB2. Binding of the antibody to the dimerization site may prevent the dimerization of the receptor, and, preferably, reduces or eliminates receptor signaling.

In some embodiments, antibodies are specific to conformation sites of erbB, TNF, or IgSF receptors. In a preferred embodiment, antibodies are specific to a conformation site of erbB1 or erbB2. In some embodiments, antibodies are specific to a conformation site of erbB1 or erbB2. Binding of the antibody to the conformation site changes the conformation of the receptor such that the receptor is not able to dimerize, and, preferably, reduces or eliminates receptor signaling.

In some embodiments, antibodies are provided which bind to cystine knot comprising regions or cystine knots or portions thereof of erbB, TNF, or IgSF receptors. In some embodiments, antibodies are specific for cystine knot in an extracellular domain of an erbB, TNF, or IgSF receptor.

Peptides, Mimetics and Antibodies

The present invention describes inter alia the biochemical consequences of peptides mimetics which are capable of disabling the assembly of erbB receptor polypeptides or TNF receptor polypeptides by different mechanisms.

The present invention relates, inter alia, to constrained peptides that contain exocyclic portions including exocyclic amino acids that are aromatic amino acids as well as an active region which specifically binds to erbB. Examples of constrained peptides are found in U.S. Pat. No. 6,100,377.

The present invention also relates to mimetics which specifically bind to erbB.

The present invention is useful to therapeutically treat an individual identified as suffering from erbB tumors in order to reverse the transformed phenotype of the tumor cells. The present invention is useful to prophylactically treat an individual who is predisposed to develop an erbB tumors or who has had erbB-associated tumors and is therefore susceptible to a relapse or recurrence. The present invention is useful to detectably image tumors with respect to erbB receptors on their surfaces. The present invention is useful to detect and quantify erbB on all surfaces.

According to some embodiments, the present invention provides peptides having the formula:

$$R_1\text{-}R_2\text{-}R_3\text{-}R_4\text{-}R_5\text{-}R_6\text{-}R_7$$

wherein:

$R_1$ is 1-6 amino acid residues, at least one of which is tyrosine or phenylalanine;

$R_2$ is a linking moiety which bonds with $R_1$, $R_3$ and $R_6$ such that a portion of said peptide is cyclicized;

$R_3$ is 0-20 amino acids;

$R_4$ is 6-12 amino acids;

$R_5$ is 0-20 amino acids;

$R_6$ is a linking moiety which bonds with $R_5$, $R_7$ and $R_2$ such that a portion of said peptide is cyclicized;

$R_7$ is 1-6 amino acid residues, at least one of which is tyrosine or phenylalanine;

wherein: $R_1$, $R_2$, $R_3$, $R_4$, $R_5$, $R_6$ and $R_7$, taken together, are 30 amino acids or less.

In some embodiments, $R_4$ comprises F-P-D-E-E-G-A (SEQ ID NO:1). In some embodiments, $R_4$ consists of F-P-D-E-E-G-A (SEQ ID NO:1). In some embodiments, $R_4$ comprises F-Y-P-D-E-E-G-A (SEQ ID NO:2). In some embodiments, $R_4$ consists of F-Y-P-D-E-E-G-A (SEQ ID NO:2).

The primary function of $R_1$ in compounds of the present invention arises from the presence of at least one amino acid that contains an aromatic group: i.e. the presence of tyrosine or phenylalanine. The presence of the aromatic amino acid at position $R_1$ results in an increase affinity of the peptide to erbB and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_1$ are disclosed in co-pending U.S. Pat. No. 6,100,377. In some embodiments, the additional amino acids are present as a site for linkage to detectable labels or moieties. In some embodiments, the additional amino acids are present as a site for dimerization with other peptides; either for formation of homodimers with each other or heterodimers with other peptides.

In some preferred embodiments, $R_1$ is 1-5 amino acids. In some preferred embodiments, $R_1$ is 4 amino acids. In some preferred embodiments, $R_1$ is 3 amino acids. In some preferred embodiments, $R_1$ is 2 amino acids. In some preferred embodiments, $R_1$ is 1 amino acid. In some preferred embodiments, $R_1$ comprises S-Y. In some preferred embodiments, $R_1$ consists of S-Y. In some preferred embodiments, $R_1$ comprises G-S-Y. In some preferred embodiments, $R_1$ consists of G-S-Y. In some preferred embodiments, $R_1$ consists of Y. In some preferred embodiments, $R_1$ consists of K. In some preferred embodiments, $R_1$ comprises K. Other examples of $R_1$ include G-G-S-Y (SEQ ID NO:21) and G-G-G-S-Y (SEQ ID NO:22). Contemplated equivalents include aromatic functional groups at $R_1$ which are not part of tyrosine or phenylalanine.

The function of $R_2$ is to form bonds with $R_1$ as well as to form bonds with $R_6$ which cyclicize or otherwise conformationally restrict the molecule. Bonds between $R_2$ and $R_6$ cyclicize the molecule and thereby maintain $R_3$-$R_4$-$R_5$, and, specifically $R_4$, in a constrained conformation that produces the specific biologically active surface that has an affinity for and interacts with erbB. Further, in such an arrangement $R_1$ becomes an exocyclic portion of the peptide. Accordingly, $R_2$ may be any moiety capable of forming bonds with $R_6$ as well as $R_1$ and $R_3$.

$R_2$ is preferably an amino acid residue, preferably cysteine. When both $R_2$ and $R_6$ are cysteine, the disulfide bonds form between the two cysteines cyclicize the molecule. It is contemplated that $R_2$ may any moiety that, together with $R_6$, will allow for the cyclization of the portion of the molecule that includes $R_1$-$R_2$-$R_3$-$R_4$-$R_5$-$R_6$ while rendering $R_1$ and $R_7$ exocyclic portions of the peptide. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers,* 33:1037-1049; Wood, et al., (1992) *J. Pep. Prot. Res.,* 39:533-539; Saragovi, et al., (1992) *Immunomethods,* 1:5-9; Saragovi, et al., (1991) *Science,* 253:792-795; Manning, et al., (1993) *Reg. Peptides,* 45:279-283; Hruby, (1993) *Biopolymers,* 33:1073-1082; Bach, et al., (1994) *New Adv. Peptidomimetics Small Mol. Design,* I:1-26; and Matsuyama, et al., (1992) *J. Bacteriol.,* 174:1769-1776, each of which are incorporated herein by reference.

The function of $R_3$ is to serve as a spacer and provide structure to present the active region in proper conformation. In some embodiments, the cyclization of the active region by particular linking moieties results in the proper folding of the active region to place it in active conformation and no $R_3$ is required. In some embodiments, the cyclization of the active region by particular linking moieties requires additional spacing and turns to facilitate that proper folding of the active region in order to place it in active conformation. In such embodiments, amino acid residues or sequences may be provided at $R_3$. In some preferred embodiments, $R_3$ is 0-10 amino acids. In some preferred embodiments, $R_3$ is 0-5 amino acids. In some preferred embodiments, $R_3$ is 0 amino acids.

$R_4$ is the active region of the compounds according to this aspect of the invention. In compounds of the invention, the functional groups of the active region are in a conformation which places them in a particular three dimensional arrangement that allows them to interact with the amino acids and functional groups thereon of an erbB receptor and to bind to an erbB receptor through such interactions. In peptide mimetics, the functional groups are provided in the active three-dimensional arrangement but are connected to modified or different backbones. It is possible to vary each residue with one that contributes equivalent bulk and hydrophobic moment and that still permits hydrogen bonding to surrounding water molecules or to residues to which the compound attaches.

The function of $R_5$ is to present the active region in proper conformation. In some embodiments, the cyclization of the active region by particular linking moieties results in the proper folding of the active region to place it in active conformation and no $R_5$ is required. In some embodiments, the cyclization of the active region by particular linking moieties requires additional spacing and turns to facilitate that proper folding of the active region in order to place it in active conformation. In such embodiments, amino acid residues or sequences may be provided at $R_5$. In some preferred embodiments, $R_5$ is 0-10 amino acids. In some preferred embodiments, $R_5$ is 0-5 amino acids. In some preferred embodiments, $R_5$ is 0 amino acids.

The function of $R_6$ is to form bonds with $R_2$ which cyclicize or otherwise conformationally restrict the molecule. Bonds between $R_6$ and $R_2$ cyclicize the molecule and thereby maintain $R_3$-$R_4$-$R_5$, and, specifically $R_4$, in a constrained conformation that produces the specific biologically active surface that has an affinity for and interacts with erbB. Accordingly, $R_6$ may be any moiety capable of forming bonds with $R_2$ as well as $R_5$ and $R_7$. $R_6$ is preferably an amino acid residue, preferably cysteine. When both $R_6$ and $R_2$ are cysteine, disulfide bonds formed between the two cysteines cyclicize the molecule. It is contemplated that $R_6$ may any moiety that, together with $R_2$, will allow for the cyclization of the molecule. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers,* 33:1037-1049; Wood, et al., (1992) *J. Pep. Prot. Res.,* 39:533-539; Saragovi, et al., (1992) *Immunomethods,* 1:5-9; Saragovi, et al., (1991) *Science,* 253:792-795; Manning, et al., (1993) *Reg. Peptides,* 45:279-283; Hruby, (1993) *Biopolymers,* 33:1073-1082; Bach, et al., (1994) *New Adv. Peptidomimetics Small Mol. Design,* I:1-26; and Matsuyama, et al., (1992) *J. Bacteriol.,* 174:1769-1776, each of which are incorporated herein by reference.

The primary function of $R_7$ in compounds of the present invention arises from the presence of at least one amino acid that contains an aromatic group: i.e. the presence of tyrosine or phenylalanine. The presence of the aromatic amino acid at position $R_7$ results in an increase in the affinity of the peptide to erbB and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_7$ are disclosed in U.S. Pat. No. 6,100,377.

In some embodiments, the additional amino acids are present as a site for linkage to detectable labels or moieties. In some embodiments, the additional amino acids are present as a site for dimerization with other peptides; either for formation of homodimers with each other or heterodimers with other peptides.

In some preferred embodiments, $R_7$ is 1-5 amino acids. In some preferred embodiments, $R_7$ is 4 amino acids. In some preferred embodiments, $R_7$ is 3 amino acids. In some preferred embodiments, $R_7$ is 2 amino acids. In some preferred embodiments, $R_7$ is 1 amino acid. In some preferred embodiments, $R_7$ comprises Y-G-G-S (SEQ ID NO:27). In some preferred embodiments, $R_7$ consists of Y-G-G-S (SEQ ID NO:27). In some preferred embodiments, $R_7$ comprises Y-G-G-G (SEQ ID NO:23). In some preferred embodiments, $R_7$ consists of Y-G-G-G (SEQ ID NO:23). In some preferred embodiments, $R_7$ comprises Y-G-G-G-S (SEQ ID NO:24). In some preferred embodiments, $R_7$ consists of Y-G-G-G-S (SEQ ID NO:24). In some preferred embodiments, $R_7$ comprises Y. In some preferred embodiments, $R_7$ consists of Y. In some preferred embodiments, $R_7$ comprises Y-G-G. In some preferred embodiments, $R_7$ consists of Y-G-G. Another example of $R_7$ is Y-G. Contemplated equivalents include aromatic functional groups at $R_7$ which are not part of tyrosine or phenylalanine.

In some preferred embodiments, $R_1$ and $R_7$ collectively contain both tyrosine and phenylalanine. That is, if $R_1$ comprises tyrosine then $R_7$ comprises phenylalanine and if $R_1$ comprises phenylalanine then $R_7$ comprises tyrosine. In some preferred embodiments, $R_1$ and $R_7$ do not both contain tyrosine or phenylalanine. That is, if $R_1$ comprises tyrosine and not phenylalanine then $R_7$ comprises phenylalanine and not tyrosine and if $R_1$ comprises phenylalanine and not tyrosine then $R_7$ comprises tyrosine and not phenylalanine.

In some preferred embodiments, $R_1, R_2, R_3, R_4, R_5, R_6$ and $R_7$, taken together, are less than 30 amino acids. In some preferred embodiments, $R_1, R_2, R_3, R_4, R_5, R_6$ and $R_7$, taken together, are 20 amino acids or less. In some preferred embodiments, $R_1, R_2, R_3, R_4, R_5, R_6$ and $R_7$, taken together, are less than 20 amino acids. In some preferred embodiments, $R_1, R_2, R_3, R_4, R_5, R_6$ and $R_7$, taken together, are 15 amino acids. In some preferred embodiments, $R_1, R_2, R_3, R_4, R_5, R_6$ and $R_7$, taken together, are less than 15 amino acids. In some preferred embodiments, $R_1, R_2, R_3, R_4, R_5, R_6$ and $R_7$, taken together, are 14 amino acids. In some preferred embodiments, $R_1, R_2, R_3, R_4, R_5, R_6$ and $R_7$, taken together, are 13 amino acids. In some preferred embodiments, $R_1, R_2, R_3, R_4, R_5, R_6$ and $R_7$, taken together, are 12 amino acids. In some preferred embodiments, $R_1, R_2, R_3, R_4, R_5, R_6$ and $R_7$, taken together, are 11 amino acids. In some preferred embodiments, $R_1, R_2, R_3, R_4, R_5, R_6$ and $R_7$, taken together, are 10 amino acids.

In certain embodiments $R_1$ is Phe, Tyr, Phe-Glu, or Tyr-Glu; $R_2$ is cysteine or penicillamine; $R_3$ is a bond; $R_4$ is SEQ ID NO:1 or SEQ ID NO:2; $R_5$ is a bond; $R_6$ is cysteine or penicillamine; and $R_7$ is Phe or Tyr.

In certain embodiments, $R_1$ is Phe, Tyr, Phe-Glu, or Tyr-Glu; $R_2$ is cysteine or penicillamine; $R_3$ is a bond; $R_4$ is SEQ ID NO:1; $R_5$ is a bond; $R_6$ is cysteine or penicillamine; and $R_7$ is Phe or Tyr.

In certain embodiments, $R_1$ is Phe, Tyr, Phe-Glu, or Tyr-Glu; $R_2$ is cysteine or penicillamine; $R_3$ is a bond; $R_4$ is SEQ ID NO:2; $R_5$ is a bond; $R_6$ is cysteine or penicillamine; and $R_7$ is Phe or Tyr.

In certain embodiments, $R_1$ is Tyr, Phe-Glu, or Tyr-Glu; $R_2$ is cysteine or penicillamine; $R_3$ is a bond; $R_4$ is SEQ ID NO:2; $R_5$ is a bond; $R_6$ is cysteine or penicillamine; and $R_7$ is Phe or Tyr.

In certain embodiments, the peptide is selected from the group consisting of: Y-C-F-P-D-E-E-G-A-C-Y (SEQ ID NO:3); S-Y-C-F-P-D-E-E-G-A-C-Y (SEQ ID NO:4); G-S-Y-C-F-P-D-E-E-G-A-C-Y (SEQ ID NO:5); G-G-S-Y-C-F-P-D-E-E-G-A-C-Y (SEQ ID NO:6); G-G-G-S-Y-C-F-P-D-E-E-G-A-C-Y (SEQ ID NO:7); Y-C-F-P-D-E-E-G-A-C-Y-G (SEQ ID NO:8); Y-C-F-P-D-E-E-G-A-C-Y-G-G (SEQ ID NO:9); Y-C-F-P-D-E-E-G-A-C-Y-G-G-G (SEQ ID NO:10); Y-C-F-P-D-E-E-G-A-C-Y-G-G-G-S (SEQ ID NO:11); Y-C-F-Y-P-D-E-E-G-A-C-Y (SEQ ID NO:12); S-Y-C-F-Y-P-D-E-E-G-A-C-Y (SEQ ID NO:13); G-S-Y-C-F-Y-P-D-E-E-G-A-C-Y (SEQ ID NO:14); G-G-S-Y-C-F-Y-P-D-E-E-G-A-C-Y (SEQ ID NO:15); G-G-G-S-Y-C-F-Y-P-D-E-E-G-A-C-Y (SEQ ID NO:16); Y-C-F-Y-P-D-E-E-G-A-C-Y-G (SEQ ID NO:17); Y-C-F-Y-P-D-E-E-G-A-C-Y-G-G (SEQ ID NO:18); Y-C-F-Y-P-D-E-E-G-A-C-Y-G-G-G (SEQ ID NO:19); and Y-C-F-Y-P-D-E-E-G-A-C-Y-G-G-G-S (SEQ ID NO:20); YCFPDEEGACYK (SEQ ID NO: 25); and YCFPDEEGACYGGS (SEQ ID NO: 26). Other peptides are included within the scope of the present invention comprising different combinations of $R_1, R_2, R_3, R_4, R_5, R_6$ and $R_7$.

In some embodiments, terminal residues of the peptides are modified. In some embodiments, the terminal residue of $R_1$ is modified with —OH. In some embodiments, the terminal residue of $R_1$ is modified with —NH$_2$. In some embodiments, the terminal residue of $R_7$ is modified with —OH. In some embodiments, the terminal residue of $R_7$ is modified with —NH$_2$.

According to some embodiments, $$R_1\text{-}R_2\text{-}R_3\text{-}R_4\text{-}R_5\text{-}R_6\text{-}R_7$$

together form a peptide wherein:
$R_1$ is 1-3 amino acid residues, at least one of which is tyrosine or phenylalanine;
$R_2$ is cysteine or pencillamine;
$R_3$ is 0 amino acids;
$R_4$ is 7-8 amino acids;
$R_5$ is 0 amino acids;
$R_6$ is cysteine or pencillamine;
$R_7$ is 1-5 amino acid residues, at least one of which is tyrosine or phenylalanine;
wherein:
$R_1, R_2, R_3, R_4, R_5, R_6$ and $R_7$, taken together, are 30 amino acids or less, and wherein $R_1, R_2, R_3, R_4, R_5, R_6$ and $R_7$ are otherwise as set forth above.

In certain embodiments the peptide is B2-S23-BPT: P-C-P-I-N-C-T-H-S-C-V-D-L-D-D-K-G-C-P-A-E-Q-R-A-S-P-L-T-S-I (SEQ ID NO: 38).

In some preferred embodiments of generating antibodies against IgSF members, the peptide is: C-K-V-E-L-M-Y-P-P-P-Y-F-V-G-M-G-N-G-T-Q-I-Y-V-I-D-P-E-P-C (SEQ ID NO: 36).

In some preferred embodiments of generating antibodies against IgSF members, the peptide is: C-K-I-E-F-M-Y-P-P-P-Y-L-D-N-E-R-S-N-G-T-I-I-H-I-K-E-K-H-L-C (SEQ ID NO: 29).

In some preferred embodiments the peptide is: C-S-L-S-I-F-D-P-P-P-F-Q-E-R-N-L-S-G-G-Y-L-H-I-Y-E-S-Q-L-C (SEQ ID NO: 30).

In some preferred embodiments the peptide is B2-S22-APE: Y-C-P-I-W-K-F-P-D-E-E-C-Y (SEQ ID NO: 31).

In some preferred embodiments the peptide is B1-S22-ALG: Y-C-L-V-W-K-Y-A-D-A-G-C-Y (SEQ ID NO: 32).

In some preferred embodiments the peptide is B3-S22-APQ: Y-C-P-1-Y-K-Y-P-D-V-Q-C-Y (SEQ ID NO: 33).

In some preferred embodiments the peptide is B4-S22-AFD: Y-C-F-1-F-K-Y-A-D-P-D-C-Y (SEQ ID NO: 34).

In some preferred embodiments the peptide is B2-S22-AFA: Y-C-F-P-D-E-E-G-A-C-Y (SEQ ID NO: 35).

Those having ordinary skill in the art can readily construct molecules according to the above formulae and determine whether or not the compounds are active as erbB binding compounds which prevent and eliminate the erbB-mediated transformation phenotype.

The peptides of the invention may be dimerized with each other to form homodimers or with other compounds including compounds of the invention to form heterodimers. In preferred dimers, the residues involved in the chemical bound which links the monomers is in the $R_1$ position of the compounds of the invention.

Mimetics of the peptides which mimic erbB, TNF, or IgSF receptors may be produced. Such mimetics may be tested in the assays set forth in the Examples.

According to the present invention, peptides and mimetics that mimic sites on erbB, TNF, or IgSF receptors are useful to prevent dimerization of receptors and thereby down modulate the kinase activity of the receptors. When bound, the peptides and mimetics eliminate or reduce tyrosine kinase activity and/or receptor signaling that results in an elimination or reduction in cell proliferation levels and a non-transformed, quiescent phenotype. The peptides and mimetics are therefore useful in the treatment of individuals suspected of having erbB tumors or TNF and IgSF-mediated pathologies, and in the prevention of such erbB tumor formation. The cells in the individuals that would turn into tumors in an untreated individual do not become fully transformed and do not become tumors in individuals treated by the methods. When administered to individuals who have been identified as being susceptible to or otherwise at risk of developing tumors, the peptides and mimetics may induce antibodies that bind to erbB or TNF monomers, thereby preventing the elevation in tyrosine kinase activity or signaling associated with oligomerization of the receptors. The tyrosine kinase activity in the cell may never become sufficiently elevated and the cell remains non-transformed.

Peptides and mimetics of erbB receptors, TNF or IgSF family receptors are useful in anti-tumor compositions and can be produced by those skilled in the art using readily available starting materials. U.S. Pat. No. 5,637,677 and its parent applications thereof disclose detailed guidance on the production of mimetics.

According to preferred embodiments, a peptide or mimetic is designed based on a known region of an erbB, TNF, or IgSF receptor. In some preferred embodiments, the peptide or mimetic mimics an extracellular domain of an erbB, TNF, or IgSF receptor. In some more preferred embodiments, the peptide or mimetic mimics the second cysteine rich domain proximal to the transmembrane domain (S22 loop). In some preferred embodiments, the peptide mimetic mimics the S23 loop. According to some embodiments, the peptide mimetics of the present invention mimic cystine knots comprising regions.

In some preferred embodiments, the peptides and/or mimetics are exocyclic. In some preferred embodiments, the peptides and/or mimetics mimic full cystine knots. In some embodiments, the peptides and/or mimetics mimic a portion of a cystine knot.

In addition, peptides and/or mimetics may mimic assembly or functional epitopes of erbB2 and erbB1, erbB1 and erbB3, erbB1 and erbB4, erbB2 and erbB3, erbB2 and erbB4, erbB3 and erbB4, assembly or functional epitopes of TNF receptors, or assembly and functional epitopes of IgSF members.

In some embodiments, peptides and/or mimetics are provided which mimic dimerization sites of erbB, TNF, or IgSF receptors, and may induce antibodies. In a preferred embodiment, the peptides and/or mimetics mimic a dimerization site of erbB1 or erbB2. Binding of the peptides and/or mimetics or induced antibodies to the dimerization site prevents the dimerization of the receptor, and, preferably, reduces or eliminates receptor signaling.

In some embodiments, peptides and/or mimetics are provided which mimic conformation sites of erbB, TNF, or IgSF receptors, and may induce antibodies. In a preferred embodiment, the peptides and/or mimetics mimic a conformation site of erbB1 or erbB2. Binding of the peptides and/or mimetics or induced antibodies to the conformation site changes the conformation of the receptor and prevents the dimerization of the receptor, and, preferably, reduces or eliminates receptor signaling.

The peptides and/or mimetics of the invention are useful in the treatment of erbB tumors either as a component of a composition administered to a patient, as a component of a composition administered to a patient in combination with radiation therapy and/or chemotherapy, or as a component of a composition administered to a patient that comprises the peptides and/or mimetics conjugated to a radioactive or chemotherapeutic agent.

The peptides and/or mimetics of the invention are useful in the prevention of erbB tumors or TNF- or IgSF-mediated pathologies either as a component of a composition administered to a patient, as a component of a composition administered to a patient in combination with radiation therapy and/or chemotherapy, or as a component of a composition administered to a patient that comprises the peptides and/or mimetics conjugated to a radioactive or chemotherapeutic agent.

The peptides and/or mimetics of the invention are useful for raising antibodies. In some embodiments, an antibody is produced by immunizing a suitable host with a peptide selected from the group consisting of: Y-C-F-P-D-E-E-G-A-C-Y (SEQ ID NO:3); C-K-V-E-L-M-Y-P-P-P-Y-F-V-G-M-G-N-G-T-Q-I-Y-V-I-D-P-E-P-C (SEQ ID NO: 28); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); B2-S22-APE: Y-C-P-I-W-K-F-P-D-E-E-C-Y (SEQ ID NO: 31); B1-S22-ALG: Y-C-L-V-W-K-Y-A-D-A-G-C-Y (SEQ ID NO: 32); B3-S22-APQ: Y-C-P-1-Y-K-Y-P-D-V-Q-C-Y (SEQ ID NO: 33); B4-S22-AFD: Y-C-F-1-F-K-Y-A-D-P-D-C-Y (SEQ ID NO: 34); B2-S22-AFA: Y-C-F-P-D-E-E-G-A-C-Y (SEQ ID NO: 35). In some embodiments the antibody binds to a cysteine rich domain of an erbB receptor. In some embodiments, the peptides or mimetics induce antibodies that bind to functional sites of erbB, TNF, or IgSF family receptors.

The present invention also contemplates antibodies produced by immunizing a suitable host with a peptide selected from the group consisting of SEQ ID NOS:1-37 as well as antibodies produced by immunizing a suitable host with a peptide having the sequence in reverse order selected from the group consisting of SEQ ID NOS:1-37.

Antibodies

The present invention describes antibodies against receptor assembly domains.

According to certain embodiments, antibodies that bind to, for example, either erbB1, erbB2, erbB3 or erbB4 and are useful to prevent oligomerization-mediated signaling of receptors and thereby down modulate kinase activity of the receptors. When bound, the antibodies eliminate or reduce tyrosine kinase activity that results in an elimination or reduction in cell proliferation levels and a non-transformed, quiescent phenotype. The antibodies are therefore useful in the treatment of individuals suspected of having erbB tumors and in the prevention of such tumor formation. The cells in the individuals under treatment (that would otherwise turn into tumors in an untreated individual) do not become transformed and do not become tumors. When administered to individuals who have been identified as being susceptible to or otherwise at risk of developing tumors, the antibodies bind to, for example, erbB1, erbB2, erbB3 or erbB4, thereby preventing the elevation in tyrosine kinase activity associated with dimerization of the receptors. The tyrosine kinase activity in the cell never becomes sufficiently elevated and the cell remains non-transformed.

Antibodies useful in anti-tumor compositions can be produced by those skilled in the art using readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which provides detailed guidance for the production of hybridomas and monoclonal antibodies which specifically bind to target proteins. Briefly, the protein of interest, rodent or human erbB2, for example, or cells which express this protein, are injected into mice. The mouse is then boosted with the protein. The spleen of the mouse is removed and the spleen cells are isolated and fused with immortalized mouse cells. The hybrid cells, or hybridomas, are cultured and those cells which secrete antibodies are selected. The antibodies are analyzed and, if found to specifically bind to the protein of interest, the hybridoma which produces them is cultured to produce a continuous supply of antigen specific antibodies. Humainized or camelized antibodies may be generated using techniques well-known to those skilled in the art.

In some embodiments, antibodies are induced by immunizing an erbB or TNF receptor, or portion thereof. In more preferred embodiments, antibodies are induced by immunizing with a cystine knot peptide mimetic or peptide mimetic from cysteine rich domains with or without constraints.

In certain embodiments of the invention, the complementarity determining region of antibodies is formed from immunoglobulin heavy chains only, i.e., without immunoglobulin light chains. Such antibodies may be derived, for example, using antibody heavy chains from camelids, camels or llamas. (Davies et al., (1996) Protein Engineering, 9, 531-537; Reichmann, L., (1996) J. Mol. Biol., 259, 957-969; Davies et al., (1995) Biotechnology, 13, 475-479; Decanniere et al., (1999) Structure Fold Des., 7, 361-370). The structure of, e.g., the camelid single domain antibody is useful as a scaffold for anti-idiotypic vaccinations and expression of peptidomimetics (Muyldermans et al., (1999) J. Mol. Recognit., 12, 131-140; Dumoulin, et al., (2002), Prot. Sci., 11, 500-515; Tanha et al., (2001), J. Biol. Chem., 276, 24774-24780.)

In some embodiments, an antibody is produced by immunizing a suitable host with a peptide selected from the group consisting of: Y-C-F-P-D-E-E-G-A-C-Y (SEQ ID NO:3); C-K-V-E-L-M-Y-P-P-P-Y-F-V-G-M-G-N-G-T-Q-I-Y-V-I-D-P-E-P-C (SEQ ID NO: 28); C-K-I-E-F-M-Y-P-P-P-Y-L-D-N-E-R-S-N-G-T-I-I-H-I-K-E-K-H-L-C (SEQ ID NO:29); C-S-L-S-I-F-D-P-P-P-F-Q-E-R-N-L-S-G-G-Y-L-H-I-Y-E-S-Q-L-C (SEQ ID NO: 30); B2-S22-APE: Y-C-P-I-W-K-F-P-D-E-E-C-Y (SEQ ID NO: 31); B1-S22-ALG: Y-C-L-V-W-K-Y-A-D-A-G-C-Y (SEQ ID NO: 32); B3-S22-APQ: Y-C-P-1-Y-K-Y-P-D-V-Q-C-Y (SEQ ID NO: 33); B4-S22-AFD: Y-C-F-1-F-K-Y-A-D-P-D-C-Y (SEQ ID NO: 34); B2-S22-AFA: Y-C-F-P-D-E-E-G-A-C-Y (SEQ ID NO: 35). In some embodiments the antibody binds to a cystine knot of an erbB receptor.

According to some embodiments of the invention, a monoclonal antibody is provided that binds to human/rat erbB1, erbB2, erbB3, or erbB4-receptors.

Preferably, the binding affinity for antigens is at least $1 \times 10^6$ Ka, more preferably $1 \times 10^7$ Ka, more preferably $2 \times 10^7$ Ka, more preferably $1 \times 10^8$ Ka.

According to preferred embodiments of the invention, a monoclonal antibody is provided that binds to a human/rat TNF-receptor.

Preferably, the binding affinity for TNF antigens is at least $1 \times 10^6$ Ka. Preferably, the binding affinity for TNF receptors is at least $5 \times 10^6$ Ka, more preferably $1 \times 10^7$ Ka, more preferably $2 \times 10^7$ Ka, more preferably $1 \times 10^8$ Ka.

According to preferred embodiments of the invention, a monoclonal antibody is provided that binds to a human/rat IgSF family-receptor.

Preferably, the binding affinity for IgSF family-antigens is at least $1 \times 10^6$ Ka. Preferably, the binding affinity for IgSF family-receptors is at least $5 \times 10^6$ Ka, more preferably $1 \times 10^7$ Ka, more preferably $2 \times 10^7$ Ka, more preferably $1 \times 10^8$ Ka.

The present invention is useful to therapeutically treat an individual identified as suffering from erbB tumors and/or TNF of IgSF pathologies. The present invention is also useful to prophylactically treat an individual who is predisposed to develop erbB tumors or TNF/IgSF-related pathologies or who has had erbB tumors or TNF/IgSF-related pathologies and is therefore susceptible to a relapse or recurrence. The present invention is also useful, inter alia, to image erbB tumors or TNF/IgSF-related pathologies and otherwise detect them.

The antibodies of the invention are useful in the treatment of erbB tumors or TNF/IgSF-related pathologies either as a component of a composition administered to a patient, as a component of a composition administered to a patient in combination with radiation therapy and/or chemotherapy, or as a component of a composition administered to a patient that comprises the antibody conjugated to a radioactive or chemotherapeutic agent.

The antibodies of the invention are useful in the prevention of erbB tumors or TNF/IgSF-related pathologies either as a component of a composition administered to a patient, as a component of a composition administered to a patient in combination with radiation therapy and/or chemotherapy, or as a component of a composition administered to a patient that comprises the antibody conjugated to a radioactive or chemotherapeutic agent.

The antibodies of the invention are useful in the imaging of erbB tumors or TNF/IgSF-related pathologies as, for example, a detectable component of a composition administered to a patient.

General Features of Receptors with a Cysteine Rich Domain (CRD)

The crystal structure of the TNF receptor, both in complexed and uncomplexed forms, provides a general picture of how this receptor family binds to their ligands (Banner, et al. 1993; Eck and Sprang 1989; Eck, et al. 1992) and of associated ligand induced conformational changes. The receptors associate by structural elements known as cysteine-knots. The cystine knot in the TNF receptor family consists of 42 amino acid residues with 6 cysteine residues forming 3 interchain disulfide bonds to create the structural motif. The three-dimensional structure reveals the cysteine-knot repeats of about 30 Å in length are arranged in a head-to-tail fashion exposing the loops on one side of the receptor. These cysteine-knots are involved in both oligomerization and ligand binding (Eck and Sprang 1989; Eck, et al. 1992). Uncomplexed TNF receptors are observed as dimers. In the dimeric form, the first and last cysteine domains involve dimeric contacts (Naismith, et al. 1995). It has been argued that the TNF dimeric receptor forms regulate the function of the trimeric forms (Naismith, et al. 1995).

ErbB receptors share significant homology with TNF receptor (Ward, et al. 1995) in the cysteine rich domains. The recently determined crystal structure of insulin receptor (Garrett, et al. 1998b) confirmed that receptors with cysteine rich domains (CRD) adopt a similar conformation, namely the "cystine knot" observed in TNF receptors.

Anti-HER2/p185$^{c-neu}$ Antibody Binds to the Ectodomain and Leads to p185 Internalization Disabling a protein responsible for maintenance of the malignant phenotype reverses transformation. This body of work (Drebin, et al. 1986, Symp Fundam Cancer Res 38:277-289; Drebin, et al. 1986, Proc Natl Acad Sci USA 83:9129-9133) was subsequently substantiated (Carter, et al. 1992) and has now has been approved for clinical use as "HERCEPTIN" (Baselga, et al. 1998; Pegram, et al. 1998).

Antibodies to the ectodomain of p185 can reverse the phenotype of transformed cells by leading to the rapid downmodulation of the receptor from the cell surface (Drebin, et al. 1986, Proc Natl Acad Sci USA 83:9129-9133). The removal of the transforming receptor from the cell surface in vitro was associated with a reduction in the malignant phenotype and a conversion of the cell phenotype into a more normal one as judged by cell growth, phenotype, and growth in soft agar. The anti-receptor antibody p185 complex was visualized and shown to enter the cell and lead to p185 degradation (Brown, et al. 1994). Subsequent in vivo studies showed that the administration of anti-receptor antibodies alone could cause retardation of tumor growth.

Studies in small animals which had been treated to eliminate complement or macrophages clearly indicated that the effect of the antibodies was predominantly but not entirely direct and was related to receptor downmodulation (Drebin, et al. 1988).

Biochemical Aspects of Creating Mimetics that are Used In Vitro as Inhibitors

Reducing a macromolecule to a small molecule with similar function is a general chemical problem. There have been some attempts to design mini-proteins by transplanting functional units onto suitable scaffolds (Vita, et al. 1998) and minimizing antibodies to single chain antibodies (Magliani, et al. 1997).

It is now established that conformation constrained peptides are more bioactive than unconstrained ones. In recent years, the chemistry of peptide cyclization by solid phase synthesis and other methods has improved dramatically (Burgess, et al. 1996; Goodman and Shao 1996; Hanessian, et al. 1997; Koskinen and Hassila 1996; Kuhn, et al. 1997; Waid, et al. 1996; Zuckermann 1993) providing more opportunity to develop peptides into peptidomimetics.

General principles to create cyclic peptide mimetics that have been adopted and in some cases (such as eptifitimide (Integrilin) a glycoprotein llb llla inhibitor (COR Therapeutics)) have become clinically available. Aromatic residues placed at the termini of cyclically constrained small peptides increases the activity of mimetics (Takasaki, et al. 1997; Zhang, et al. 1996). Employing such modifications has allowed creation of high affinity mimetics of antibody mimics based on CDRs (Park, et al. 2000), CD4 (Zhang, et al. 1997), IL4 receptor loop mimetics, anti-CD3 antibody mimics, and TNF cystine knot mimetic that affect TNFα binding to its receptor (Takasaki, et al. 1997).

Cyclic Peptidomimetics are Superior Immunogens

Antigenic sites recognized by antibody consist of discrete three-dimensional surfaces (Van Regenmortel 1989; Van Regenmortel 1996). Spatial distribution of antigenic residues on the surface of proteins are often reproduced by constrained peptides (Kayak, et al. 1998; Posthumus, et al. 1991; Valero, et al. 1995; van der Werf, et al. 1994). An example involves the foot-mouth-and disease virus. A dominant antigenic site consists of flexible loop and immunization with a constrained peptide of this loop elicits higher affinity and neutralizing antibodies than the MAb elicited by linear peptides (Patel, et al. 1999; Valero, et al. 1995). These studies suggest that rigid, but spatial mimics of antigenic regions can be useful as immunogens and may be used to induce MAb to erb receptor interaction surfaces. These MAb are useful as in treatment of erbB pathologies.

Therapeutic Methods

The present invention is useful to therapeutically treat an individual identified as suffering from erbB tumors and/or TNF or IgSF-related pathologies in order to reverse the transformed phenotype of the tumor cells and/or induce tumor cell death. The present invention is useful to prophylactically treat an individual who is predisposed to develop erbB tumors and/or TNF or IgSF-related pathologies or who has had erbB tumors and/or TNF or IgSF-related pathologies and is therefore susceptible to a relapse or recurrence.

When a therapeutically effective amount of an antibody, peptide or mimetic of the present invention is administered to an individual who has erbB cancer, the proliferation rate of tumor cells is slowed down or eliminated.

Prophylactic methods are useful to treat an individual who is predisposed to develop erbB tumors and/or TNF or IgSF-related pathologies or who has had erbB tumors and/or TNF or IgSF-related pathologies and is therefore susceptible to a relapse or recurrence.

In some embodiments, the methods relate to treating patients suffering from human adenocarcinomas such as gastric, lung and pancreatic adenocarcinomas and human breast and ovarian carcinomas as well as human prostate cancer. In some embodiments, the methods relate to treating patients suffering from glial tumor progression, particularly in glioblastoma, the most malignant glial tumor. In some embodiments, the methods relate to treating patients suffering from human epithelial malignancies erythroid leukemia, fibrosarcoma, angiosarcoma and melanoma. In some embodiments the present invention provides methods of treating such diseases/disorders comprising the step of diagnosing a patient a suffering from a multimer-associated disease/disorder and then treating the disease/disorder in accordance with other methods of the invention.

Radiation therapy may commence anytime after a sufficient amount of time has elapsed for the antibodies or peptide mimetics to bind to the receptors. Generally, the individual is exposed to radiation in some cases 1-10 minutes after, in some cases 1-10 hours after, and in some cases up to 24-72 hours after administration of the antibodies, peptides or mimetics. In some cases, the radiation is provided in a single dose while in some embodiments, multiple doses are administered over several hours, days and/or weeks. The antibodies render the radiation resistant tumor cells radiation sensitive. Gamma radiation is delivered according to standard radiotherapeutic protocols using standard dosages and regimens. The administration of the antibodies, peptides or mimetics renders the radiation more effective in eradicating tumor cells.

The individual may be treated with antibodies, peptides or mimetics in combination with a cytotoxic chemotherapeutic agent in addition to or in lieu of exposure to a therapeutic amount of gamma radiation. Chemotherapy may commence anytime before or after the antibodies or peptide mimetics are administered, or with the antibodies, peptides or mimetics themselves. Generally, the individual is administered the chemotherapeutic in some cases 1-10 minutes after, in some cases 1-10 hours after, and in some cases up to 24-72 hours after administration of the antibodies, peptides or mimetics. In some cases, the chemotherapeutic is provided in a single dose while in some embodiments, multiple doses are administered over several hours, days and/or weeks. The antibodies render the tumor cells more sensitive to cytotoxic agents. Chemotherapeutics are delivered according to standard radiotherapeutic protocols using standard agents, dosages and regimens. In some embodiments, the chemotherapeutic is selected from the group consisting of: cisplatin, doxirubicin, danurubicin, tamoxiphen, taxol, and methotrexate. In some embodiments, the individual is treated with antibodies and/or peptides and/or mimetics of the present invention in combination with two or more chemotherapeutics, each administered prior to, simultaneous with, or after the other chemotherapeutics. In some embodiments, chemotherapy and radiation treatments are both employed following the administration of the active agent. In such embodiments, standard combinations of two or more therapeutic modalities are used in conjunction with administration of the antibodies and/or peptides and/or mimetics.

According to some embodiments of the invention, the patient is treated with radiation and/or other chemotherapy in conjunction with the administration of pharmaceutical compositions according to the invention. Chemotherapy approaches include administration of cytotoxic and or cytostatic agents. It has been observed that expression of nucleotide molecules according to the invention in erbB-associated tumors renders the tumors radiosensitized. That is, the tumors are more vulnerable to destruction by radiation during radiotherapy when the patient is treated with pharmaceutical compositions according to the invention. The use of multiple therapeutic approaches provides the patient with a broader based intervention. In some preferred embodiments, treatment with pharmaceutical compositions according to the present invention is preceded by surgical intervention. In preferred embodiments, radiotherapy follows administration of pharmaceutical compositions according to the invention. In preferred embodiments, the radiation therapy using gamma radiation is provided following administration of compositions which convert radiation resistant tumors into radiation sensitive tumors. Those skilled in the art can readily formulate an appropriate radiotherapeutic regimen. Carlos A Perez & Luther W Brady: Principles and Practice of Radiation Oncology, 2nd Ed. JB Lippincott Co, Phila., 1992, which is incorporated herein by reference describes radiation therapy protocols and parameters which can be used in the present invention. For GBMs (glioblastoma, the most malignant glial brain tumor), Simpson W. J. et al.: *Influence of location and extent of surgical resection on survival of patients with glioblastoma multiforms: Results of three consecutive Radiation Therapy Oncology Group (RTOG) clinical trials*. Int J Radiat Oncol Biol Phys 26:239-244, 1993, which is incorporated herein by reference, describes clinical protocols useful in the methods of the present invention. Similarly, for brain tumors, see Borgelt et al., *The palliation of brain metastases: Final results of the first two studies of the Radiation Therapy Oncology Group*. Int J Radiat Oncol Biol Phys 6:1-9, 1980, which is incorporated herein by reference and describes clinical protocols useful in the methods of the present invention.

The antibodies, peptides or mimetics of the present invention may be used to prevent tumors in individuals susceptible to such tumors. According to one aspect of the invention, antibodies are administered prophylactically to individuals susceptible to developing erbB tumors. According to another aspect of the invention, peptides are administered prophylactically to individuals susceptible to developing erbB tumors and/or TNF or IgSF-related pathologies. According to another aspect of the invention, mimetics are administered prophylactically to individuals susceptible to developing erbB tumors and/or TNF or IgSF-related pathologies. Those having ordinary skill in the art can readily determine whether an individual may be susceptible to such tumors. The methods are particularly useful in high-risk individuals who, for example, have a family history of erbB cancer, or show a genetic predisposition. Additionally, the methods are particularly useful to prevent patients from having recurrences of erbB tumors who have had erbB tumors removed by surgical resection or who have been diagnosed as having erbB-cancer in remission. In some preferred embodiments, the cancer is erbB2/erbB1 cancer.

Methods of treatment comprise administering single or multiple doses of the antibodies, peptides or mimetics of the present invention. Preferred for human pharmaceutical use are injectable pharmaceutical compositions that are sterile, pyrogen free and comprise the antibodies, peptides or mimetics in combination with a pharmaceutically acceptable carrier or diluent.

The antibodies, peptides or mimetics of the present invention may be used to treat individuals suffering from erbB tumors. According to one aspect of the invention, antibodies are administered to individuals suspected of having such tumors. According to another aspect of the invention, peptide mimetics are administered to individuals suspected of having such tumors. Those having ordinary skill in the art can readily determine whether an individual may have a tumor likely to be an erbB tumor. Biopsy protocols can be performed to identify tumor samples and determine whether or not they are erbB tumors. According to some aspects, the patient is treated with the antibodies, peptides or mimetics in conjunction with chemotherapy and/or radiation therapy. For example, following administration of the antibodies, peptides or mimetics, the patient may be treated with a therapeutically effective amount of anti-cancer radiation such as gamma radiation. Moreover, some embodiments provide chemotherapeutic treatment in combination with the antibodies, peptides or mimetics. Other aspects of the invention involve the administration of antibodies, peptides or mimetics in conjunction with chemotherapy and/or radiation therapy. In some preferred embodiments, the cancer is erbB2/erbB1 cancer.

The present invention is also useful for preventing erbB tumors or formation of a vaccine for prevention or treatement of erbB tumors. The term "vaccine", as used herein, broadly refers to any compositions that may be administered to an organism to protect the organism against an infectious disease. The term "protect", as used herein to describe vaccines, means prevention or treatment of the infectious disease. Vaccines protect against diseases, e.g., erbB tumors, by inducing or increasing an immune response in an organism against infectious agents or against cells that have undergone transition to an abnormal or diseased state. An erbB vaccine, e.g., illicits an immune response against cells that express abnormal amounts or forms of an erbB receptor such as that found on abnormal or transformed cells.

A vaccine generally comprises a therapeutically effective dose of an immunogen (e.g., an antigen) and, preferably, an adjuvant and/or a pharmaceutically acceptable carrier.

A vaccine may be administered to an organism, e.g., by inhalation or insufflation (either through the mouth or the nose), or by oral, buccal, rectal or parenteral administration (e.g., by subcutaneous, intramuscular, intraorbital, intracapsular, intraspinal, intrasternal or intravenous injection and the like). A vaccine may also be administered by particle-mediated transfer (e.g., using a "particle gun"). See for example, Gainer et al., *J. Neurooncol* 2000, 47:23-30; Koide et al., *Jpn J. Pharmacol* 2000, 83:167-174; Kuriyama et al., *Gene Ther.* 2000, 7:1132-1136; and Yamauchi et al., *J. Exp. Zool.* 2000, 287:285-293. Such particle transfer methods are particularly preferred for DNA or vector vaccines (discussed below), e.g., using a "gene gun".

A vaccine of the invention may comprise, for example, a polypeptide vaccine or a DNA vaccine. The term "polypeptide vaccine" refers to a vaccine comprising an immunogenic polypeptide, which may be an antigen, and therefore activates an immune response in an organism. The term "DNA vaccine" is an informal term of art, and is used herein to refer to vaccines delivered by means of a recombinant vector. An alternative term used herein is "vector vaccine" (since some potential vectors, for example retroviruses and lentiviruses, are RNA viruses and since in some instances non-viral RNA instead of DNA may be delivered to cells).

The peptides and mimetics disclosed herein may be used in a vaccine. In certain embodiments, the vaccine comprises a subdomain IV sequence of an erbB receptor. In a preferred embodiment, the erbB receptor subdomain IV sequence is from human erbB. Most preferably the subdomain IV sequence has a sequence selected from the group consisting of SEQ ID: 39, SEQ ID: 40, SEQ ID: 41 and SEQ ID: 42. In other embodiments, the vaccine comprises a peptide of between 10-25 contiguous amino of an erbB receptor subdomain IV. In another embodiment, the vaccine comprises an erbB subdomain IV wherein between 1-10 amino amino acids of the subdomain have been substituted with a conservative amino acid. Such conservative amino acid changes are well known to those in the art.

It is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981).

Methods of Imaging and Diagnosing Mammalian Tumors

The present invention is also useful, inter alia, to image erbB tumors and TNF or IgSF-related pathologies and otherwise detect or diagnose them.

The antibodies, peptides or mimetics of the present invention can be labeled or otherwise made detectable. For example, a detectable antibody is useful as an imaging agent and reagent in diagnostic procedures that are used to identify tumors. Labeled antibodies can be administered to individuals suspected of suffering from erbB tumor and/or TNF or IgSF-related pathologies. The labeled antibodies will bind to the high density of receptors on cells and thereby accumulate on the tumor cells. Using standard imaging techniques, the site of the tumors can be detected.

One aspect of the invention therefore relates to methods of imaging tumors. Such methods comprise the steps of administering a detectable antibody, peptide or mimetic to an individual who is suffering from or is susceptible to erbB cancer and detecting the location of the detectable antibody, peptide or mimetic within the body of the individual or within a sample obtained from said individual.

The antibodies, peptides or mimetics bind to receptors present on cell surfaces and are therefore useful as diagnostic/characterizing reagents in diagnostic kits. When a tissue sample from an individual is contacted with an antibody, peptide or mimetic, the antibody, peptide or mimetic will bind to the receptors present on cells. Labeled antibodies, peptides or mimetics are also useful as in vitro reagents to quantify the amount of receptors present in the cell. Such information indicates whether or not a tumor is erbB-related and, therefore, whether specific treatments should be used or avoided. Using standard techniques, samples believed to include tumor cells are obtained and contacted with labeled antibodies, peptides or mimetics. After removing any unbound, labeled antibodies, peptides or mimetics, the quantity of labeled antibodies, peptides or mimetics bound to the cell, or the quantity of antibodies, peptides or mimetics removed as unbound, labeled antibodies is determined. The information directly relates to the amount of receptors. This information is useful in formulating the prognosis and course of treatment to be imposed on the individual.

Imaging agents are useful in diagnostic procedures as well as in procedures used to identify the location of tumors. Imaging can be performed by many procedures well-known to those having ordinary skill in the art and the appropriate imaging agent useful in such procedures may be conjugated to antibodies by well-known means. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as an iron chelate. MRI scanning may employ chelates of gadolinium or manganese. Additionally, positron emission tomography (PET) may be possible using positron emitters of oxygen, nitrogen, iron, carbon, or gallium.

In another embodiment, a diagnostic method is provide in which radiolabeled F(ab)' fragments prepared from the monoclonal antibodies of the present invention are administered to patients. The location and size of the tumor are determined by gamma-scintigraphy to detect the radiolabeled F(ab•) fragments.

In some embodiments, tumors can be diagnosed by contacting tissue portions of the tumor with a antibody being labeled with an indicator. The antibody binds to the erbB oligomer present in the cells of the tissue portion. The indicator is then detected. In preferred embodiments of the invention, the indicator comprises biotinylated horse anti-mouse immunoglobulin and streptavidin-biotinylated-peroxidase. The indicator in detected by contacting the indicator with a chromogenic substrate which preferably comprises 3,3'-diaminobenzidine, hydrogen peroxide and imidazole. The chromogenic substrate is then detected by microscopy.

In some embodiments, tumors can be diagnosed by contacting tissue portions of the tumor with a labeled peptide or mimetic. The labeled peptide or mimetic binds to the erbB receptor present in the cells of the tissue portion. The indicator is then detected. In preferred embodiments of the invention, the indicator comprises biotinylated horse anti-mouse immunoglobulin and streptavidin-biotinylated-peroxidase. The indicator in detected by contacting the indicator with a chromogenic substrate which preferably comprises 3,3'-diaminobenzidine, hydrogen peroxide and imidazole. The chromogenic substrate is then detected by microscopy.

Pharmaceutical Compositions

The invention further provides an injectable composition for treatment of a mammalian cancer tumor having cells that express erbB receptors or TNF receptors on the surfaces of the cells. In accordance with the invention, the composition comprises an antibody, peptide or mimetic specific to the shared epitope and a pharmaceutically acceptable injection vehicle.

When a therapeutically effective amount of an antibody, peptide or mimetic of the present invention is administered to an individual who has erbB cancer or TNF or IgSF-related pathology, the proliferation rate of cells is slowed down or eliminated.

The pharmaceutical compositions of the present invention may be administered by any means that enables the antibodies, peptides or mimetics to reach the agent's site of action in the body of a mammal. Because proteins are subject to being digested when administered orally, parenteral administration, i.e., intravenous, subcutaneous, intramuscular, would ordinarily be used to optimize absorption. Formulations may be devised which protect the antibodies, peptides or mimetics and render them resistant to many proteases, thus making them orally available.

In addition to pharmaceutical compositions which comprise antibodies, peptides or mimetics alone or in combination with other cancer therapeutics, therapeutic and diagnostic pharmaceutical compositions. The pharmaceutical compositions which comprise conjugated compositions may be used to diagnose or treat individuals suffering from erbB and/or TNF cancer.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The compositions may include additional components to render them more effective. For example, a composition of the invention may comprise multiple anti-p185 antibodies. The compositions may include other anti-cancer agents such as, for example, cis-platin, methotrexate, and/or GM-CSF. Such compositions would be particularly useful for administration to patients diagnosed and treated for erbB-associated cancer.

Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, e.g., *Remington's Pharmaceutical Sciences* and *The U.S. Pharmacopoeia/National Formulary*, latest editions, provide considerable guidance in this respect, each of which is incorporated by reference in its entirety A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

Kits

Kits of the invention comprise detectable antibodies and/or peptides and/or mimetics and instructions for performing assays of the invention. Optionally, kits may also contain one or more of the following: containers which comprise positive controls, containers which comprise negative controls, photographs of representative examples of positive results and photographs of representative examples of negative results.

Conjugates

Antibodies, peptides or mimetics may be conjugated to a detectable and/or cytotoxic agent. In conjugated compositions, the antibodies, peptides or mimetics of the invention deliver the active agent to cells. Thus, cells with the receptors will be contacted with more active agents than other cells. The active agent is useful to image, inhibit proliferation of and/or kill the cell. The active agent may be a therapeutic agent or an imaging agent.

Some chemotherapeutic agents may be used as active agents and conjugated with antibodies, peptides or mimetics. Chemotherapeutics are typically small chemical entities produced by chemical synthesis and include cytotoxic drugs, cytostatic drugs as well as antibodies which affect cells in other ways such as reversal of the transformed state to a differentiated state or those which inhibit cell replication. Examples of chemotherapeutics include, but are not limited to: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin.

Active agents may be toxins: complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. Protein toxins may be produced using recombinant DNA techniques as fusion proteins that include peptides of the invention. Protein toxins may also be conjugated to antibodies by non-peptidyl bonds.

Radioisotopes may be conjugated to antibodies, peptides or mimetics to provide compositions that are useful as therapeutic agents or for imaging procedures. Examples of radioisotopes which useful in radiation therapy include: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi. Example of radioisotopes useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{90}$Y, $^{99M}$Tc, $^{111}$In, $^{113M}$In, $^{123}$I, $^{125}$I, $^{18}$F, $^{86}$Y, $^{127}$Cs, $^{129}$Cs, $^{131}$I, $^{132}$I, $^{197}$Hg, $^{203}$Pb and $^{206}$Bi.

Radiolabels are conjugated to antibodies, peptides or mimetics by a variety of well-known techniques readily performed without undue experimentation by those having ordinary skill in the art. Radiolabels retain their radioactivity irrespective of conjugation. Conjugation may be accomplished directly between the antibody, peptide or mimetic and the radioisotope or linking, intermediate molecular groups may be provided between the antibody, peptide or mimetic and the radioisotope. Crosslinkers are particularly useful to facilitate conjugation by providing attachment sites for each moiety. Crosslinkers may include additional molecular groups which serve as spacers to separate the moieties from each other to prevent either from interfering with the activity of the other. Often imaging can be imaged using fluorescein, which are activated by light. (e.g. fluorescein (green), phycoerythrin (orange), P-E-cyanine-5 (red), P-E-texas red (red), cyanine-3 (orange), cyananine-5 (red), AMCA (ultraviolet detection)

One having ordinary skill in the art may conjugate an antibody, peptide or mimetic to a chemotherapeutic drug using well-known techniques. For example, Magerstadt, M. *Antibody Conjugates and Malignant Disease.* (1991) CRC Press, Boca Raton, USA, pp. 110-152) which is incorporated herein by reference, teaches the conjugation of various cytostatic drugs to amino acids of an antibody, peptide or to a mimetic. Such reactions may be applied to conjugate chemotherapeutic drugs to the antibody, peptide or mimetic. Antibodies such as peptides which have a free amino group may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of a antibody of the invention.

Administration of Pharmaceutical Compositions

The dosage of the compositions of the present invention administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. In some preferred embodiments, about 5 μg to 5000 mg of antibody, peptide or mimetic may be administered. In some preferred embodiments, 50 μg to 500 mg of antibody, peptide or mimetic may be administered. In other preferred embodiments, 500 μg to 50 mg of antibody, peptide or mimetic may be administered. In a preferred embodiment, 5 mg of antibody, peptide or mimetic is administered.

Compositions may be administered by an appropriate route such as, for example, by oral, intranasal, intramuscular, intraperitoneal or subcutaneous administration. In some embodiments, intravenous administration is preferred. In some embodiments, the composition is administered by intraarterial, intradermal, parenteral, or intratumoral administration. According to some preferred embodiments, the individual has had surgery to remove bulk tumor mass prior to administration of the composition.

According to some embodiments of the invention, the pharmaceutical compositions are administered locally at the site of the tumor. In some embodiments, the pharmaceutical compositions are administered directly into the tumor cells and the tissue immediately surrounding the tumor. In some embodiment, the pharmaceutical compositions are delivered into brain tumors such as, for example, glioblastomas. In some embodiments, the pharmaceutical compositions are delivered into brain tumors as part of the surgical resection of the tumor. In some embodiment, the pharmaceutical compositions are delivered into brain tumors using stereotaxic surgical techniques.

Subsequent to initial administration, individuals may be boosted by readministration. In some preferred embodiments, multiple administrations are performed.

Dosage forms (composition) suitable for internal administration generally contain from about 1 milligram to about 500 milligrams of active ingredient per unit. In these pharmaceutical compositions the active ingredient will ordinarily be present in an amount of about 0.5-95% by weight based on the total weight of the composition.

Because conjugated antibody, peptide or mimetic are specifically targeted to cells with erbB, TNF, or IgSF receptors, conjugated antibody, peptide or mimetic which comprise chemotherapeutics or toxins are administered in doses less than those which are used when the chemotherapeutics or toxins are administered as unconjugated active agents, preferably in doses that contain up to 100 times less active agent. In some embodiments, conjugated antibody, peptide or mimetic which comprise chemotherapeutics or toxins are administered in doses that contain 10-100 times less active agent as an active agent than the dosage of chemotherapeutics or toxins administered as unconjugated active agents. To determine the appropriate dose, the amount of antibody, peptide or mimetic is preferably measured in moles instead of by weight. In that way, the variable weight of different antibodies, peptides or mimetics does not affect the calculation. For example, presuming a one to one ratio of antibody to active agent in conjugated compositions of the invention, fewer moles of conjugated antibodies may be administered as compared to the moles of unconjugated antibodies administered, preferably up to 100 times less moles.

For parenteral administration, the antibody, peptide or mimetic can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field which is incorporated by reference in its entirety.

For example, a parenteral composition suitable for administration by injection is prepared by dissolving 1.5% by weight of active ingredient in 0.9% sodium chloride solution.

The antibody, peptide or mimetic may be administered to a tissue of an individual topically or by lavage. The antibodies, peptides or mimetics may be formulated as a cream, ointment, salve, douche, suppository or solution for topical administration or irrigation. Formulations for such routes administration of pharmaceutical compositions are well known.

The present invention is not intended to be limited by any theory. The present invention is further illustrated by the following examples, which are not intended to be limiting in any way.

EXAMPLES

Example 1

The Cysteine Rich Subdomain is Responsible for Dimerization of Either Homomeric or Heteromeric ErbB Species The process of homodimerization and heterodimerization in the erbB system has been described (Wada, et al. 1990, Cell, 61:1339-1347). Intermolecular association and transphosphorylation of receptor molecules result in activated heterodimeric kinase complexes which may provide qualitative or quantitative differences in phosphotyrosine sites necessary for cellular substrate binding. The basic features of heterodimerization of p185 with the EGFr have now been found for other members of this family. Both erbB3 and erbB4 heterodimerize with HER2/neu indicating that this feature represents a general mechanism of increasing complexity and diversification of receptor function. Dimers may nucleate the formation of tetramers or even more complex assemblies.

Figure 1B:
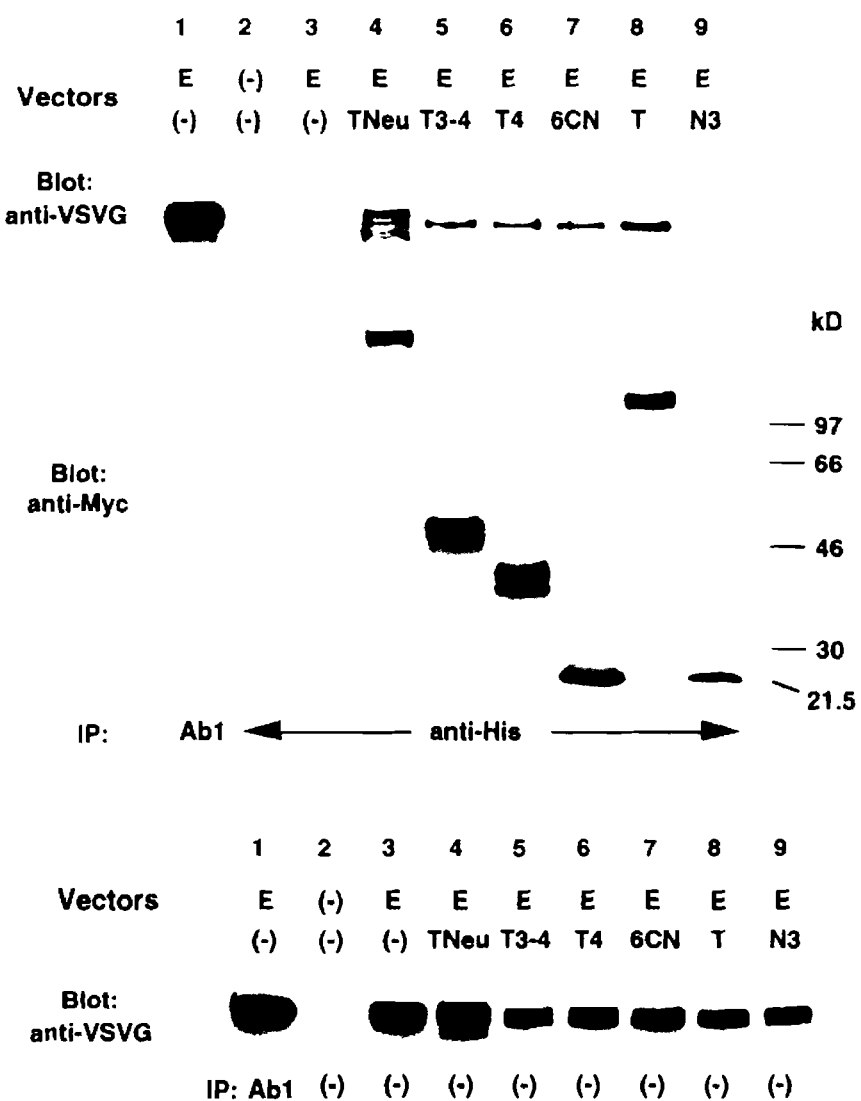

Dimerization studies were conducted as described in (Kumagai et al., 2001). Derivatives of p185neu were constructed, to determine which subdomains were required for homo- and heterodimerization. A series of deletion mutants of ectodomain forms of p185neu were created that included a portion of the ectodomain, the transmembrane region, and a few residues of the endodomain linked to a tag (FIG. 1A). Transfection into Cos 7 cells of all the mutant species led to comparable expression. The lysates of cells transfected with the neu species and EGFr were lysed and immunoprecipitated with antibodies specific for the His tag found on the neu species (or, for lane 1, anti EGFr) and then blotted with antibodies specific for the VSVG (vesicular stomatitis virus glycoprotein) tag placed on the EGF receptor (top panel) and the Myc tag on the neu receptor (middle panel). Constructs composed only of subdomain IV associated with the EGFr holoreceptor (FIG. 1B, lane 4). A fragment of 46 amino acids of subdomain IV, (6CN lane 7) that includes the distal 6 cysteines as its ectodomain, also associates with the EGFr.

In the schematic diagram given in FIG. 1A, numbers refer to amino acid positions from the first Met at N-terminal of Neu or EGFr. Other references are as follows: SP, signal peptide; I, subdomain I; II, subdomain II; III, subdomain III; IV, subdomain IV; TM, transmembrane domain; hatched squares, TM with single-point mutation (V664G) in transmembrane domain; TK, tyrosine kinase domain; Myc, Myc epitope; His, polyhistidine tag; VSVG, VSVG tag; broken line, deleted region. In FIG. 1B immunoblots (IB) were performed with the antibodies as described infra. The membrane in the upper panel was blotted with anti-VSVG and then reblotted with anti-Myc as indicated in the middle panel. The same total cell lysates were subjected to a nitrocellulose membrane (bottom panel) in order to determine the exogenous expression of EGFr (supra and infra).

Other studies compared the ability of EGF to stimulate MAP kinase activation by the EGFr when these variant p185neu species were also expressed. It was found that the pTex6CN form was able to associate with the EGFr and inhibit the kinase activation of the EGFr. (Kumagai et al., 2001). The terminal 46 amino acids region is composed of cystine knots. These studies emphasize the critical nature of the cystine knot containing regions of erbB as essential for the assembly of erbB receptor complexes.

These results suggested that small forms of cystine knot mimetics might be used as antagonists of receptor oligomerization. These results also provide the framework for developing the new class of MAb reactive with this region of p185 as a means to disable receptor associations as a new approach to preempt or disrupt transforming complexes.

Example 2 erbB Subdomain IV Cystine Knot Mimetics

A series of peptides was designed to mimic potential dimerization sites in the C-terminal part of the S2 domain of different erbB receptors using molecular models of the dimeric complexes. The peptides were designed based on the molecular model of the subdomain IV of erbB receptors constructed by comparative modeling with the second subdomain of the type-1 insulin-like growth factor receptor (IGF-1R), as well as structures of the TNF receptor and laminin that have similar disulfide bond connectivities (Garrett, et al. 1998, Nature, 394:395-9; Naismith, et al. 1995, J Biol. Chem, 270:13303-13307; Naismith and Sprang 1998, Trends Biochem Sci, 23:74-9).

The following peptides were constructed:

```
B1-S22-ALG (derived from erbB1)
                                        (SEQ ID NO: 32)
YCLVWKYADAGCY;

B2-S22-APE (derived from erbB2)
                                        (SEQ ID NO: 31)
YCPIWKFPDEECY;

B2-S22-AFA (derived from erbB2)
                                        (SEQ ID NO: 35)
YCFPDEEGACY;

B2-S23-BPT (derived from erbB2):
                                        (SEQ ID NO: 38)
PCPINCTHSCVDLDDKGCPAEQRASPLTSI;

B3-S22-APQ (derived from erbB3)
                                        (SEQ ID NO: 33)
YCPIYKYPDVQCY;
and B4-S22-AFD (derived from erbB4)
                                        (SEQ ID NO: 34)
YCFIFKYADPDCY.
```

Peptides B1-S22-ALG, B2-S22-APE, B2-S22-AFA, B3-S22-APQ and B4-S22-AFD mimic the S22 repeat. B2-S23-BPT was derived from the membrane-proximal S23 repeat. A CD4 receptor-derived cyclic peptide, CD4-G (FCYIGEVEDQCY; SEQ ID NO: 43), was designed as a negative control.

Figure 2:
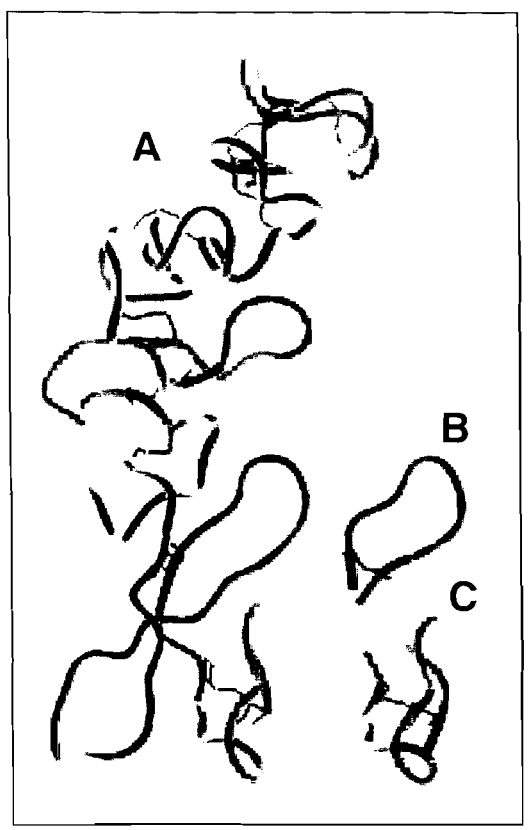
FIG. 2A-C. Molecular model of ErbB-2: Second cysteine rich domain proximal to transmembrane (S22) is shown (A). This module adopts a similar topology as that of the TNF receptor. Peptides designed from A2-like domains are exocyclic (S22-AFA; B) while peptides from B2-like domains (S23-BPT; C) are fashioned as full cystine knots.

FIG. 2 shows the molecular models of the fourth subdomain of HER2 and mimetic peptides derived from the C-terminal part of this subdomain. B2-S22-AFA is a cyclic peptide that mimics part of the S22 loop. B2-S23-BPT is a bicyclic peptide constrained by two disulfide bonds and represents a whole S23 repeat followed by the juxtamembrane amino acid residues. Molecular modeling indicates close conformational similarity between the constrained mimetic peptides and corresponding loops of the receptor. Based on the existing structural and experimental data, a possible arrangement of the receptor has been proposed, and the S22 domain is suggested as a major inter-receptor interaction site within the complex.

Example 3

Kinetic Binding Analysis of the S22 Peptide

The designed erbB peptides were tested for binding to erbB receptors using surface plasmon resonance (Biacore) technology (described supra) using soluble erbB-1 and erbB-3. The response was plotted in real time in the form of sensorgram curves. Dissociation constants ($K_d$) were determined as described (Park, et al. 2000, Nat. Biotechnol. 18:194-198).

Figure 3A:
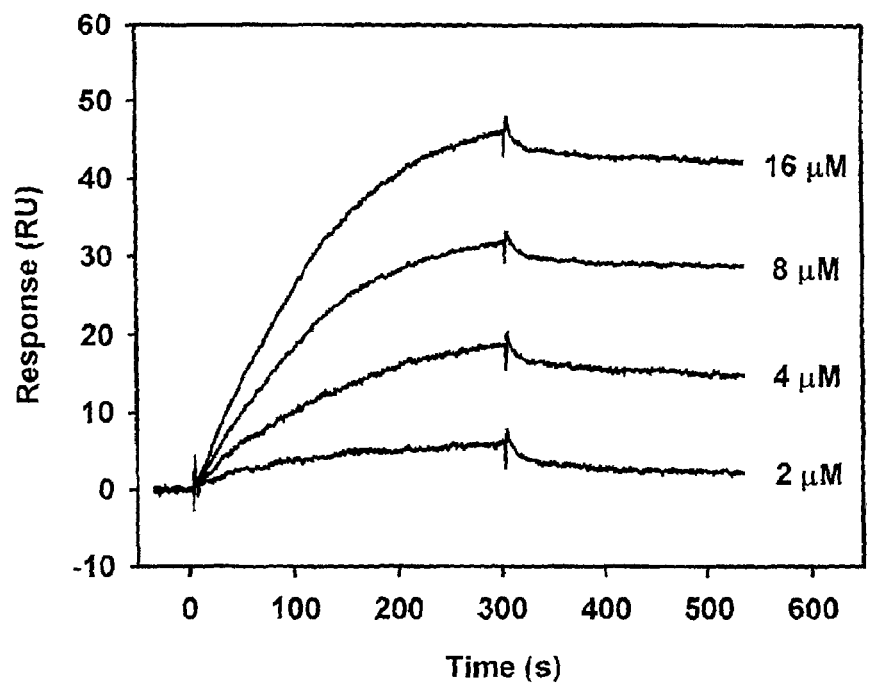
FIG. 3A-B. Surface plasmon resonance analysis of the interaction between the B2-S22-APE peptide and the ectodomain of erbB2 (A) or erbB2-SbdIV (B). Dose response.

A sensorgram for binding of B2-S22-APE peptide to erbB receptors immobilized on the sensor chip was performed. (FIG. 3A.) Kinetic constants were estimated by global fitting analysis of the titration curves to the 1:1 Langmurian interaction model, which gave a $k_{on}$ of $3.24 \times 10^3$ $M^{-1}$ $s^{-1}$, and a $k_{off}$ of $6.85 \times 10^{-4}$ $s^{-1}$. The $k_{off}/k_{on}$ ratio gave a value of 0.21 µM for the dissociation constant ($K_d$). Good fitting of experimental data to the calculated curves has been observed, suggesting a simple pseudo-first order interaction between the peptide and the receptor.

$K_d$ values for other erbB peptides, analyzed in a similar fashion as B2-S22-APE, are presented in Table 1. All erbB peptides showed binding to different erbB receptors. However, no binding could be detected to the immobilized TNF receptor used as a control, indicating selectivity of erbB peptides to the erbB receptor family. A control CD4-G peptide did not bind to any of the studied receptors. Some binding specificity could also be observed for different peptides within the erbB family. Thus, erbB2-derived peptide, B2-S22-APE could bind to the erbB1 receptor better than to erbB2 and erbB3. ErbB1-derived B1-S22-ALG showed preferential binding to erbB3. ErbB2-derived B2-S22-AFA peptide did not have a high specificity within erbB receptors, but showed the best overall binding affinity to all three receptors.

TABLE 1

ErbB receptor-derived peptides. Binding to the immobilized extracellular domains of the ErbB receptors studied by surface plasmon resonance.

| | $K_D$ (µM) | | | |
|---|---|---|---|---|
| | ErbB1 | ErbB2 | ErbB3 | TNFR |
| B2-S23-BPT | 2.06 | 4.23 | 0.832 | >$10^3$ |
| B2-S22-APE | 0.210 | 1.53 | 1.40 | >$10^3$ |
| B1-S22-ALG | 0.449 | 0.371 | 0.288 | >$10^3$ |
| B3-S22-APQ | 0.472 | 0.549 | 1.07 | >$10^3$ |
| B4-S22-AFD | 0.583 | 0.639 | 0.394 | >$10^3$ |
| B2-S22-AFA | 0.407 | 0.302 | 0.429 | >$10^3$ |
| CD4-G | >$10^3$ | >$10^3$ | >$10^3$ | >$10^3$ |

* C-terminus is blocked with $NH_2$

Figure 3B:
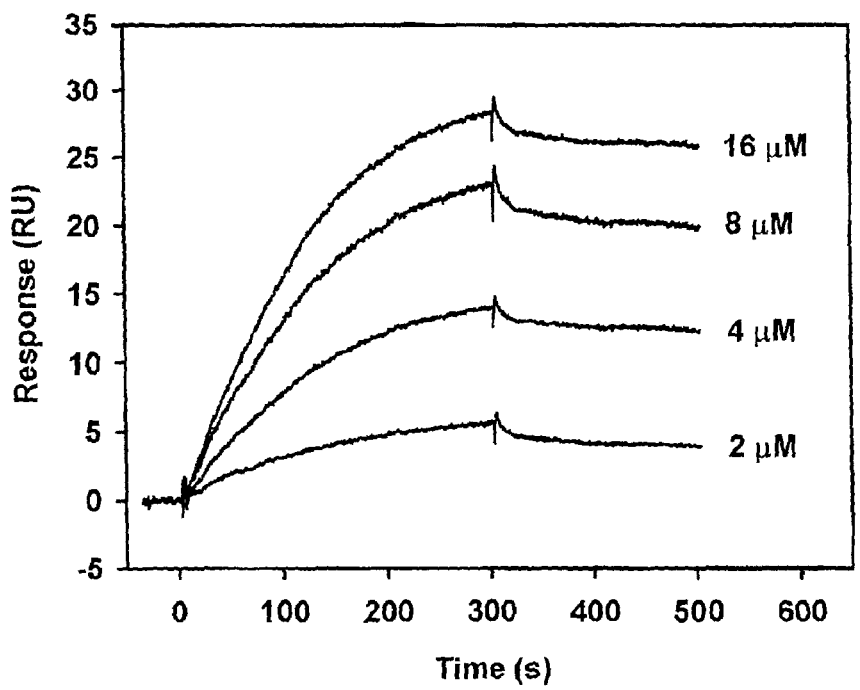

To demonstrate that erbB peptides bind to Sbd IV of erbB receptors, the interaction of the B2-S22-APE peptide with recombinantly expressed erbB2-SbdIV immobilized on the surface chip was determined (FIG. 3B). The observed binding to erbB2-SbdIV had very similar kinetic constants ($k_{on}$, $1.62 \times 10^3$ $M^{-1}$ $s^{-1}$; $k_{off}$, $3.07 \times 10^{-3}$ $s^{-1}$) and affinity ($K_D$, 1.89 µM) as binding to the whole ectodomain of erbB2 (FIG. 3A; Table 1). Binding of other erbB peptides to erbB2-Sbd IV was undistinguishable from their binding to the full-size erbB2 ectodomain (data not shown), demonstrating that subdomain IV is the binding site for all erbB peptides. Since erbB peptides are derived from subdomain IV of different erbB receptors, this fact indicates direct involvement of subdomain IV in receptor-receptor interactions between the members of erbB receptor family.

Example 4

Inhibition of Receptor Self-Associations

Surface Plasmon Resonance Studies.

Figure 4:
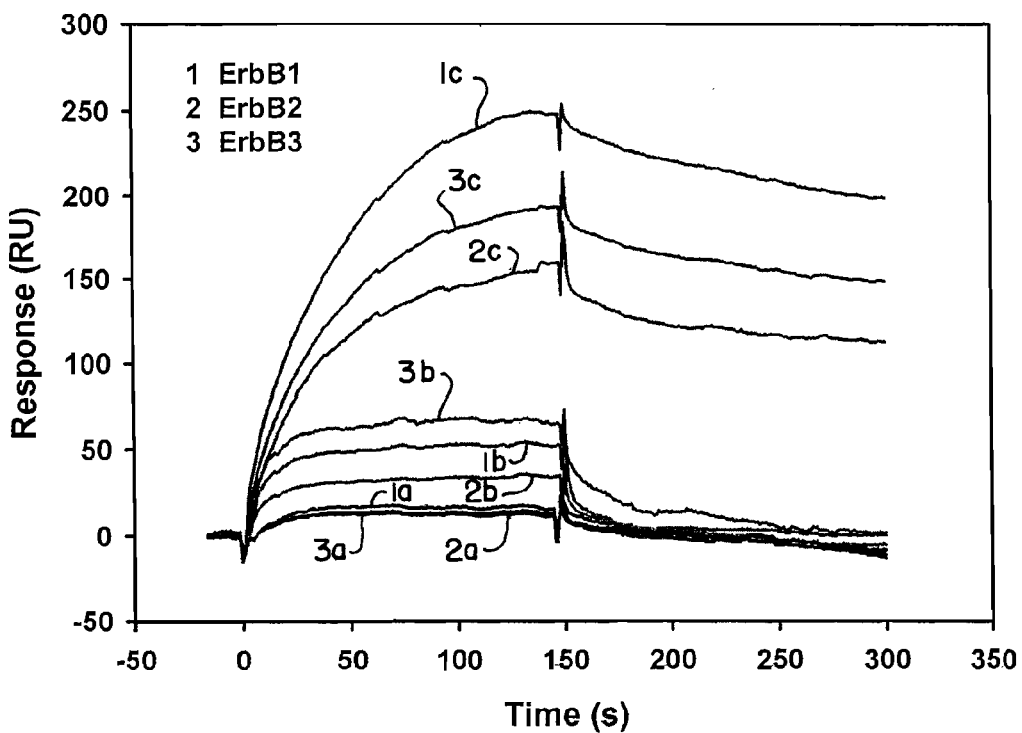
FIG. 4. Surface plasmon resonance analysis of the inhibitory effect of the B2-S22-AFA peptide on the heregulin-induced oligomerization of erbB receptors. ErbB1, erbB2, and erbB3 were immobilized on the surface chip and 300 nM erbB3 was injected either alone (1A, 2A, 3A) or in the presence of 5 µM HRGβ1 (1C, 2B, 3C). Traces 1B, 2B and 3B show binding of erbB3 to the immobilized receptors in the presence of HRGβ1 after pre-injection of B2-S22-AFA at 10 µM.

The effect of cysteine-knot mimetics on receptor self-associations, was examinded using a Biacore assay in which the ectodomains of erbB receptors were immobilized on the surface chip and the ectodomain of erbB3 was injected at 300 nM concentrations either alone or in the presence of 5 µM hereglunin HRGβ1. A very limited degree of receptor-receptor interactions in the absence of heregulin was observed. (FIG. 4; 1A, 2A, 3A.) However, when erbB3 was preincubated with about 17-fold molar excess of HRGβ1, a strong binding to all three erbB receptors was observed (FIG. 4; 1C, 2C, 3C), indicating ligand-induced homo- and heteromerization of the erbB receptor ectodomains. No increase in binding upon preincubation with heregulin was observed for the TNF receptor used as a control (data not shown). Kinetic analysis of the dose response curves (data not shown) revealed that the strongest binding was observed for erbB3-erbB1 heteromerization ($K_D$, 2.3 nM), followed by erbB3-erbB3 homomerization ($K_D$, 7.2 nM) and erbB3-erbB2 heteromerization ($K_D$, 17.9 nM).

In a parallel experiment, it was determined whether similar ligand-induced receptor self-associations could be observed for the erbB1 receptor injected in the presence of EGF or TGFα. However, no interaction of the injected erbB1 ectodomain (150 nM) with the immobilized receptors could be detected either in the absence or in the presence of the erbB1 ligands (5 µM), suggesting that at this erbB1 receptor concentration no significant dimerization is taking place.

The effect of the erbB peptides on heregulin-induced receptor self-associations was studied by preinjecting them at 10 µM followed by injection of erbB3-HRGβ1 (FIG. 4; 1B, 2B, 3B). The B2-S22-AFA peptide effectively inhibited binding of erbB3 to all three immobilized receptors. The highest degree of inhibition was observed for the erbB3-erbB2 heteromerization (82.5%) followed by erbB3-erbB1 heteromerization (78.4%) and erbB3-erbB3 homomerization (61.7%). As a control, either the running buffer or a control peptide (CD4-G) were preinjected instead of the ErbB peptides and showed no effect on receptor self-associations (data not shown).

Values for inhibition of dimerization of different erbB peptides are given in Table 2. As expected from the data for the receptor-binding affinities, B2-S22-APE, which showed the best binding to erbB1 (Table 1), was more effective in disabling interaction of erbB3 with erbB1 than with other receptors (Table 2). Similarly, B1-S22-ALG with the highest erbB3-binding affinity (Table 1) was the strongest inhibitor of erbB3 homodimerization (Table 2). B2-S22-AFA with the strongest overall affinity to the three studied erbB receptors (Table 1), is an effective inhibitor of erbB3-erbB2 and erbB3- erbB1 interactions (Table 2). B2-S23-BPT, derived from the S23 repeat of erbB2, had the lowest but still significant inhibitory effect, especially on the homomerization of erbB3 (Table 2) to which it binds with the highest affinity compared to other receptors (Table 1).

TABLE 2

Inhibition of ligand-induced ErbB receptor dimerization by ErbB receptor-derived peptides.

| | Percent Inhibition[a] | | |
|---|---|---|---|
| | ErbB1 | ErbB2 | ErbB3 |
| B2-S23-BPT | 41.5 | 32.3 | 55.4 |
| B2-S22-APE | 80.3 | 51.1 | 42.7 |
| B1-S22-ALG | 65.2 | 71.4 | 75.1 |
| B3-S22-APQ | 69.0 | 58.1 | 32.4 |
| B4-S22-AFD | 60.3 | 54.2 | 72.8 |
| B2-S22-AFA | 78.4 | 82.5 | 61.7 |
| CD4-G | 2.4 | −1.2 | 3.1 |

[a]Inhibitory effect of ErbB peptides (10 μm) on the binding of ErbB3 (300 nm) to the immobilized ErbB receptors in the presence of HRGβ1 (5 μM).

Inhibition of Ligand-Induced Dimerization of Native erbB Receptors in 32D Cell Lines.

Figure 5:
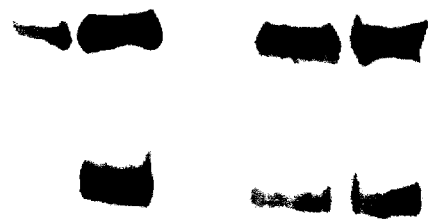
FIG. 5. Inhibitory effect of the B2-S22-AFA and B3-S22-APQ peptides on the heregulin activation and dimerization of ErbB receptor. (A) 32D-E2/E4 cells were incubated in the absence (−) or presence (+) of 10 µg/ml HRGβ and 10 µg/ml erbB peptides and analyzed by chemical cross-linking and immunoblotting experiments as described in the Experimental Procedures. (B) Dose dependence of the inhibitory effect by the B2-S22-AFA peptide.
Figure 5:
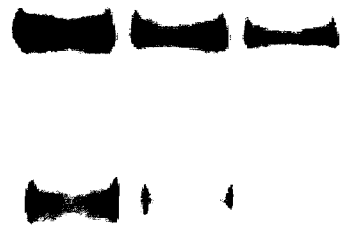

Effect of the ErbB peptides on biochemically defined dimerization of native full-length ErbB receptors was studied using the 32D cell lines transfected with different erbB receptors. 32D-E1 cells were transfected with erbB1; 32D-E2/E3 with erbB2 and erbB3; and 32D-E2/E4 with erbB2 and erbB4. FIGS. 5A and 5B shows the inhibitory effect of 10 μg/ml B3-S22-APQ and B2-S22-AFA on the heregulin-induced erbB2-erbB4 receptor heteromerization in the 32D-E2/E4 cells. While B3-S22-APQ showed a significant inhibitory effect, B2-S22-AFA completely suppressed dimerization at this concentration. (FIG. 5A.) In contrast, no inhibitory effect was observed for the CD4-G peptide used as a control. The observed inhibition of receptor dimerization by B2-S22-AFA was dose-dependent (FIG. 5B) with an apparent $IC_{50}$ concentration of 0.8 μM. Similar inhibitory effects of B3-S22-APQ and B2-S22-AFA on receptor dimerization were observed in the 32D-E2/E3 cells (data not shown).

Example 5

Biological Activity of the erbB Peptides

MTT Assay

Figure 6:
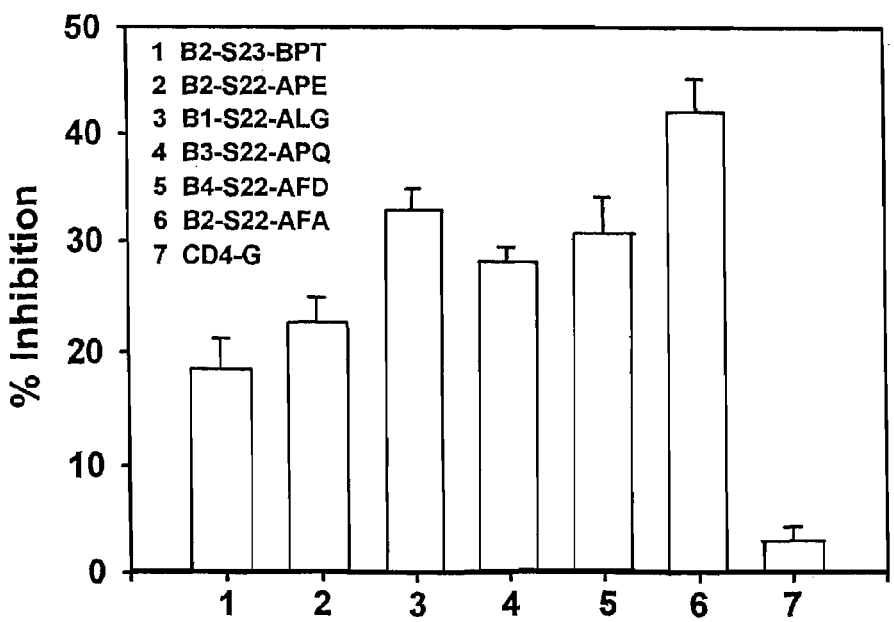
FIG. 6. Inhibitory activity of the erbB peptides against the growth of T6-17 cells studied in an MTT assay.

Biological activity of erbB peptides was evaluated by their ability to inhibit cell proliferation using standard 3,(4,5-dimethylthiazol-2-yl)2,5-diphenyl-tetrazolium bromide) (MTT) assays, as described supra (Hansen et al., J. Immunol. Methods 1989, 119, 203-210). HER2-expressing transformed tumor cells (T6-17) were used for this purpose. (Park et al., Nat Biotechnol. 2000, 18, 194-198). In MTT assays, the peptides inhibited the growth of T6-17 cells, an erbB2-overexpressing transformed cell line, dose-dependently at concentrations ranging from 0.01 to 10 μg/ml. (FIG. 6.) Biological activity of erbB peptides at the optimal concentration of 1 μg/ml was assessed. Each value represents an average of at least four samples. All peptides show inhibitory effects on cell growth. (FIG. 6.) B2-S22-AFA, which has the highest erbB2 receptor-binding affinity (Table 1), was also the most active peptide in the MTT assay. (FIG. 6.)

Figure 7B:
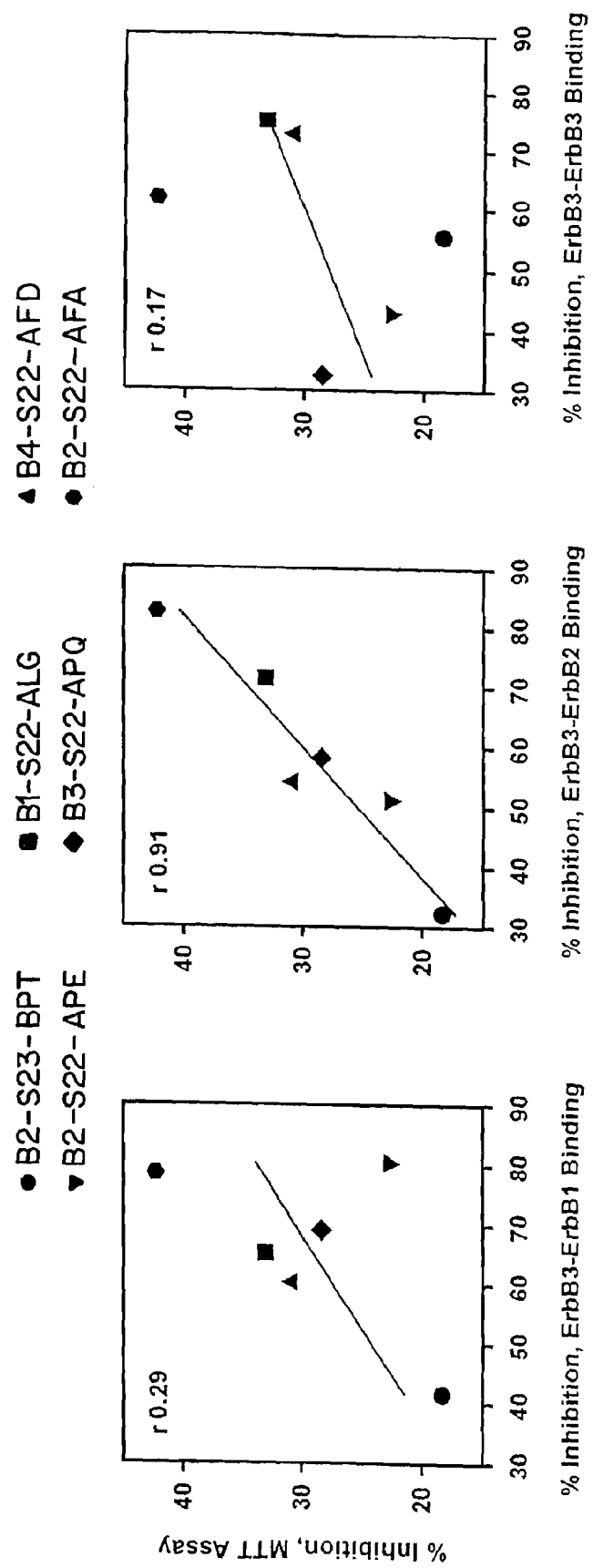

To determine if the observed biological activities of erbB2 peptides against T6-17 cells correlated with their receptor-binding properties or their inhibitory activity on receptor-receptor interactions, the binding data shown in Table 1 and Table 2 were plotted against the MTT assay data for all studied peptides. (FIGS. 7A and 7B.) There was a strong correlation (r=0.92) between the biological activity and binding affinity to erbB2. Correlation with binding affinities to other erbB receptors (erbB1 and erbB3) was insignificant (r=0.21 and 0.44, respectively). Similarly, a strong correlation (r=0.91) has been observed between the cell-suppressing activity and inhibitory activity against erbB3-erbB2 interactions, but not against erbB3-erbB1 (r=0.29) or erbB3-erbB3 (r=0.17) interactions (FIG. 7B).

Effect on the Viability of 32D Cell Lines.

Figure 8A:
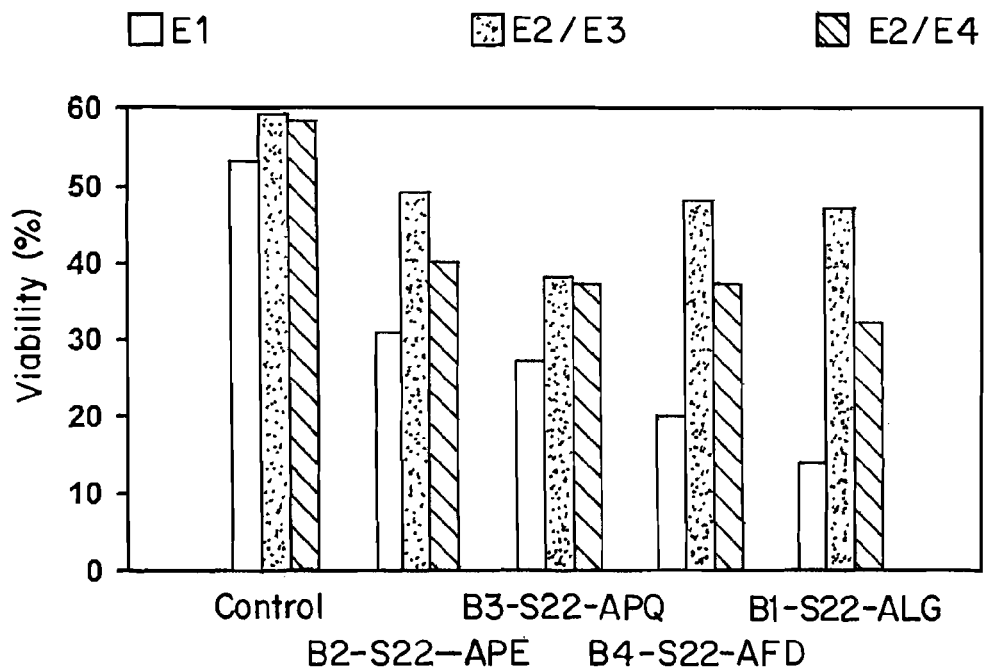
FIG. 8A-B. Inhibitory effect of the ErbB peptides on cell survival of the 32D cell transfectants. 32D cell transfectants were grown in either the ErbB ligand medium (A) or the Il-3 supplement (WEHI) medium (B), and cell viability was determined as described in the Experimental Procedures. In each experiment, the standard error did not exceed 10%.
Figure 8B:
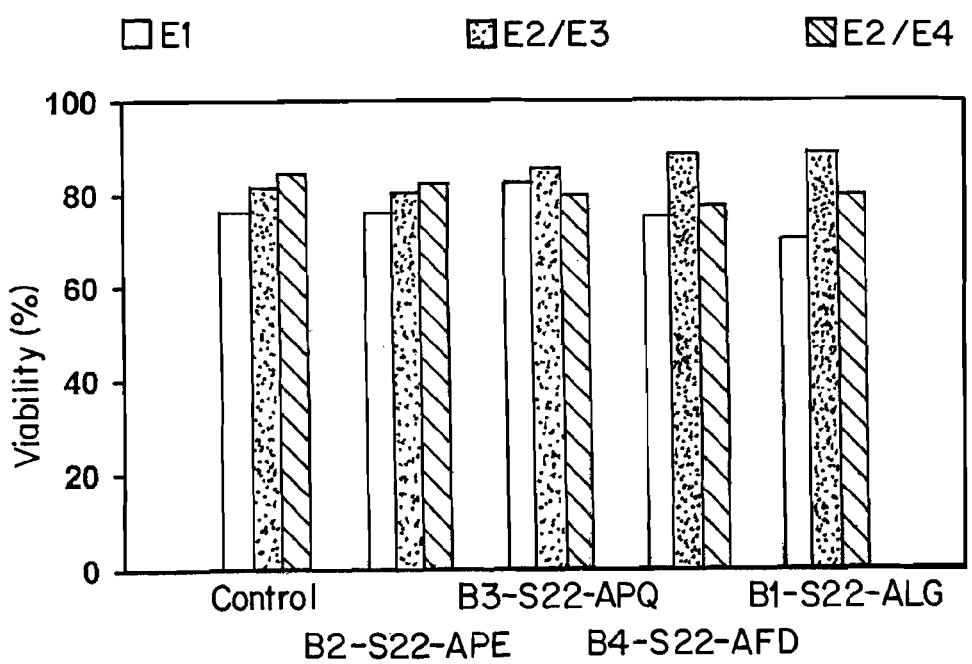
Figure 9A:
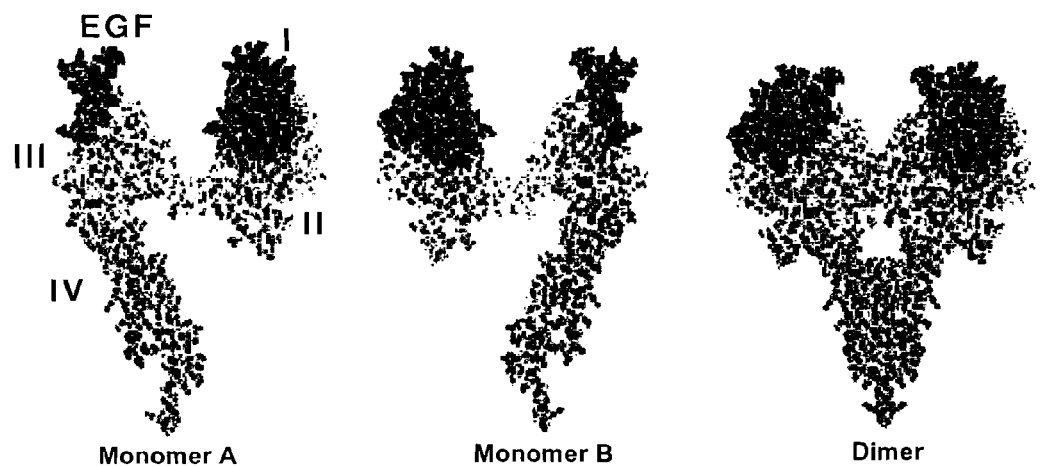
FIG. 9A-B. Molecular modeling of erbB1 homo-dimerization. Possible arrangement of the erbB1-EGF (2:2) complex according to model 1 (EGF cross-links two erbB1 monomers, A) and model 2 (EGF binds to one erbB1 monomer, B).
Figure 9B:
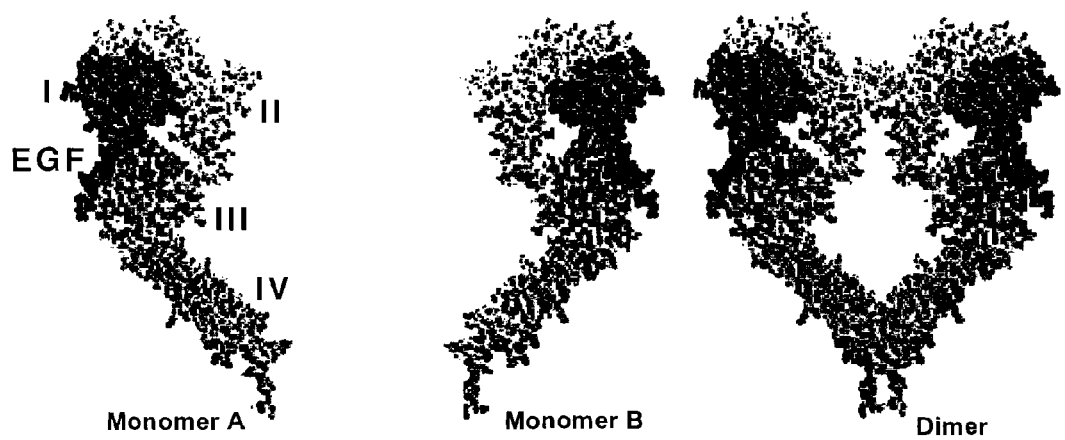

Inhibitory effects of the erbB peptides on cells over-expressing erbB receptors was tested using the 32D cell lines. Transfection of 32D cells with erbB receptors created transfectants capable of growing in a medium containing either EGF (32D-E1), HRGβ1 (32D-E2/E3 and 32D-E2/E4) or IL3 (supplement WEHI medium, all three cell lines). (Wang et al., Proc. Natl. Acad. Sci. USA 1998, 95, 6809-6814.) FIG. 8A shows the effect of different erbB peptides on the viability of the 32D transfectants grown in the erbB ligand medium. The strongest inhibitory effect was observed for the 32D-E1 cells (grown in the EGF medium). Effect on the 32D-E2/E3 and 32D-E2/E4 cells (grown in the HRGβ1 medium) was less pronounced but also significant (FIG. 8A). However, when same cell lines were grown in the IL3 supplement WEHI medium, no significant effect on cell viability could be detected for any of the studied peptides (FIG. 8B), confirming that the observed inhibition of cell survival by the ErbB peptides is mediated by their specific effect on the ErbB receptor signaling but not on IL-3-related signaling.

ErbB peptides described in this study represent constrained mimics of the loops or repeats present in the subdomain IV of the erbB receptors and based on our molecular modeling studies, show a high degree of structural similarity with the template receptor regions. The interactions observed for the erbB peptides are also displayed by the corresponding sites of the native erbB receptors and play a certain role in their metabolic activity. Information obtained for the B2-S23-BTE peptide is especially valuable. Unlike other designed erbB peptides, it does not mimic a single loop, but rather represents a C-terminal membrane-proximal portion of the erbB2 ectodomain. Thus, since the C-terminal portion of erbB2 (B2-S23-BPT) can bind to all three studied erbB receptors (Table 1), this property is also likely to be expected from the full-length native erbB2 receptor. The fact that erbB peptides are not specific to any particular erbB receptor but are highly specific to the erbB family (Table 1), suggests that the C-terminal part of subdomain IV is a receptor-receptor interaction site shared by all erbB receptors. Since all erbB peptides could bind to their respective parental receptor and to other erbB receptors (Table 1), these sites can participate in both homo- and heteroreceptor self-associations.

The observed inter-receptor interactions involving the C-terminal portion of subdomain IV are important for receptor function. The inhibition by the erbB peptides resulted in a dramatic suppression of the cell growth. Significant correlation was found between peptides binding to erbB2, their inhibition of erbB3-erbB2 binding, and their inhibitory activity against erbB2-overexpressing T6-17 cells in the MTT assay.

The observed biological activities of erbB peptides were mediated by their binding to the erbB2 receptor and by blocking receptor-receptor interactions that involve erbB2. erbB peptide-induced inhibition of cell growth in 32D cells transfected with erbB receptors has also been shown to be specifically mediated by the erbB receptor pathway. Indeed, strong inhibition of cell growth has been observed only when the cells were grown in the erbB ligand medium. In contrast, no inhibition occurred via an erbB receptor-independent pathway when the cells were grown in the IL3 supplement (WEHI) medium.

In summary, erbB receptor signaling can be inhibited by rationally designed interface peptide mimetics derived from the subdomain IV of erbB receptor ectodomains. The mimetics specifically bind to the receptors of the erbB family and block inter-receptor interactions which leads to the growth inhibition of HER2-overexpressing cells in vitro. Since all four erbB receptors represent a therapeutic target, peptide mimetics that selectively bind to this receptor family and disable their activity could have an advantage over drugs that are specific to a single member of the erbB family. The study also demonstrates the importance of the C-terminal part of subdomain IV for receptor-receptor interactions involved in signaling by erbB family members.

Example 6

Solubility and Stability of S22-AFA Analogs

Enhancement of solubility of S22-AFA analogs can be accomplished by modifying certain residues that should not affect activity. The following changes (boldface) are made to increase the solubility:

(1) YCF(Y)PDEEGACY-OH (SEQ ID NO: 3; SEQ ID NO: 12)

(2) YCFPDEEGACYK-NH₂ (SEQ ID NO: 25)

(3) YCFPDEEGACYGGS (SEQ ID NO: 26)

(4) GGSYCFPDEEGACY-NH₂ (SEQ ID NO: 6)

Example 7

Creation of Mab which Bind to Interaction Surfaces

MAb specific to dimerization domains are made from: (1) Recombinantly purified p185 subdomain IV fragment; (2) Improved S22-AFA analogs; and (3) other immunogens. Using both the subdomain IV fragment and cysteine-knot peptides will yield high quality cross-reactive MAb. These species are used to immunize Balb/c mice to create a specific dimer surface inhibitory monoclonal species. S22-AFA is coupled to a carrier species as described previously (Jacob, et al, 1985; Williams, et al, 1989, J. Immunol., 142: 4392-4400; Christodoulides, et al, 1993, J. Genetic Microbiology, 139: 1729-1738). The subdomain IV fragment is used as is. Mab production employs a scheme described previously (Drebin, et al. 1986, Symp Fundam Cancer Res, 38:277-289; Drebin, et al. 1986, Proc Natl Acad Sci USA 83:9129-9133). Briefly, BALB/c (H-2$^d$) mice will be immunized with 100 μg of the most efficacious S22-AFA species or soluble subdomain IV (in equal volumes of complete Freund's adjuvant) subcutaneously and then boosted 3 times intraperitoneally with 50 μg/injection. Three days after the final boost, fusions are performed using spleen cells and the fusion partner Sp2/0-Ag14. Screening of fusions will employ an ELISA with S22-AFA deposited in the wells. Other screening assays to be used include FACS analysis of T6-17 cells expressing HER2/neu.

MAb are generated and selected for their ability to bind S22-AFA peptide forms and to bind to Her2/neu on cells and are evaluated functionally in vitro in anchorage independent and dependent type studies.

MAb are evaluated for in vivo effects on tumors using EGFr, Her2/neu, and EGFr and Her2/neu transformed cells (see above). 100 μg MAb is administered by intraperitoneal injection three times a week from the day of tumor xenograft. Injection of irrelevant anti-CD4 MAb or PBS serves as a control Inhibiting the formation of oligomeric receptor forms will affect phenotype. The effect of co-treatment with doxorubicin/adriamycin which has been shown an increased effect on cells treated with antibodies (Park et al., Nat Biotechnol. 2000, 18, 194-198) is also examined. Tumor growth is monitored by volume measurement.

Example 8

Development of Cystein Rich Domain (CRD) Reactive Monoclonal Antibodies

Cell lines transfected with erbB constructs are used as immunogens to create cysteine rich domain reactive MAb that are compared with the mimetics in terms of biological activity. NR6 cells transfected with pTex3-4, pTex4 and pTec6CN (See FIG. 1A and Kumagai et al, 2001) are used as immunogens. The fusion scheme is as described previously (Drebin, et al. 1986, Symp Fundam Cancer Res 38:277-289; Drebin, et al. 1986, Proc Natl Acad Sci USA 83:9129-9133). Briefly, BALB/c (H-2$^d$) mice are immunized with the cell line subcutaneously and then boosted 3 times intraperitoneally with 10$^7$ cells. Three days after the final boost, fusions are performed using spleen cells and the fusion partner Sp2/0-Ag14. The SP2/0-Ag14 fusion partner secretes no free light chain. Hybridoma cell lines will be screened by FACS analysis against pNeu, pTex3, pTex3-4 (subdomains III and IV), pTex4 (subdomain IV only) and pTex6CN. Controls include NR6 cells, cells which express EGFr alone and pNex1, 2, and 3 (subdomains I, II, and III) and a cell line that expresses only subdomain I, pTex1 cells. Cell lines provide an unambiguous screening array for this class of MAb. Colonies producing antibodies of the desired specificity are subcloned three times by limiting dilution. Subtypes for MAb are identified using the Mouse Monoclonal Antibody Subtyping Kit (Gibco BRL).

Experimental Procedures.

Peptide Synthesis and Cyclization

Linear peptides (95% purity) were ordered from the Protein Chemistry Laboratory, University of Pennsylvania. Peptide purity and identity was confirmed by reverse phase high performance liquid chromatography (RP HPLC) and MALDI mass-spectrometry, using a time-of-flight mass spectrometer (MicroMass TofSpec; Micromass Inc., Beverly, Mass.). The peptides were cyclized by air oxidation in distilled water adjusted to pH 8.0 with (NH$_4$)$_2$CO$_3$ at 0.1 mg/ml and 4° C. Progress of the oxidation was controlled by measuring amounts of free thiols with 5,5'-dithio-bis(2-nitrobenzoic acid (DTNB). Briefly, 0.4 ml of a peptide (0.1 mg/ml) and 5 μl of DTNB (20 mM) were added to 0.2 ml of 0.1M sodium phosphate buffer, pH 8.0. Absorbance at 412 nm was measured and compared with the linear unoxidized peptides. The cyclized peptides were lyophilized and their purity analyzed by RP HPLC using a C18 semi-preparative column (Waters, Milford, Mass.). Typically, purity of higher than 95% was obtained for the cyclized peptides. Aliquotes of 1 mM stock solutions have been prepared for each peptide and kept at −20° C. to be thawed prior to the binding or bioassay studies. Peptide concentrations were confirmed by UV spectrofotometry using extinction coefficients at 280 nm calculated for each peptide as described in Gill et al., (Anal Biochem 1989, 182, 319-326).

Expression of the GST Fusion Protein of Subdomain IV of erbB2.

The DNA fragment encoding the subdomain IV of erbB2 (erbB2-SbdIV) was generated by polymerase chain reaction. The upstream primer was 5'-CGCCCGGATCCTGGCCT-GCCACCAGCTGTGC-3' [SEQ ID NO: 44] and the downstream primer was 5'-CGCCCGCGGCCGCCGCAGAGAT-GATGGAGTCAG-3'. [SEQ ID NO: 45] These two primers were designed to include BamHI and Not I restriction sites, respectively, for inframe insertion into the BamHI/Not I linearized pGEX-5X-3 vector. Recombinant vector was used to infect Escherichia coli BL-21 (DE3). 100 ml of the 2XYT medium were inoculated with 10 ml of the overnight culture and grown at 37° C. until the $OD_{600}$ of 0.4-0.5 was reached. IPTG was added to the medium at the final concentration of 0.1 mM and grown for 2 hrs. The cells were spun down by centrifugation at 4,000 g for 10 min and resuspended with 5 ml of cold PBS (with DTT, PMSF and aprotinin at the final concentration of 5 mM, 1 mM and 1 µg/ml respectively). After sonication on ice, Triton X-100 was added to the final concentration of 1% and the solution was rocked at 4° C. for 1 hr and centrifuged at 10,000 g for 10 min. 100 µl of glutathione sepharose bead was then added to the supernatant. It was rocked at 4° C. for 2-4 hrs, centrifuged and washed three times with PBS. 100 µl elution buffer was added followed by rotation for 10 min at room temperature, centrifugation at 300 g for 1 min and collection of the supernatant. Elutions were repeated three times and combined.

Interaction Studies

Binding experiments were performed with the surface plasmon resonance based biosensor instrument Biacore 3000 (Biacore AB, Uppsala, Sweden), at 25° C. Recombinant purified erbB receptors were provided by Dr. Che Law, Xcyte Therapeutics, Seattle, Wash. (erbB2) and Dr. Mark A. Lemmon, Department of Biochemistry and Biophysics, University of Pennsylvania School of Medicine (erbB1 and erbB3). Immobilization of the erbB receptors in the sensor surface was performed following the standard amine coupling procedure according to manufacturer's instructions. Briefly, 35 µl of a solution containing 0.2 M N-ethyl-N'-(dimethylamino-propyl)carbodiimide (EDC) and 0.05 M N-hydroxysuccinimide (NHS), were injected at a flow rate of 5 µl/min to activate carboxyl groups on the sensor chip surface. Receptors (40 ng/ml in 10 mM NaOAc buffer, pH 5.0) were flowed over the chip surface at a flow rate of 20 µl/min until the desired level bound protein was reached. Unreacted protein was washed out and unreacted activated groups were blocked by the injection of 35 µl of 1 M ethanolamine at 5 µl/min. The final immobilization response of each receptor was 3,500 RU. A reference surface was generated simultaneously under the same conditions but without receptor injection and used as a blank to correct for instrument and buffer artifacts. Peptides were injected at variable concentrations at 20 µl/min flow rate and binding to the receptors immobilized on the chip was monitored in real time. Each sensorgram consists of an association phase (first 240 s), reflecting binding of the injected peptide to the receptor, followed by a dissociation phase (300 s), during which the running buffer is passed over the chip and the bound peptide is being washed off the receptor surface.

MTT Assay

The MTT assay has been used for measuring cell growth as previously described in Hansen et at (J. Immunol. Methods 1989, 119, 203-210). Briefly, T6-17 cells were seeded in 96-well plates overnight in DMEM containing 10% FBS (1000 per well). T6-17 is derived from NIH3T3 by overexpressing the human erbB2 receptor. Cells were cultured in 100 µl of fresh medium containing 1 µg/ml of erbB peptides for 48 hours. This incubation time was optimal for measuring inhibitory effects of different analogs. No improvements in the inhibitory activity could be achieved by increasing the incubation period. 25 µl of MTT solution (5 mg/ml in PBS) were added to each well, and after 2 hours of incubation at 37° C., 100 µl of the extraction buffer (20% w/v of SDS, 50% N,N-dimethyl formamide, pH 4.7) were added. After an overnight incubation at 37° C., the optical density at 600 nm was measured using an ELISA reader.

Cell Viability and Crosslinking Analysis on 32D Cell Lines.

32D cell transfectants with ErbB receptors (gift from Dr. Jacalyn H. Pierce, National Cancer Institute) were grown in RPMI 1640, 10% FBS and 5% WEHI medium (GenoQuest, Interlukin-3 supplement) and respective antibiotics, i.e. 32D-E1 (gptr), 32D-E2/E3 (neor/gptr) and 32D-E2/E4 (neor/gptr) (29). The WEHI medium was withdrawn and cells were pre-incubated with ErbB peptides for 2 hours at 37° C. before adding 10 µg/ml EGF (for 32D-E1, Collaborative Biomedical Products) or 10 µg/ml HRG □1 (for 32D-E2/E3 or 32D E2/E4, R&D Systems) and further incubated at 37° C. for 24-48 hours. The cell viability was detected with propidium iodide staining followed by flow cytometry quantification. For the cross-linking analysis, approximately 2×106 cells were suspended in RPMI 1640 medium containing 0.1% BSA and 10 mM HEPES, and pre-incubated with ErbB peptides for 2 hours at 37° C. before adding 10 µg/ml EGF or 10 µg/ml Heregulin-β1 EGF domain and further incubated at 37° C. for 10-15 minutes. Cells were rinsed with PBS and incubated in 2 mM $BS^3$/PBS at 4° C. for 45 minutes. Cell lysate was immunoprecipitated with anti-ErbB2 or anti-ErbB3 antibody (Santa Cruz), and immunobloted with anti-pTyr (PY20, Santa Cruz).

Model Building.

Homology modeling of erbB2-SbdIV and erbB1 ectodomain was performed with Quanta/Protein design (Molecular Simulations Inc.) on the basis of template crystal structures of laminin g1III3-5 (1KLO) for erbB2-SbdIV and insulin-like growth factor-1 receptor (1IGR) for erbB1. The sequences were aligned manually using the Sequence Viewer by matching positions of conservative cysteine residues and inserting gaps to adjust the lengths of the inter-cysteine spacings. Frameworks for the molecular models were generated by using coordinates from the template structures for manually selected matching residues of the modeled proteins. Missing coordinates for peptide segments that did not have counterpart in the template structures were calculated by either "Regularizing Region" and "Model Side Chains" tools (for short loops) or by modeling loop conformation using a "Congen" (Li et al., 1997, Protein Sci., 6, 956-970; Tejero, R., et al., 1996, Protein Sci., 5, 578-592) program (for longer loops). The final monomeric structures were then obtained by running the CHARMm energy minimization in the RTF mode. To construct a dimeric erbB1-EGF model, the following assumptions were made based on the existing experimental evidence: erbB1-EGF complex has a 2:2 stoichiometry (Lemmon M. A., et al., 1997, EMBO J., 16, 281-294); the C-terminal part of subdomain IV is a dimeric interaction site (based on our results described below); the N-terminus of bound EGF is close (within about 15 Å) to Tyr101 (subdomain I) of erbB1 (Woltjer, R. L., et al., 1992, Proc. Natl. Acad. Sci. USA, 89, 7801-7805; the C-terminal Arg45 of bound EGF is close (within about 15 Å) to Lys465 (subdomain III) of erbB1 (Summerfield, A. E., et al., 1996, J. Biol. Chem., 271, 19656-19659; the N-terminus of EGF bound to erbB1 is about 67 Å (from 52 to 82 Å) away from the membrane surface (Carraway, K. L., 1990, Biochem., 29, 8741-8747; maximal dimensions of erbB1 are about 110 Å for the monomer and 120 Å for the dimer (Tejero, R., et al., 1996, Protein Sci., 5, 578-592); EGF binds to the second face of subdomain III (Jorissen, R. N., 2000, Protein Sci., 9, 310-324. Orientations of complex-forming two erbB1 and two EGF (PDB code, 3EGF) molecules were adjusted manually to satisfy the criteria listed above based on two different models of the complex arrangement. The final dimeric models were minimized using the CHARMm energy minimization tool. These dimeric complex models have a low resolution nature and may have a degree of error in the positioning of the constituent molecules with respect to each other.

As those skilled in the art will appreciate, numerous changes and modifications may be made to the preferred embodiments of the invention without departing from the spirit of the invention. It is intended that all such variations fall within the scope of the invention.

The entire disclosure of each patent, patent application, or other publication cited herein is hereby incorporated by reference.

LITERATURE CITED

O'Rourke, D. M., Qian, X., Zhang, H.-T., Nute, E., Meinkoth, J., and Greene, M. I. Trans receptor inhibition of human glioblastoma cells by erbB family ectodomains., Proc. Nat. Acad. Sci., 94(7), 3250-3255, 1997.

Qian, X., O'Rourke, D. M., Zhao, H., and Greene, M. I., Inhibition of p185$^{neu}$ kinase activity and cellular transformation by co-expression of a truncated neu protein. Oncogene, 13: 2149-2157, 1996.

Qian, X., O'Rourke, D. M., Drebin, J., Zhao, H., Wang, Q., and Greene, M. I.: Identification of p185 sequences required for monoclonal antibody- or ligand-mediated receptor signal attenuation. DNA, 16(12): 1395-1405, 1998.

Zhang, H. T., O'Rourke, D., Zhao, H., Murali, R., Mikami, Y., Davis, J. G., Greene, M. I., and Qian, X.: Absence of autophosphorylation site Y882 in the p185neu oncogene product correlates with a reduction of transforming potential. Oncogene, 16: 2835-2842, 1998.

O'Rourke, D., Nute, E. J. L., Davis, J. G., Wu, C., Lee, A., Murali, R., Zhang, H. T., Qian, X., Kao, C. C., Greene, M. I.: Inhibition of a naturally occurring EGFr oncoprotein by the p185neu ectodomain: implications for subdomain contributions to receptor assembly. Oncogene, 16: 1197-1207, 1998.

Qian, X., O'Rourke, D. M., Fei, Zhizhong, Zhang, H. T., Kao, C., Greene, M. I.: Domain-specific interactions between the p185 neu and EGF receptor kinases determine differential signalling outcomes. Journal of Biological Chemistry, 274:574-583, 1999.

O'Rourke, D., Kao, G. D., Singh, N., Park, B., Muschel, R. J., Wu, C., Greene, M., Conversion of a radioresistant phenotype to a more sensitive one by disabling erbB receptor signaling in human cancer cells. Proc. Nat. Acad. Sci. (USA), 95: 10842-10847, 1998.

Peterson, N., and Greene, M. I. Bacterial Expression and Characterization of Recombinant Biologically-Active Anti-Tyrosine Kinase Receptor Antibody-Forms. DNA, 17: 1031-1040, 1998.

Park, B., O'Rourke, D., Wang, Q., Davis, J., Post, A. and Greene, M. I. Induction of the Tat-binding protein 1 gene accompanies the disabling of oncogenic erbB receptor tyrosine kinases. Proc. Nat. Acad. Sci. (USA), 96:6434-6438, 1999.

Wu, C., Chen, Z., Ullrich, A., Greene, M. I., and O'Rourke, D, Inhibition of EGFR-mediated phosphoinositide-3-OH kinase (PI3-K) signaling and glioblastoma phenotype by Signal-Regulatory Proteins (SIRPs). Oncogene, 19:3999-4010, 2000.

Park, B. W., Zhang, H. T., Wu, C., Berezov, A., Zhang, X., Dua, R., Wang, Q., Kao, G., O'Rourke, D., Greene, M. I. and Murali, R.: Rationally designed anti-HER2/neu peptide mimetic disables p185$^{HER2/neu}$ tyrosine kinases in vitro and in vivo. Nature (*Biotechnology*), 18: 194-198, 2000.

Zhang, H., Wang, Q., Montone, K., Peavey, J., Drebin, J. A., Greene, M. I. and Murali, R.: Shared antigenic epitopes and pathobiological functions of anti-p185$^{her2/neu}$ monoclonal antibodies. Experimental and Molecular Pathology, 67:15-25, 1999.

Berezov A., Zhang H. T., Greene M. I. and Murali R. Disabling ErbB Receptors with Rationally Designed Exocyclic Mimetics of Antibodies: Structure-Function Analysis. Journal of Medicinal Chemistry, in press, 2001.

Kumagai T, Davis J G, Horie T, O'Rourke D and Greene M. I. The role of distinct p185 extracellular subdomains for dimerization with the epidermal growth factor receptor and EGF mediated signaling Proc. Nat. Acad. Sci. (USA), 98, 5526-5531, 2001.

Zhang, H. T., Kacharmina, J. E., Miyashiro, K., Greene, M. I., and Eberwine, J. Protein Quantification from Complex Protein Mixtures Using a Novel Proteomics Methodology with Single Cell Resolution, Proc. Natl. Acad. Sci., 98, 5497-5502, 2001.

Brennan, P. J., Kumagai, T., Berezov, A., Murali, R., and Greene, M. I. HER2/Neu: mechanisms of dimerization/oligomerization, Oncogene, 19: 6093-6101, 2000.

Alroy, I. & Yarden, Y. (1997) The ErbB signaling network in embryogenesis and oncogenesis: signal diversification through combinatorial ligand-receptor interactions *FEBS Lett* 410, 83-6.

Bach, A. C., Eyermann, C. J., Gross, J. D., Bowe, r. M. J., Harlow, R. L., Weber, P. C. & DeGrado, W. F. (1994) Structural Studies of a Family of High Affinity Ligands for GPIIb/IIIa *Journal of American Chemical Society* 116, 3207-3219.

Banner, D. W., D'Arcy, A., Janes, W., Gentz, R., Schoenfeld, H. J., Broger, C., Loetscher, H. & Lesslauer, W. (1993) Crystal structure of the soluble human 55 kd TNF receptor-human TNF beta complex: implications for TNF receptor activation *Cell* 73, 431-45.

Baselga, J., Norton, L., Albanell, J., Kim, Y. M. & Mendelsohn, J. (1998) Recombinant humanized anti-HER2 antibody (Herceptin) enhances the antitumor activity of paclitaxel and doxorubicin against HER2/neu overexpressing human breast cancer xenografts *Cancer Res* 58, 2825-2831.

Blain, S. W., Montalvo, E. & Massague, J. (1997) Differential interaction of the cyclin-dependent kinase (Cdk) inhibitor p27Kip1 with cyclin A-Cdk2 and cyclin D2-Cdk4 *J Biol Chem* 272, 25863-72.

Brennan, P. J., Kumogai, T., Berezov, A., Murali, R. & Greene, M. I. (2000) HER2/Neu: mechanism of dimerization/oligomerization *Oncogene* 19, 6093-6101.

Britsch, S., Li, L., Kirchhoff, S., Theuring, F., Brinkmann, V., Birchmeier, C. & Riethmacher, D. (1998) The ErbB2 and ErbB3 receptors and their ligand, neuregulin-1, are essential for development of the sympathetic nervous system *Genes Dev* 12, 1825-36.

Brown, V. I., Shah, N., Smith, R., Hellman, M., Jarett, L., Mikami, Y., Cohen, E., Qian, X. & Greene, M. I. (1994)

Demonstration by two-color flow cytometry that tyrosine kinase activity is required for down-modulation of the oncogenic neu receptor *DNA Cell Biol* 13, 193-209.

Burgess, K., Li, W. & Lim, D. (1996) in *Solid phase syntheses of peptidomimetics*. (American Chemical Society, Washington, D, pp. ORGN-157.

Cambier, J. C. (1997) Inhibitory receptors abound? *Proc Natl Acad Sci USA* 94, 5993-5.

Carraway, K. L., 3rd & Cantley, L. C. (1994) A neu acquaintance for erbB3 and erbB4: a role for receptor heterodimerization in growth signaling *Cell* 78, 5-8.

Carter, P., Presta, L., Gorman, C. M., Ridgway, J. B., Henner, D., Wong, W. L., Rowland, A. M., Kotts, C., Carver, M. E. & Shepard, H. M. (1992) Humanization of an anti-p185HER2 antibody for human cancer therapy *Proceedings of the National Academy of Sciences of the United States of America* 89, 4285-9.

Chang, H., Riese, D. J., 2nd, Gilbert, W., Stern, D. F. & McMahan, U. J. (1997) Ligands for ErbB-family receptors encoded by a neuregulin-like gene *Nature* 387, 509-12.

Chiri, S., De Nadai, C. & Ciapa, B. (1998) Evidence for MAP kinase activation during mitotic division *J Cell Sci* 111, 2519-2527.

Chothia, C. & Lesk, A. M. (1987) Canonical structures for the hypervariable regions of immunoglobulins *J Mol Biol* 196, 901-17.

Christodoulides, M., McGuinness, B. T. & Heckels, J. E. (1993) Immunization with synthetic peptides containing epitopes of the class 1 outer-membrane protein of *Neisseria meningitidis*: production of bactericidal antibodies on immunization with a cyclic peptide *Journal of Genetic Microbiology* 139, 1729-1738.

D'Ambrosio, D., Fong, D. C. & Cambier, J. C. (1996) The SHIP phosphatase becomes associated with Fc gammaRIIB1 and is tyrosine phosphorylated during 'negative' signaling *Immunol Lett* 54, 77-82.

Daeron, M., Latour, S., Malbec, O., Espinosa, E., Pina, P., Pasmans, S. & Fridman, W. H. (1995) The same tyrosine-based inhibition motif, in the intracytoplasmic domain of Fc gamma RIIB, regulates negatively BCR-, TCR-, and FcR-dependent cell activation *Immunity* 3, 635-46.

Dahia, P. L., Aguiar, R. C., Honegger, J., Fahlbush, R., Jordan, S., Lowe, D. G., Lu, X., Clayton, R. N., Besser, G. M. & Grossman, A. B. (1998) Mutation and expression analysis of the p27/kip1 gene in corticotrophin-secreting tumours *Oncogene* 16, 69-76.

Deb, T. B., Wong, L., Salomon, D. S., Zhou, G., Dixon, J. E., Gutkind, J. S., Thompson, S. A. & Johnson, G. R. (1998a) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation *J Biol Chem* 273, 16643-6.

Deb, T. B., Wong, L., Salomon, D. S., Zhou, G., Dixon, J. E., Gutkind, J. S., Thompson, S. A. & Johnson, G. R. (1998b) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation *J Biol Chem* 273, 16643-16646.

Deveraux, Q. L., Takahashi, R., Salvesen, G. S. & Reed, J. C. (1997) X-linked IAP is a direct inhibitor of cell-death proteases *Nature* 388, 300-4.

Di Cristofano, A., Kotsi, P., Peng, Y. F., Cordon-Cardo, C., Elkon, K. B. & Pandolfi, P. P. (1999) Impaired Fas response and autoimmunity in Pten+/− mice *Science* 285, 2122-5.

Di Cristofano, A. & Pandolfi, P. P. (2000) The multiple roles of PTEN in tumor suppression *Cell* 100, 387-90.

Dougall, W. C., Qian, X., Peterson, N. C., Miller, M. J., Samanta, A. & Greene, M. I. (1994) The neu-oncogene: signal transduction pathways, transformation mechanisms and evolving therapies *Oncogene* 9, 2109-2123.

Drebin, J. A., Link, V. C. & Greene, M. I. (1988) Monoclonal antibodies reactive with distinct domains of the neu oncogene-encoded p185 molecule exert synergistic anti-tumor effects in vivo *Oncogene* 2, 273-277.

Drebin, J. A., Link, V. C., Stern, D. F., Weinberg, R. A. & Greene, M. I. (1985) Down-modulation of an oncogene protein product and reversion of the transformed phenotype by monoclonal antibodies *Cell* 41, 697-706.

Drebin, J. A., Link, V. C., Stern, D. F., Weinberg, R. A. & Greene, M. I. (1986a) Development of monoclonal antibodies reactive with the product of the neu oncogene *Symp Fundam Cancer Res* 38, 277-289.

Drebin, J. A., Link, V. C., Weinberg, R. A. & Greene, M. I. (1986b) Inhibition of tumor growth by a monoclonal antibody reactive with an oncogene-encoded tumor antigen *The Proceedings of the National Academy of Science USA* 83, 9129-9133.

Drebin, J. A., Stern, D. F., Link, V. C., Weinberg, R. A. & Greene, M. I. (1984) Monoclonal antibodies identify a cell-surface antigen associated with an activated cellular oncogene *Nature* 312, 545-548.

Dudek, H., Datta, S. R., Franke, T. F., Birnbaum, M. J., Yao, R., Cooper, G. M., Segal, R. A., Kaplan, D. R. & Greenberg, M. E. (1997) Regulation of neuronal survival by the serine-threonine protein kinase Akt *Science* 275, 661-5.

Eck, M. J. & Sprang, S. R. (1989) The structure of tumor necrosis factor-alpha at 2.6 A resolution. Implications for receptor binding *J Biol Chem* 264, 17595-605.

Eck, M. J., Ultsch, M., Rinderknecht, E., de Vos, A. M. & Sprang, S. R. (1992) The structure of human lymphotoxin (tumor necrosis factor-beta) at 1.9-A resolution *J Biol Chem* 267, 2119-22.

Eigenbrot, C., Gonzalez, T., Mayeda, J., Carter, P., Werther, W., Hotaling, T., Fox, J. & Kessler, J. (1994) X-ray structures of fragments from binding and nonbinding versions of a humanized anti-CD18 antibody: structural indications of the key role of VH residues 59 to 65 *Proteins* 18, 49-62.

Eigenbrot, C., Randal, M., Presta, L., Carter, P. & Kossiakoff, A. A. (1993) X-ray structures of the antigen-binding domains from three variants of humanized anti-p185HER2 antibody 4D5 and comparison with molecular modeling *J Mol Biol* 229, 969-995.

Erickson, S. L., O'Shea, K. S., Ghaboosi, N., Loverro, L., Frantz, G., Bauer, M., Lu, L. H. & Moore, M. W. (1997) ErbB3 is required for normal cerebellar and cardiac development: a comparison with ErbB2- and heregulin-deficient mice *Development* 124, 4999-5011.

Feng, G. S. (1999) Shp-2 tyrosine phosphatase: signaling one cell or many *Exp Cell Res* 253, 47-54.

Ferguson, K. M., Darling, P. J., Mohan, M. J., Macatee, T. L. & Lemmon, M. A. (2000) Extracellular domains drive homo- but not hetero-dimerization of erbB receptors *Embo J* 19, 4632-43.

Fujioka, Y., Matozaki, T., Noguchi, T., Iwamatsu, A., Yamao, T., Takahashi, N., Tsuda, M., Takada, T. & Kasuga, M. (1996) A novel membrane glycoprotein, SHPS-1, that binds the SH2-domain-containing protein tyrosine phosphatase SHP-2 in response to mitogens and cell adhesion *Molecular and Cellular Biology* 16, 6887-99.

Furnari, F. B., Huang, H. J. & Cavenee, W. K. (1998) The phosphoinositol phosphatase activity of PTEN mediates a serum-sensitive G1 growth arrest in glioma cells *Cancer Res* 58, 5002-8.

Furnari, F. B., Lin, H., Huang, H. S. & Cavenee, W. K. (1997) Growth suppression of glioma cells by PTEN requires a functional phosphatase catalytic domain *Proc Natl Acad Sci USA* 94, 12479-84.

Garrett, T. P., McKern, N. M., Lou, M., Frenkel, M. J., Bentley, J. D., Lovrecz, G. O., Elleman, T. C., Cosgrove, L. J. & Ward, C. W. (1998a) Crystal structure of the first three domains of the type-1 insulin-like growth factor receptor *Nature* 394, 395-9.

Garrett, T. P., McKern, N. M., Lou, M., Frenkel, M. J., Bentley, J. D., Lovrecz, G. O., Elleman, T. C., Cosgrove, L. J. & Ward, C. W. (1998b) Crystal structure of the first three domains of the type-1 insulin-like growth factor receptor *Nature* 394, 395-399.

Gasparini, G., Gullick, W. J., Bevilacqua, P., Sainsbury, J. R. C., Meli, S., Boracchi, P., Testolin, A., Lamalfa, G. & Pozza, F. (1992) Human Breast Cancer—Prognostic Significance of the c-erbB-2 Oncoprotein Compared with Epidermal Growth Factor Receptor, DNA Ploidy, and Conventional Pathologic Features *Journal of Clinical Oncology* 10, 686-695.

Goodman, M. & Shao, H. (1996) Peptidomimetic building blocks for drug discovery: an overview *Pure Appl. Chem.* 68, 1303-1308.

Hanessian, S., Mcnaughton-Smith, G., Lombart, H.-G. & Lubell, W. D. (1997) Design and synthesis of conformationally constrained amino acids as versatile scaffolds and peptide mimetics *Tetrahedron* 53, 12789-12854.

Hemmings, B. A. (1997) Aid signaling: linking membrane events to life and death decisions *Science* 275, 628-630.

Huang, G. C., Ouyang, X. & Epstein, R. J. (1998) Proxy activation of protein ErbB2 by heterologous ligands implies a heterotetrameric mode of receptor tyrosine kinase interaction *Biochem J* 331, 113-119.

Huang, H. S., Nagane, M., Klingbeil, C. K., Lin, H., Nishikawa, R., Ji, X. D., Huang, C. M., Gill, G. N., Wiley, H. S. & Cavenee, W. K. (1997) The enhanced tumorigenic activity of a mutant epidermal growth factor receptor common in human cancers is mediated by threshold levels of constitutive tyrosine phosphorylation and unattenuated signaling *J Biol Chem* 272, 2927-35.

Irmler, M., Thome, M., Hahne, M., Schneider, P., Hofmann, K., Steiner, V., Bodmer, J. L., Schroter, M., Burns, K., Mattmann, C., Rimoldi, D., French, L. E. & Tschopp, J. (1997) Inhibition of death receptor signals by cellular FLIP [see comments] *Nature* 388, 190-5.

Jackson, S., Harlow, R., Dwivedi, A., Parthasarathy, A., Higley, A., Krywko, J., Rockwell, A., Markwalder, J., Wells, G., Wexler, R., Mousa, S. & DeGrado, W. F. (1994) Template-constrained cyclic peptides: design of high-affinity ligands for GPIIb/IIIa *Journal of American Chemical Society* 116, 3220-3230.

Jardines, L., Weiss, M., Fowble, B. & Greene, M. (1993) neu(c-erbB-2/HER2) and the epidermal growth factor receptor (EGFR) in breast cancer *Pathobiology* 61, 268-82.

Jacob, C. O., Leitner, M., Zamir, A., Salomon, D. & Arnon, R. (1985) Priming immunization against cholera toxin and *E. coli* heat-labile toxin by a cholera toxin short peptide-beta-galactosidase hybrid synthesized in *E. coli Embo Journal* 4, 3339-3343.

Kauffmann-Zeh, A., Rodriguez-Viciana, P., Ulrich, E., Gilbert, C., Coffer, P., Downward, J. & Evan, G. (1997) Suppression of c-Myc-induced apoptosis by Ras signalling through PI(3)K and PKB *Nature* 385, 544-8.

Kharitonenkov, A., Chen, Z., Sures, I., Wang, H., Schilling, J. & Ullrich, A. (1997) A family of proteins that inhibit signalling through tyrosine kinase receptors *Nature* 386, 181-6.

KieberEmmons, T., Murali, R. & Greene, M. I. (1997) Therapeutic peptides and peptidomimetics *Curr. Opin. Biotechnol.* 8, 435-441.

Kokai, Y., Cohen, J. A., Drebin, J. A. & Greene, M. I. (1987) Stage- and tissue-specific expression of the neu oncogene in rat development *Proc Natl Acad Sci USA* 84, 8498-8501.

Kokai, Y., Myers, J. N., Wada, T., Brown, V. I., LeVea, C. M., Davis, J. G., Dobashi, K. & Greene, M. I. (1989) Synergistic Interaction of p185c-neu and the EGF Receptor Leads to Transformation of Rodent Fibroblasts *Cell* 58, 287-292.

Koskinen, A. M. P. & Hassila, H. (1996) Asymmetric intramolecular cyclopropanation. Synthesis of conformationally constrained aminocyclopropane carboxylic acids *Acta Chem. Scand.* 50, 323-327.

Kramer, R., Bucay, N., Kane, D. J., Martin, L. E., Tarpley, J. E. & Theill, L. E. (1996) Neuregulins with an Ig-like domain are essential for mouse myocardial and neuronal development *Proc Natl Acad Sci USA* 93, 4833-8.

Kuhn, C., Lindeberg, G., Gogoll, A., Hallberg, A. & Schmidt, B. (1997) Fmoc protected peptide mimetic based on a cyclohexane framework and incorporation into angiotensin II *Tetrahedron* 53, 12497-12504.

Kumagai, T., Davis, J. G., Horie, T., O'Rourke, D. M. & Greene, M. I. (2001) The role of distinct p185neu extracellular subdomains for dimerization with the epidermal growth factor (EGF) receptor and EGF-mediated signaling *Proc Natl Acad Sci USA* 98, 5526-31.

Lee, C. C., Ichihara, T., Yamamoto, S., Wanibuchi, H., Sugimura, K., Wada, S., Kishimoto, T. & Fukushima, S. (1999) Reduced expression of the CDK inhibitor p27(KIP1) in rat two-stage bladder carcinogenesis and its association with expression profiles of p21(WAF1/Cip1) and p53 *Carcinogenesis* 20, 1697-1708.

Lee, K. F., Simon, H., Chen, H., Bates, B., Hung, M. C. & Hauser, C. (1995) Requirement for neuregulin receptor erbB2 in neural and cardiac development *Nature* 378, 394-8.

Lees, E. (1995) Cyclin dependent kinase regulation *Curr Opin Cell Biol* 7, 773-80.

Li, F., Ambrosini, G., Chu, E. Y., Plescia, J., Tognin, S., Marchisio, P. C. & Altieri, D. C. (1998) Control of apoptosis and mitotic spindle checkpoint by survivin *Nature* 396, 580-4.

Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H. & Parsons, R. (1997) PTEN, a putative protein tyrosine phosphatase gene mutated in human brain, breast, and prostate cancer *Science* 275, 1943-7.

Liu, X., Hwang, H., Cao, L., Buckland, M., Cunningham, A., Chen, J., Chien, K. R., Graham, R. M. & Zhou, M. (1998) Domain-specific gene disruption reveals critical regulation of neuregulin signaling by its cytoplasmic tail *Proc Natl Acad Sci USA* 95, 13024-9.

Lu, Y., Lin, Y. Z., LaPushin, R., Cuevas, B., Fang, X., Yu, S. X., Davies, M. A., Khan, H., Furui, T., Mao, M., Zinner, R., Hung, M. C., Steck, P., Siminovitch, K. & Mills, G. B. (1999) The PTEN/MMAC1/TEP tumor suppressor gene decreases cell growth and induces apoptosis and anoikis in breast cancer cells *Oncogene* 18, 7034-45.

MacCallum, R. M., Martin, A. C. & Thornton, J. M. (1996) Antibody-antigen interactions: contact analysis and binding site topography *J Mol Biol* 262, 732-45.

Magliani, W., Conti, S., de Bernardis, F., Gerloni, M., Bertolotti, D., Mozzoni, P., Cassone, A. & Polonelli, L. (1997) Therapeutic potential of antiidiotypic single chain antibodies with yeast killer toxin activity *Nat Biotechnol* 15, 155-8.

McIntyre, M., Desdouets, C., C, S. n.-B., Laurent-Winter, C., Lamas, E. & Br chot, C. (1999) Differential expression of the cyclin-dependent kinase inhibitor P27 in primary hepatocytes in early-mid G1 and G1/S transitions *Oncogene* 18, 4577-85.

Meyer, D. & Birchmeier, C. (1995) Multiple essential functions of neuregulin in development *Nature* 378, 386-90.

Moore, G. J. (1994) Designing peptide mimetics *Trends Pharmacol Sci* 15, 124-129.

Moscatello, D. K., Holgado-Madruga, M., Emlet, D. R., Montgomery, R. B. & Wong, A. J. (1998) Constitutive activation of phosphatidylinositol 3-kinase by a naturally occurring mutant epidermal growth factor receptor *J Biol Chem* 273, 200-6.

Murali, R., Brennan, P. J., KieberEmmons, T. & Greene, M. I. (1996a) Structural analysis of p185(c-neu) and epidermal growth factor receptor tyrosine kinases: Oligomerization of kinase domains *Proceedings of the National Academy of Sciences of the United States of America* 93, 6252-6257.

Murali, R., Brennan, P. J., KieberEmmons, T. & Greene, M. I. (1996b) Structural analysis of p185(c-neu) and epidermal growth factor receptor tyrosine kinases: Oligomerization of kinase domains *Proc. Natl. Acad. Sci. U.S.A.* 93, 6252-6257.

Murali, R. & Greene, M. I. (1998) Structure-based design of immunologically active therapeutic peptides *Immunol Res* 17, 163-169.

Myers, M. P., Pass, I., Batty, I. H., Van der Kaay, J., Stolarov, J. P., Hemmings, B. A., Wigler, M. H., Downes, C. P. & Tonks, N. K. (1998) The lipid phosphatase activity of PTEN is critical for its tumor supressor function *Proc Natl Acad Sci USA* 95, 13513-8.

Myers, M. P. & Tonks, N. K. (1997) PTEN: sometimes taking it off can be better than putting it on *Am J Hum Genet* 61, 1234-8.

Nagane, M., Coufal, F., Lin, H., Bogler, O., Cavenee, W. K. & Huang, H. J. (1996) A common mutant epidermal growth factor receptor confers enhanced tumorigenicity on human glioblastoma cells by increasing proliferation and reducing apoptosis *Cancer Res* 56, 5079-86.

Nagane, M., Levitzki, A., Gazit, A., Cavenee, W. K. & Huang, H. J. (1998) Drug resistance of human glioblastoma cells conferred by a tumor-specific mutant epidermal growth factor receptor through modulation of Bcl-XL and caspase-3-like proteases *Proc Natl Acad Sci USA*

Naismith, J. H., Devine, T. Q., Brandhuber, B. J. & Sprang, S. R. (1995) Crystallographic evidence for dimerization of unliganded tumor necrosis factor receptor *J Biol Chem* 270, 13303-13307.

Naismith, J. H. & Sprang, S. R. (1998) Modularity in the TNF-receptor family *Trends Biochem Sci* 23, 74-9.

Nayak, B. P., Tuteja, R., Manivel, V., Roy, R. P., Vishwakarma, R. A. & Rao, K. V. (1998) B cell responses to a peptide epitope. V. Kinetic regulation of repertoire discrimination and antibody optimization for epitope *J Immunol* 161, 3510-3519.

Nishikawa, R., Ji, X. D., Harmon, R. C., Lazar, C. S., Gill, G. N., Cavenee, W. K. & Huang, H. J. (1994) A mutant epidermal growth factor receptor common in human glioma confers enhanced tumorigenicity *Proc Natl Acad Sci USA* 91, 7727-31.

O'Rourke, D. M., Kao, G. D., Singh, N., Park, B. W., Muschel, R. J., Wu, C. J. & Greene, M. I. (1998) Conversion of a radioresistant phenotype to a more sensitive one by disabling erbB receptor signaling in human cancer cells *Proc Natl Acad Sci USA* 95, 10842-7.

O'Rourke, D. M., Qian, X., Zhang, H. T., Davis, J. G., Nute, E., Meinkoth, J. & Greene, M. I. (1997) Trans receptor inhibition of human glioblastoma cells by erbB family ectodomains *Proc Natl Acad Sci USA* 94, 3250-5.

Pages, P., Benali, N., Saint-Laurent, N., Esteve, J. P., Schally, A. V., Tkaczuk, J., Vaysse, N., Susini, C. & Buscail, L. (1999) sst2 somatostatin receptor mediates cell cycle arrest and induction of p27(Kip1). Evidence for the role of SHP-1 *J Biol Chem* 274, 15186-93.

Park, B. W., Zhang, H. T., Wu, C., Berezov, A., Zhang, X., Dua, R., Wang, Q., Kao, G., O'Rourke, D. M., Greene, M. I. & Murali, R. (2000) Rationally designed anti-HER2/neu peptide mimetic disables P185HER2/neu tyrosine kinases in vitro and in vivo *Nat. Biotechnol.* 18, 194-198.

Patel, G., Husman, W., Jehanli, A. M., Deadman, J. J., Green, D., Kakkar, V. V. & Brennand, D. M. (1999) A cyclic peptide analogue of the loop III region of platelet-derived growth factor-BB is a synthetic antigen for the native protein *J Pept Res* 53, 68-74.

Pegram, M. D., Lipton, A., Hayes, D. F., Weber, B. L., Baselga, J. M., Tripathy, D., Baly, D., Baughman, S. A., Twaddell, T., Glaspy, J. A. & Slamon, D. J. (1998) Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment *Journal of Clinical Oncology* 16, 2659-2671.

Pianetti, S., Arsura, M., Romieu-Mourez, R., Coffey, R. J. & Sonenshein, G. E. (2001) Her-2/neu overexpression induces NF-kappaB via a PI3-kinase/Akt pathway involving calpain-mediated degradation of IkappaB-alpha that can be inhibited by the tumor suppressor PTEN *Oncogene* 20, 1287-99.

Pinkas-Kramarski, R., Eilam, R., Alroy, I., Levkowitz, G., Lonai, P. & Yarden, Y. (1997) Differential expression of NDF/neuregulin receptors ErbB-3 and ErbB-4 and involvement in inhibition of neuronal differentiation *Oncogene* 15, 2803-2815.

Pinkas-Kramarski, R., Soussan, L., Waterman, H., Levkowitz, G., Alroy, I., Klapper, L., Lavi, S., Seger, R., Ratzkin, B. J., Sela, M. & Yarden, Y. (1996) Diversification of Neu differentiation factor and epidermal growth factor signaling by combinatorial receptor interactions *Embo J* 15, 2452-67.

Posthumus, W. P., Lenstra, J. A., van Nieuwstadt, A. P., Schaaper, W. M., van der Zeijst, B. A. & Meloen, R. H. (1991) Immunogenicity of peptides simulating a neutralization epitope of transmissible gastroenteritis virus *Virology* 182, 371-375.

Qian, X., Dougall, W. C., Fei, Z. & Greene, M. I. (1995) Intermolecular association and trans-phosphorylation of different neu-kinase forms permit SH2-dependent signaling and oncogenic transformation *Oncogene* 10, 211-219.

Qian, X., Dougall, W. C., Hellman, M. E. & Greene, M. I. (1994a) Kinase-deficient neu proteins suppress epidermal growth factor receptor function and abolish cell transformation *Oncogene.*

Qian, X., LeVea, C. M., Freeman, J. K., Dougall, W. C. & Greene, M. I. (1994b) Heterodimerization of epidermal growth factor receptor and wild-type or kinase-deficient Neu: A mechanism of interreceptor kinase activation and transphosphorylation *The Proceedings of the National Academy of Science USA* 91, 1500-1504.

Qian, X., O'Rourke, D. M., Fei, Z., Kao, C.-C., Zhang, H.-T. & Greene, M. I. (1998) Domain-specific interactions between the p185neu and EGF receptor kinases determine differential signalling outcomes. *J Biol Chem.*

Qian, X., O'Rourke, D. M., Fei, Z., Zhang, H. T., Kao, C. C. & Greene, M. I. (1999) Domain-specific interactions between the p185(neu) and epidermal growth factor receptor kinases determine differential signaling outcomes *J Biol Chem* 274, 574-83.

Riese, D. J., 2nd, Komurasaki, T., Plowman, G. D. & Stern, D. F. (1998) Activation of ErbB4 by the bifunctional epidermal growth factor family hormone epiregulin is regulated by ErbB2 *J Biol Chem* 273, 11288-94.

Riethmacher, D., Sonnenberg-Riethmacher, E., Brinkmann, V., Yamaai, T., Lewin, G. R. & Birchmeier, C. (1997) Severe neuropathies in mice with targeted mutations in the ErbB3 receptor *Nature* 389, 725-30.

Saragovi, H. U. & Greene, M. I. (1992) Constrained peptides and mimetics as probes of protein secondary structures. *Immunomethods* 1, 5-9.

Saxton, T. M., Henkemeyer, M., Gasca, S., Shen, R., Rossi, D. J., Shalaby, F., Feng, G. S. & Pawson, T. (1997) Abnormal mesoderm patterning in mouse embryos mutant for the SH2 tyrosine phosphatase Shp-2 *Embo J* 16, 2352-64.

Schechter, A. L., Stern, D. F., Vaidyanathan, L., Decker, S. J., Drebin, J. A., Greene, M. I. & Weinberg, R. A. (1984) The neu oncogene: an erb-B-related gene encoding a 185,000-Mr tumour antigen *Nature* 312, 513-516.

Schmidt, M. & Wels, W. (1996) Targeted inhibition of tumour cell growth by a bispecific single-chain toxin containing an antibody domain and TGF alpha *Br J Cancer* 74, 853-862.

Shayesteh, L., Lu, Y., Kuo, W. L., Baldocchi, R., Godfrey, T., Collins, C., Pinkel, D., Powell, B., Mills, G. B. & Gray, J. W. (1999) PIK3CA is implicated as an oncogene in ovarian cancer *Nat Genet* 21, 99-102.

Shi, Z. Q., Lu, W. & Feng, G. S. (1998) The Shp-2 tyrosine phosphatase has opposite effects in mediating the activation of extracellular signal-regulated and c-Jun NH2-terminal mitogen-activated protein kinases *J Biol Chem* 273, 4904-8.

Shi, Z. Q., Yu, D. H., Park, M., Marshall, M. & Feng, G. S. (2000) Molecular mechanism for the Shp-2 tyrosine phosphatase function in promoting growth factor stimulation of Erk activity *Molecular and Cellular Biology* 20, 1526-36.

Stambolic, V., Suzuki, A., de la Pompa, J. L., Brothers, G. M., Mirtsos, C., Sasaki, T., Ruland, J., Penninger, J. M., Siderovski, D. P. & Mak, T. W. (1998) Negative regulation of PKB/Akt-dependent cell survival by the tumor suppressor PTEN *Cell* 95, 29-39.

Steck, P. A., Pershouse, M. A., Jasser, S. A., Yung, W. K., Lin, H., Ligon, A. H., Langford, L. A., Baumgard, M. L., Hattier, T., Davis, T., Frye, C., Hu, R., Swedlund, B., Teng, D. H. & Tavtigian, S. V. (1997) Identification of a candidate tumour suppressor gene, MMAC1, at chromosome 10q23.3 that is mutated in multiple advanced cancers *Nat Genet* 15, 356-62.

Sun, D., Whitaker, J. N., Cao, L., Han, Q., Sun, S., Coleclough, C., Mountz, J. & Zhou, T. (1998) Cell death mediated by Fas-FasL interaction between glial cells and MBP-reactive T cells *J Neurosci Res* 52, 458-467.

Takada, T., Matozaki, T., Takeda, H., Fukunaga, K., Noguchi, T., Fujioka, Y., Okazaki, I., Tsuda, M., Yamao, T., Ochi, F. & Kasuga, M. (1998) Roles of the complex formation of SHPS-1 with SHP-2 in insulin-stimulated mitogen-activated protein kinase activation *J Biol Chem* 273, 9234-42.

Takasaki, W., Kajino, Y., Kajino, K., Murali, R. & Greene, M. I. (1997) Structure-based design and characterization of exocyclic peptidomimetics that inhibit TNF alpha binding to its receptor *Nature Biotechnology* 15, 1266-1270.

Tamura, M., Gu, J., Matsumoto, K., Aota, S., Parsons, R. & Yamada, K. M. (1998) Inhibition of cell migration, spreading, and focal adhesions by tumor suppressor PTEN *Science* 280, 1614-7.

Tonks, N. K. & Myers, M. P. (1999) Structural assets of a tumor suppressor *Science* 286, 2096-7.

Tzahar, E. & Yarden, Y. (1998) The ErbB-2/HER2 oncogenic receptor of adenocarcinomas: from orphanhood to multiple stromal ligands *Biochim Biophys Acta* 1377, M25-37.

Valero, M. L., Camarero, J. A., Adeva, A., Verdaguer, N., Fita, I., Mateu, M. G., Domingo, E., Giralt, E. & Andreu, D. (1995) Cyclic peptides as conformationally restricted models of viral antigens: application to foot-and-mouth disease virus *Biomed Pept Proteins Nucleic Acids* 1, 133-140.

van der Werf, S., Briand, J. P., Plaue, S., Burckard, J., Girard, M. & Van Regenmortel, M. H. (1994) Ability of linear and cyclic peptides of neutralization antigenic site 1 of poliovirus type 1 to induce virus cross-reactive and neutralizing antibodies *Res Virol* 145, 349-359.

Van Regenmortel, M. H. (1989) Structural and functional approaches to the study of protein antigenicity *Immunol Today* 10, 266-272.

Van Regenmortel, M. H. V. (1996) Mapping Epitope Structure and Activity: From One-Dimensional Prediction to Four-Dimensional Description of Antigenic Specificity *Methods* 9, 465-472.

Veillette, A., Thibaudeau, E. & Latour, S. (1998) High expression of inhibitory receptor SHPS-1 and its association with protein-tyrosine phosphatase SHP-1 in macrophages *J Biol Chem* 273, 22719-28.

Vita, C., Vizzavona, J., Drakopoulou, E., Zinn-Justin, S., Gilquin, B. & Menez, A. (1998) Novel miniproteins engineered by the transfer of active sites to small natural scaffolds *Biopolymers* 47, 93-100.

Vogelstein, B., Lane, D. & Levine, A. J. (2000) Surfing the p53 network *Nature* 408, 307-10.

Voice, J. K., Klemke, R. L., Le, A. & Jackson, J. H. (1999) Four human ras homologs differ in their abilities to activate Raf-1, induce transformation, and stimulate cell motility *J Biol Chem* 274, 17164-70.

Wada, T., Myers, J. N., Kokai, Y., Brown, V. I., Hamuro, J., LeVea, C. M. & Greene, M. I. (1990a) Anti-receptor antibodies reverse the phenotype of the cells transformed by two interacting proto-oncogene encoded receptor proteins *Oncogene* 5, 489-495.

Wada, T., Qian, X. L. & Greene, M. I. (1990b) Intermolecular Association of the P185Neu Protein and EGF Receptor Modulates EGF Receptor Function *Cell* 61, 1339-1347.

Waid, P. P., Flynn, G. A., Huber, E. W. & Sabol, J. S. (1996) Constrained amino acids. An approach to the synthesis of 3-substituted prolines *Tetrahedron Lett.* 37, 4091-4094.

Ward, C. W., Hoyne, P. A. & Flegg, R. H. (1995) Insulin and epidermal growth factor receptors contain the cysteine repeat motif found in the tumor necrosis factor receptor *Proteins* 22, 141-153.

Williams, W. V., London, S. D., Weiner, D. B., Wadsworth, S., Berzofsky, A., Robey, F. Rubin, D. H. & Greene, M. I. (1989) Immune response to a molecularly defined internal image idiotope *Journal of Immunology* 142, 4392-4400.

Wong, A. J., Ruppert, J. M., Bigner, S. H., Grzeschik, C. H., Humphrey, P. A., Bigner, D. S. & Vogelstein, B. (1992) Structural alterations of the epidermal growth factor receptor gene in human gliomas *Proc Natl Acad Sci USA* 89, 2965-9.

Worthylake, R., Opresko, L. K. & Wiley, H. S. (1999) ErbB-2 amplification inhibits down-regulation and induces constitutive activation of both ErbB-2 and epidermal growth factor receptors *J Biol Chem* 274, 8865-8874.

Wu, C., Chen, Z., Ullrich, A., Greene, M. I. & O'Rourke, D. (1999) Diminished signaling from transforming erbB receptors involves MAPK-independent activation of signal-regulatory proteins (SIRPs/SHPS-1). *EMBO*, Submitted.

Wu, C. J., Chen, Z., Ullrich, A., Greene, M. I. & O'Rourke, D. M. (2000) Inhibition of EGFR-mediated phosphoinositide-3-OH kinase (PI3-K) signaling and glioblastoma phenotype by signal-regulatory proteins (SIRPs) *Oncogene* 19, 3999-4010.

Wu, X., Senechal, K., Neshat, M. S., Whang, Y. E. & Sawyers, C. L. (1998) The PTEN/MMAC1 tumor suppressor phosphatase functions as a negative regulator of the phosphoinositide 3-kinase/Akt pathway *Proc Natl Acad Sci USA* 95, 15587-91.

Yamauchi, K. & Pessin, J. E. (1995) Epidermal growth factor-induced association of the SHPTP2 protein tyrosine phosphatase with a 115-kDa phosphotyrosine protein *J Biol Chem* 270, 14871-4.

Ye, D., Mendelsohn, J. & Fan, Z. (1999) Augmentation of a humanized anti-HER2 mAb 4D5 induced growth inhibition by a human-mouse chimeric anti-EGF receptor mAb C225 *Oncogene* 18, 731-738.

Zhang, X., Gaubin, M., Briant, L., Srikantan, V., Murali, R., Saragovi, U., Weiner, D., Devaux, C., Autiero, M., Piatier-Tonneau, D. & Greene, M. I. (1997) Synthetic CD4 exocyclics inhibit binding of human immunodeficiency virus type 1 envelope to CD4 and virus replication in T lymphocytes *Nat Biotechnol* 15, 150-4.

Zhang, X., Piatiertonneau, D., Auffray, C., Murali, R., Mahapatra, A., Zhang, F. Q., Maier, C. C., Saragovi, H. & Greene, M. I. (1996) Synthetic Cd4 Exocyclic Peptides Antagonize Cd4 Holoreceptor Binding and T-Cell Activation *Nature Biotechnology* 14, 472-475.

Zuckermann, R. N. (1993) The chemical synthesis of peptidomimetic libraries *Curr. Opin. Struct. Biol.* 3, 580-4.

Each reference cited herein is hereby incorporated by reference in its entirety.

---

What is claimed:

1. An isolated antibody which binds an amino acid sequence selected from the group consisting of Y-C-F-P-D-E-E-G-A-C-Y (SEQ ID NO:3); C-K-V-E-L-M-Y-P-P-P-Y-F-V-G-M-G-N-G-T-Q-I-Y-V-I-D-P-E-P-C (SEQ ID NO: 28); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); Y-C-P-I-W-K-F-P-D-E-E-C-Y (SEQ ID NO: 31); Y-C-L-V-W-K-Y-A-D-A-G-C-Y (SEQ ID NO: 32); Y-C-P-I-Y-K-Y-P-D-V-Q-C-Y (SEQ ID NO: 33); Y-C-F-I-F-K-Y-A-D-P-D-C-Y (SEQ ID NO: 34); Y-C-F-P-D-E-E-G-A-C-Y (SEQ ID NO: 35).

2. The isolated antibody of claim 1 wherein the antibody binds to a cystine knot of an erbB receptor.

3. The isolated antibody of claim 2 wherein the cystine knot is in subdomain IV of an erbB receptor.

4. The isolated antibody of claim 3 wherein the cystine knot is selected from the group consisting of the S22 loop and the S23 loop.

5. The isolated antibody of claim 1 wherein the antibody binds to an interaction surface in the extracellular domain of an erbB receptor.

6. The isolated antibody of claim 1 wherein the antibody is conjugated to a radioactive agent or a chemotherapeutic compound.

7. The isolated antibody of claim 6 wherein the antibody is conjugated to $^{18}$F, $^{47}$Sc, $^{67}$Cu, $^{86}$Y, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi.

8. The isolated antibody of claim 6 wherein the antibody is conjugated to methotrexate (amethopterin), doxorubicin (adrimycin), daunorubicin, cytosinarabinoside, etoposide, 5-4 fluorouracil, melphalan, chlorambucil, cyclophosphamide, cis-platin, vindesine, mitomycin, bleomycin, tamoxiphen, taxol, ricin, ricin A chain, *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain, cobra venom factor (CVF), gelonin (GEL), saporin (SAP), modeccin, viscumin or volkensin.

9. A recombinant antibody which binds an amino acid sequence selected from the group consisting of Y-C-F-P-D-E-E-G-A-C-Y (SEQ ID NO:3); C-K-V-E-L-M-Y-P-P-P-Y-F-V-G-M-G-N-G-T-Q-I-Y-V-I-D-P-E-P-C (SEQ ID NO: 28); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); Y-C-P-I-W-K-F-P-D-E-E-C-Y (SEQ ID NO: 31); Y-C-L-V-W-K-Y-A-D-A-G-C-Y (SEQ ID NO: 32); Y-C-P-I-Y-K-Y-P-D-V-Q-C-Y (SEQ ID NO: 33); Y-C-F-I-F-K-Y-A-D-P-D-C-Y (SEQ ID NO: 34); Y-C-F-P-D-E-E-G-A-C-Y (SEQ ID NO: 35).

10. The recombinant antibody of claim 9 wherein the antibody binds to a cystine knot of an erbB receptor.

11. The recombinant antibody of claim 10 wherein the cystine knot is in subdomain IV of an erbB receptor.

12. The recombinant antibody of claim 11 wherein the cystine knot is selected from the group consisting of the S22 loop and the S23 loop.

13. The recombinant antibody of claim 9 wherein the antibody binds to an interaction surface in the extracellular domain of an erbB receptor.

14. The recombinant antibody of claim 9 wherein the antibody is conjugated to a radioactive agent or a chemotherapeutic compound.

15. The recombinant antibody of claim 14 wherein the antibody is conjugated to $^{18}$F, $^{47}$Sc, $^{67}$Cu, $^{86}$Y, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi.

16. The recombinant antibody of claim 14 wherein the antibody is conjugated to methotrexate (amethopterin), doxorubicin (adrimycin), daunorubicin, cytosinarabinoside, etoposide, 5-4 fluorouracil, melphalan, chlorambucil, cyclophosphamide, cis-platin, vindesine, mitomycin, bleomycin, tamoxiphen, taxol, ricin, ricin A chain, *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain, cobra venom factor (CVF), gelonin (GEL), saporin (SAP), modeccin, viscumin or volkensin.

17. A pharmaceutical composition comprising the antibody of claim 1 or claim 9.

18. The pharmaceutical composition of claim 17, wherein the pharmaceutical composition is an injectable pharmaceutical composition.

19. The pharmaceutical composition of claim 17 further comprising a chemotherapeutic agent.

20. The pharmaceutical composition of claim 19 wherein the chemotherapeutic agent is methotrexate (amethopterin), doxorubicin (adrimycin), daunorubicin, cytosinarabinoside, etoposide, 5-4 fluorouracil, melphalan, chlorambucil, cyclophosphamide), cis-platin, vindesine, mitomycin, bleomycin, tamoxiphen, or taxol.

21. The isolated antibody of claim 1, wherein said antibody binds an amino acid sequence selected from the group consisting of Y-C-F-P-D-E-E-G-A-C-Y (SEQ ID NO:3); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); Y-C-P-I-W-K-F-P-D-E-E-C-Y (SEQ ID NO: 31); Y-C-L-V-W-K-Y-A-D-A-G-C-Y (SEQ ID NO: 32); Y-C-P-I-Y-K-Y-P-D-V-Q-C-Y (SEQ ID NO: 33); Y-C-F-I-F-K-Y-A-D-P-D-C-Y (SEQ ID NO: 34); Y-C-F-P-D-E-E-G-A-C-Y (SEQ ID NO: 35).

22. The recombinant antibody of claim 9, wherein said antibody binds an amino acid sequence selected from the group consisting of Y-C-F-P-D-E-E-G-A-C-Y (SEQ ID NO:3); C-K-I-E-F-M-Y-P-P-P-Y-L-D-N-E-R-S-N-G-T-I-I-H-I-K-E-K-H-L-C (SEQ ID NO: 29); C-S-L-S-I-F-D-P-P-P-F-Q-E-R-N-L-S-G-G-Y-L-H-I-Y-E-S-Q-L-C (SEQ ID NO: 30); Y-C-P-I-W-K-F-P-D-E-E-C-Y (SEQ ID NO: 31); Y-C-L-V-W-K-Y-A-D-A-G-C-Y (SEQ ID NO: 32); Y-C-P-I-Y-K-Y-P-D-V-Q-C-Y (SEQ ID NO: 33); Y-C-F-I-F-K-Y-A-D-P-D-C-Y (SEQ ID NO: 34); Y-C-F-P-D-E-E-G-A-C-Y (SEQ ID NO: 35).

\* \* \* \* \*

SEQUENCE LISTING

<160> NUMBER OF SEQ ID NOS: 45

<210> SEQ ID NO 1
<211> LENGTH: 7
<212> TYPE: PRT
<213> ORGANISM: Artificial Sequence
<220> FEATURE:
<223> OTHER INFORMATION: Synthetic sequence

<400> SEQUENCE: 1

Phe Pro Asp Glu Glu Gly Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic sequence

<400> SEQUENCE: 2

Phe Tyr Pro Asp Glu Glu Gly Ala
1               5

<210> SEQ ID NO 3
<211> LENGTH: 11
<212> TYPE: PRT
<213> ORGANISM: Artificial Sequence
<220> FEATURE:
<223> OTHER INFORMATION: ErbB2-S22-AFA peptide

<400> SEQUENCE: 3

Tyr Cys Phe Pro Asp Glu Glu Gly Ala Cys Tyr
1               5                   10

```
<210> SEQ ID NO 4
<211> LENGTH: 12
<212> TYPE: PRT
<213> ORGANISM: Artificial Sequence
<220> FEATURE:
<223> OTHER INFORMATION: Synthetic sequence

<400> SEQUENCE: 4

Ser Tyr Cys Phe Pro Asp Glu Glu Gly Ala Cys Tyr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic sequence

<400> SEQUENCE: 5

Gly Ser Tyr Cys Phe Pro Asp Glu Glu Gly Ala Cys Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic sequence

<400> SEQUENCE: 6

Gly Gly Ser Tyr Cys Phe Pro Asp Glu Glu Gly Ala Cys Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic sequence

<400> SEQUENCE: 7

Gly Gly Gly Ser Tyr Cys Phe Pro Asp Glu Glu Gly Ala Cys Tyr
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Synthetic sequence

<400> SEQUENCE: 8

Tyr Cys Phe Pro Asp Glu Glu Gly Ala Cys Tyr Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic sequence

<400> SEQUENCE: 9

Tyr Cys Phe Pro Asp Glu Glu Gly Ala Cys Tyr Gly Gly
1               5                   10

<210> SEQ ID NO 10
<211> LENGTH: 14
```

```
<212> TYPE: PRT
<213> ORGANISM: Artificial Sequence
<220> FEATURE:
<223> OTHER INFORMATION: Synthetic sequence

<400> SEQUENCE: 10

Tyr Cys Phe Pro Asp Glu Glu Gly Ala Cys Tyr Gly Gly Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic sequence

<400> SEQUENCE: 11

Tyr Cys Phe Pro Asp Glu Glu Gly Ala Cys Tyr Gly Gly Gly Ser
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Synthetic sequence

<400> SEQUENCE: 12

Tyr Cys Phe Tyr Pro Asp Glu Glu Gly Ala Cys Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic sequence

<400> SEQUENCE: 13

Ser Tyr Cys Phe Tyr Pro Asp Glu Glu Gly Ala Cys Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic sequence

<400> SEQUENCE: 14

Gly Ser Tyr Cys Phe Tyr Pro Asp Glu Glu Gly Ala Cys Tyr
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic sequence

<400> SEQUENCE: 15

Gly Gly Ser Tyr Cys Phe Tyr Pro Asp Glu Glu Gly Ala Cys Tyr
1               5                   10                  15

<210> SEQ ID NO 16
<211> LENGTH: 16
<212> TYPE: PRT
<213> ORGANISM: Artificial Sequence
```

```
<220> FEATURE:
<223> OTHER INFORMATION: Synthetic sequence

<400> SEQUENCE: 16

Gly Gly Gly Ser Tyr Cys Phe Tyr Pro Asp Glu Glu Gly Ala Cys Tyr
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic sequence

<400> SEQUENCE: 17

Tyr Cys Phe Tyr Pro Asp Glu Glu Gly Ala Cys Tyr Gly
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic sequence

<400> SEQUENCE: 18

Tyr Cys Phe Tyr Pro Asp Glu Glu Gly Ala Cys Tyr Gly Gly
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic sequence

<400> SEQUENCE: 19

Tyr Cys Phe Tyr Pro Asp Glu Glu Gly Ala Cys Tyr Gly Gly Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic sequence

<400> SEQUENCE: 20

Tyr Cys Phe Tyr Pro Asp Glu Glu Gly Ala Cys Tyr Gly Gly Gly Ser
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: Synthetic sequence

<400> SEQUENCE: 21

Gly Gly Ser Tyr
1

<210> SEQ ID NO 22
<211> LENGTH: 5
<212> TYPE: PRT
<213> ORGANISM: Artificial Sequence
<220> FEATURE:
<223> OTHER INFORMATION: Synthetic sequence
```

```
<400> SEQUENCE: 22

Gly Gly Gly Ser Tyr
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic sequence

<400> SEQUENCE: 23

Tyr Gly Gly Gly
1

<210> SEQ ID NO 24
<211> LENGTH: 5
<212> TYPE: PRT
<213> ORGANISM: Artificial Sequence
<220> FEATURE:
<223> OTHER INFORMATION: Synthetic sequence

<400> SEQUENCE: 24

Tyr Gly Gly Gly Ser
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic sequence

<400> SEQUENCE: 25

Tyr Cys Phe Pro Asp Glu Glu Gly Ala Cys Tyr Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic sequence

<400> SEQUENCE: 26

Tyr Cys Phe Pro Asp Glu Glu Gly Ala Cys Tyr Gly Gly Ser
1               5                   10

<210> SEQ ID NO 27
<211> LENGTH: 4
<212> TYPE: PRT
<213> ORGANISM: Artificial Sequence
<220> FEATURE:
<223> OTHER INFORMATION: Synthetic sequence

<400> SEQUENCE: 27

Tyr Gly Gly Ser
1

<210> SEQ ID NO 28
<211> LENGTH: 29
<212> TYPE: PRT
<213> ORGANISM: Artificial Sequence
<220> FEATURE:
<223> OTHER INFORMATION: Synthetic sequence

<400> SEQUENCE: 28
```

```
Cys Lys Val Glu Leu Met Tyr Pro Pro Pro Tyr Phe Val Gly Met Gly
1               5                   10                  15

Asn Gly Thr Gln Ile Tyr Val Ile Asp Pro Glu Pro Cys
            20                  25

<210> SEQ ID NO 29
<211> LENGTH: 30
<212> TYPE: PRT
<213> ORGANISM: Artificial Sequence
<220> FEATURE:
<223> OTHER INFORMATION: Synthetic sequence

<400> SEQUENCE: 29

Cys Lys Ile Glu Phe Met Tyr Pro Pro Pro Tyr Leu Asp Asn Glu Arg
1               5                   10                  15

Ser Asn Gly Thr Ile Ile His Ile Lys Glu Lys His Leu Cys
            20                  25                  30

<210> SEQ ID NO 30
<211> LENGTH: 29
<212> TYPE: PRT
<213> ORGANISM: Artificial Sequence
<220> FEATURE:
<223> OTHER INFORMATION: Synthetic sequence

<400> SEQUENCE: 30

Cys Ser Leu Ser Ile Phe Asp Pro Pro Pro Phe Gln Glu Arg Asn Leu
1               5                   10                  15

Ser Gly Gly Tyr Leu His Ile Tyr Glu Ser Gln Leu Cys
            20                  25

<210> SEQ ID NO 31
<211> LENGTH: 13
<212> TYPE: PRT
<213> ORGANISM: Artificial Sequence
<220> FEATURE:
<223> OTHER INFORMATION: erbB2-S22-APE peptide

<400> SEQUENCE: 31

Tyr Cys Pro Ile Trp Lys Phe Pro Asp Glu Glu Cys Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: erbB1-S22-ALG peptide

<400> SEQUENCE: 32

Tyr Cys Leu Val Trp Lys Tyr Ala Asp Ala Gly Cys Tyr
1               5                   10

<210> SEQ ID NO 33
<211> LENGTH: 13
<212> TYPE: PRT
<213> ORGANISM: Artificial Sequence
<220> FEATURE:
<223> OTHER INFORMATION: erbB3-S22-APQ peptide

<400> SEQUENCE: 33

Tyr Cys Pro Ile Tyr Lys Tyr Pro Asp Val Gln Cys Tyr
1               5                   10

<210> SEQ ID NO 34
```

<211> LENGTH: 13
<212> TYPE: PRT
<213> ORGANISM: Artificial Sequence
<220> FEATURE:
<223> OTHER INFORMATION: erbB4-S22-AFD peptide

<400> SEQUENCE: 34

Tyr Cys Phe Ile Phe Lys Tyr Ala Asp Pro Asp Cys Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: erbB2-S22-AFA peptide

<400> SEQUENCE: 35

Tyr Cys Phe Pro Asp Glu Glu Gly Ala Cys Tyr
1               5                   10

<210> SEQ ID NO 36
<211> LENGTH: 29
<212> TYPE: PRT
<213> ORGANISM: Artificial Sequence
<220> FEATURE:
<223> OTHER INFORMATION: Synthetic sequence

<400> SEQUENCE: 36

Cys Lys Val Glu Leu Met Tyr Pro Pro Pro Tyr Phe Val Gly Met Gly
1               5                   10                  15

Asn Gly Thr Gln Ile Tyr Val Ile Asp Pro Glu Pro Cys
            20                  25

<210> SEQ ID NO 37
<211> LENGTH: 29
<212> TYPE: PRT
<213> ORGANISM: Artificial Sequence
<220> FEATURE:
<223> OTHER INFORMATION: Synthetic sequence

<400> SEQUENCE: 37

Cys Lys Val Glu Leu Met Tyr Pro Pro Pro Tyr Phe Val Gly Met Gly
1               5                   10                  15

Asn Gly Thr Gln Ile Tyr Val Ile Asp Pro Glu Pro Cys
            20                  25

<210> SEQ ID NO 38
<211> LENGTH: 30
<212> TYPE: PRT
<213> ORGANISM: Artificial Sequence
<220> FEATURE:
<223> OTHER INFORMATION: Synthetic sequence

<400> SEQUENCE: 38

Pro Cys Pro Ile Asn Cys Thr His Ser Cys Val Asp Leu Asp Asp Lys
1               5                   10                  15

Gly Cys Pro Ala Glu Gln Arg Ala Ser Pro Leu Thr Ser Ile
            20                  25                  30

<210> SEQ ID NO 39
<211> LENGTH: 148
<212> TYPE: PRT
<213> ORGANISM: Homo sapiens

<400> SEQUENCE: 39

Gln Val Cys His Ala Leu Cys Ser Pro Glu Gly Cys Trp Gly Pro Glu
1               5                   10                  15

Pro Arg Asp Cys Val Ser Cys Arg Asn Val Ser Arg Gly Arg Glu Cys
            20                  25                  30

Val Asp Lys Cys Asn Leu Leu Glu Gly Glu Pro Arg Glu Phe Val Glu
        35                  40                  45

Asn Ser Glu Cys Ile Gln Cys His Pro Glu Cys Leu Pro Gln Ala Met
50                  55                  60

Asn Ile Thr Cys Thr Gly Arg Gly Pro Asp Asn Cys Ile Gln Cys Ala
65                  70                  75                  80

His Tyr Ile Asp Gly Pro His Cys Val Lys Thr Cys Pro Ala Gly Val
            85                  90                  95

Met Gly Glu Asn Asn Thr Leu Val Trp Lys Tyr Ala Asp Ala Gly His
        100                 105                 110

Val Cys His Leu Cys His Pro Asn Cys Thr Tyr Gly Cys Thr Gly Pro
    115                 120                 125

Gly Leu Glu Gly Cys Pro Thr Asn Gly Pro Lys Ile Pro Ser Ile Ala
130                 135                 140

Thr Gly Met Val
145

<210> SEQ ID NO 40
<211> LENGTH: 149
<212> TYPE: PRT
<213> ORGANISM: Homo sapiens

<400> SEQUENCE: 40

Leu Ala Cys His Gln Leu Cys Ala Arg Gly His Cys Trp Gly Pro Gly
1               5                   10                  15

Pro Thr Gln Cys Val Asn Cys Ser Gln Phe Leu Arg Gly Gln Glu Cys
            20                  25                  30

Val Glu Glu Cys Arg Val Leu Gln Gly Leu Pro Arg Glu Tyr Val Asn
        35                  40                  45

Ala Arg His Cys Leu Pro Cys His Pro Glu Cys Gln Pro Gln Asn Gly
50                  55                  60

Ser Val Thr Cys Phe Gly Pro Glu Ala Asp Gln Cys Val Ala Cys Ala
65                  70                  75                  80

His Tyr Lys Asp Pro Pro Phe Cys Val Ala Arg Cys Pro Ser Gly Val
            85                  90                  95

Lys Pro Asp Leu Ser Tyr Met Pro Ile Trp Lys Phe Pro Asp Glu Glu
        100                 105                 110

Gly Ala Cys Gln Pro Cys Pro Ile Asn Cys Thr His Ser Cys Val Asp
    115                 120                 125

Leu Asp Asp Lys Gly Cys Pro Ala Glu Gln Arg Ala Ser Pro Leu Thr
130                 135                 140

Ser Ile Ile Ser Ala
145

<210> SEQ ID NO 41
<211> LENGTH: 147
<212> TYPE: PRT
<213> ORGANISM: Homo sapiens

<400> SEQUENCE: 41

Lys Val Cys Asp Pro Leu Cys Ser Ser Gly Gly Cys Trp Gly Pro Gly
1               5                   10                  15

Pro Gly Gln Cys Leu Ser Cys Arg Asn Tyr Ser Arg Gly Gly Val Cys

```
                20                  25                  30
Val Thr His Cys Asn Phe Leu Asn Gly Glu Pro Arg Glu Phe Ala His
            35                  40                  45

Glu Ala Glu Cys Phe Ser Cys His Pro Glu Cys Gln Pro Met Glu Gly
         50                  55                  60

Thr Ala Thr Cys Asn Gly Ser Gly Ser Asp Thr Cys Ala Gln Cys Ala
65                  70                  75                  80

His Phe Arg Asp Gly Pro His Cys Val Ser Ser Cys Pro His Gly Val
                85                  90                  95

Leu Gly Ala Lys Gly Pro Ile Tyr Lys Tyr Pro Asp Val Gln Asn Glu
            100                 105                 110

Cys Arg Pro Cys His Glu Asn Cys Thr Gln Gly Cys Lys Gly Pro Glu
            115                 120                 125

Leu Gln Asp Cys Leu Gly Gln Thr Leu Val Leu Ile Gly Lys Thr His
            130                 135                 140

Leu Thr Met
145

<210> SEQ ID NO 42
<211> LENGTH: 148
<212> TYPE: PRT
<213> ORGANISM: Homo sapiens

<400> SEQUENCE: 42

Met Val Cys Asn His Leu Cys Ser Ser Asp Gly Cys Trp Gly Pro Gly
1               5                   10                  15

Pro Asp Gln Cys Leu Ser Cys Arg Arg Phe Ser Arg Gly Arg Ile Cys
            20                  25                  30

Ile Glu Ser Cys Asn Leu Tyr Asp Gly Glu Phe Arg Glu Phe Glu Asn
            35                  40                  45

Gly Ser Ile Cys Val Glu Cys Asp Pro Gln Cys Glu Lys Met Glu Asp
         50                  55                  60

Gly Leu Leu Thr Cys His Gly Pro Gly Pro Asp Asn Cys Thr Lys Cys
65                  70                  75                  80

Ser His Phe Lys Asp Gly Pro Asn Cys Val Glu Lys Cys Pro Asp Gly
                85                  90                  95

Leu Gln Gly Ala Asn Ser Phe Ile Phe Lys Tyr Ala Asp Pro Asp Arg
            100                 105                 110

Glu Cys His Pro Cys His Pro Asn Cys Thr Gln Gly Cys Asn Gly Pro
            115                 120                 125

Thr Ser His Asp Cys Ile Tyr Tyr Pro Trp Thr Gly His Ser Thr Leu
            130                 135                 140

Pro Gln His Ala
145

<210> SEQ ID NO 43
<211> LENGTH: 12
<212> TYPE: PRT
<213> ORGANISM: Artificial Sequence
<220> FEATURE:
<223> OTHER INFORMATION: Synthetic sequence

<400> SEQUENCE: 43

Phe Cys Tyr Ile Gly Glu Val Glu Asp Gln Cys Tyr
1               5                   10

<210> SEQ ID NO 44
<211> LENGTH: 31
```

-continued

```
<212> TYPE: DNA
<213> ORGANISM: Artificial Sequence
<220> FEATURE:
<223> OTHER INFORMATION: Synthetic primer

<400> SEQUENCE: 44
cgcccggatc ctggcctgcc accagctgtg c                                  31

<210> SEQ ID NO 45
<211> LENGTH: 33
<212> TYPE: DNA
<213> ORGANISM: Artificial Sequence
<220> FEATURE:
<223> OTHER INFORMATION: Synthetic primer

<400> SEQUENCE: 45
cgcccgcggc cgccgcagag atgatggagt cag                                33
```